(12) United States Patent
Wang et al.

(10) Patent No.: US 11,274,351 B2
(45) Date of Patent: *Mar. 15, 2022

(54) METHODS AND COMPOSITIONS FOR DETECTING BACTERIAL CONTAMINATION

(71) Applicant: DCH MOLECULAR DIAGNOSTICS, INC., Sunnyvale, CA (US)

(72) Inventors: James Jian Quan Wang, Palo Alto, CA (US); Xiangmin Cui, Los Altos Hills, CA (US); Wayne Jer Hsieh, Sunnyvale, CA (US); HiuNam Chan, Daly City, CA (US)

(73) Assignee: DCH MOLECULAR DIAGNOSTICS, INC., Sunnyvale, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 16/460,536

(22) Filed: Jul. 2, 2019

(65) Prior Publication Data

US 2020/0080134 A1 Mar. 12, 2020

Related U.S. Application Data

(62) Division of application No. 14/900,260, filed as application No. PCT/US2014/047914 on Jul. 23, 2014, now Pat. No. 10,392,670.

(60) Provisional application No. 61/858,495, filed on Jul. 25, 2013.

(51) Int. Cl.
*C12Q 1/689* (2018.01)

(52) U.S. Cl.
CPC ........ *C12Q 1/689* (2013.01); *C12Q 2531/113* (2013.01)

(58) Field of Classification Search
CPC .............. C12Q 1/689; C12Q 2531/113; C12Q 2525/15
See application file for complete search history.

(56) References Cited

U.S. PATENT DOCUMENTS

| | | |
|---|---|---|
| 5,130,238 A | 7/1992 | Malek et al. |
| 5,234,809 A | 8/1993 | Boom et al. |
| 5,270,184 A | 12/1993 | Walker et al. |
| 5,310,652 A | 5/1994 | Gelfand et al. |
| 5,322,770 A | 6/1994 | Gelfand |
| 5,399,491 A | 3/1995 | Kacian et al. |
| 5,409,818 A | 4/1995 | Davey et al. |
| 5,455,166 A | 10/1995 | Walker |
| 5,480,784 A | 1/1996 | Kacian et al. |
| 5,494,810 A | 2/1996 | Barany et al. |
| 5,538,848 A | 7/1996 | Livak et al. |
| 5,641,658 A | 6/1997 | Adams et al. |
| 5,705,365 A | 1/1998 | Ryder et al. |
| 5,710,029 A | 1/1998 | Ryder et al. |
| 5,830,711 A | 11/1998 | Barany et al. |
| 5,854,033 A | 12/1998 | Lizardi |
| 5,888,779 A | 3/1999 | Kacian et al. |
| 5,925,517 A | 7/1999 | Tyagi et al. |
| 6,150,097 A | 11/2000 | Tyagi et al. |
| 6,251,639 B1 | 6/2001 | Kurn |
| 6,410,278 B1 | 6/2002 | Notomi et al. |
| 6,465,175 B2 | 10/2002 | Horn et al. |
| 6,814,934 B1 | 11/2004 | Higuchi |
| 7,001,724 B1 | 2/2006 | Greenfield et al. |
| 7,985,565 B2 | 7/2011 | Kawashima et al. |
| 10,392,670 B2 | 8/2019 | Wang et al. |
| 2004/0058378 A1 | 3/2004 | Kong et al. |
| 2008/0268432 A1 | 10/2008 | Ramirez-Arcos et al. |
| 2012/0035071 A1 | 2/2012 | Bergeron et al. |
| 2012/0125847 A1 | 5/2012 | Sehgal |
| 2012/0141990 A1 | 6/2012 | Paitan |
| 2013/0157265 A1* | 6/2013 | Mingorance Cruz .. C12Q 1/686 435/6.11 |

FOREIGN PATENT DOCUMENTS

| | | |
|---|---|---|
| EP | 0692540 A2 | 1/1996 |
| EP | 0684315 B1 | 6/2002 |
| EP | 2322668 A2 | 5/2011 |
| WO | WO-9513399 A1 | 5/1995 |
| WO | WO-9844151 A1 | 10/1998 |
| WO | WO-0018957 A1 | 4/2000 |
| WO | WO-0120035 A2 | 3/2001 |
| WO | WO-0123604 A2 | 4/2001 |
| WO | WO-0186001 A1 | 11/2001 |
| WO | WO-0210444 A1 | 2/2002 |
| WO | WO-2004046375 A2 | 6/2004 |
| WO | WO-2004050909 A2 | 6/2004 |
| WO | WO-2015013465 A2 | 1/2015 |

OTHER PUBLICATIONS

GenBank NCBI Reference Sequence: NR_118997.2 *Staphylococcus aureus* strain ATCC 12600 16S ribosomal RNA, complete sequence. Ludwig et al. (2014).*
Chinese Office Action dated Feb. 8, 2018 for CN Application No. CN201480041899 with English Translation.
Chinese Office Action dated Jun. 7, 2017 for CN Application No. CN201480041899 with English Translation.
Dergousoff, et al. Association of Different Genetic Types of Francisella-Like Organisms with the Rocky Mountain Wood Tick (Dermacentor andersoni) and the American Dog Tick (Dermacentor variabilis) in Localities Near Their Northern Distributional Limits Appl Environ Microbiol. Feb. 2012; 78(4): 965-971.
European search report and search opinion dated Feb. 14, 2017 for EP Application No. EP14829096.8.
Guatelli et al. Isothermal, in vitro amplification of nucleic acids by a multienzyme reaction modeled after retroviral replication. PNAS USA 87(5):1874-1878 (1990).

(Continued)

*Primary Examiner* — David C Thomas
(74) *Attorney, Agent, or Firm* — Wilson Sonsini Goodrich & Rosati

(57) ABSTRACT

Compositions, reactions mixtures, kits, and systems for detecting bacterial contamination are provided, as well as methods of using the same.

19 Claims, 20 Drawing Sheets

Specification includes a Sequence Listing.

(56) References Cited

OTHER PUBLICATIONS

International search report and written opinion dated Jan. 22, 2015 for PCT/US2014/047914.
Ishaq, et al. Insight into the bacterial gut microbiome of the North American Moose (Alces alces). BMC Microbiol. 2012; 12:212.
Jakobsson, et al. Changes in the predominant human Lactobacillus flora during in vitro fertilization. Ann Clin Microbiol Antimicrob. 2008; 7:14.
Japanese Office Action dated Jun. 22, 2018 for JP Application No. JP2016529875 with English Translation.
Kajiwara, et al. Isolation of Fucosyltransferase-Producing Bacteria from Marine Environments. Microbes Environ. Dec. 2012; 27(4): 515-518.
Landegren, U. Molecular mechanics of nucleic acid sequence amplification. Trends Genet. Jun. 1993;9(6):199-204.
Liu, et al. Comparison between 16S rDNA amplification and automated culture assay in detecting bacteria contamination of platelets concentrates. Chin J Blood Transfusion, 2008, vol. 21, No. 9, pp. 677-679.
Lizardi, et al. Exponential Amplification of Recombinant-RNA Hybridization Probes. Bio/Technology Oct. 1998; 6: 1197-1202.
Maiwald, M. Broad-range PCR for detection and identification of bacteria. Molecular Microbiology: Diagnostic Principles and Practice, 2nd Ed. American Society for Microbiology, Washington DC, 2011, pp. 491-505.
Michael, et al. Mfold web server for nucleic acid folding and hybridization prediction. Nucleic Acids Research. 31 (2003): 3406-3415.
Mohammadi, et al. Detection of bacteria in platelet concentrates: comparison of broad-range real-time 16S rDNA polymerase chain reaction and automated culturing. Transfusion 45.5 (2005): 731-736.
Mohammadi, et al. Optimization of real-time PCR assay for rapid and sensitive detection of eubacterial 16S ribosomal DNA in platelet concentrates. Journal of clinical microbiology 41.10 (2003): 4796-4798.
Nadkarni, et al. Determination of bacterial load by real-time PCR using a broad-range (universal) probe and primers set. Microbiology 148.1 (2002): 257-266.
Notice of allowance dated Apr. 19, 2019 for U.S. Appl. No. 14/900,260.
Notice of allowance dated May 15, 2019 for U.S. Appl. No. 14/900,260.
Office action dated Dec. 21, 2018 for U.S. Appl. No. 14/900,260.
Palavecino, et al. Bacterial contamination of platelets. Transfusion and Apheresis Science 42.1 (2010): 71-82.
Patel, et al. Development of an ethidium monoazide-enhanced internally controlled universal 16S rDNA real-time polymerase chain reaction assay for detection of bacterial contamination in platelet concentrates. Transfusion. Jul. 2012;52(7):1423-32. doi: 10.1111/j.1537-2995.2011,03484.x. Epub Dec. 21, 2011.
Qiagen. Critical Factors for Successful Real-Time PCR. Sample & Assay Technologies. Realtime PCR brochure Jul. 2010. http://www.gene-quantification.de/qiagen-qpcr-sample-assay-tech-guide-2010.pdf. Accessed Feb. 11, 2015. 64 pages.
Rinke, et al. Validation of picogram-and femtogram-input DNA libraries for microscale metagenomics. PeerJ 4 (2016): e2486, pp. 1-28.
Singaporean Search Report and Written Opinion dated Mar. 1, 2017 for Singaporean Application No. SG11201600550W.
Singaporean Written Opinion dated Apr. 2, 2018 for Singaporean Application No. SG11201600550W.
Wellinghausen, et al. Diagnosis of bacteremia in whole-blood samples by use of a commercial universal 16S rRNA gene-based PCR and sequence analysis. Journal of clinical microbiology 47.9 (2009): 2759-2765.
Whitcombe, et al. Detection of PCR products using self-probing amplicons and fluorescence. Nat Biotechnol. Aug. 1999;17(8):804-7.
Denman, et al. Development of a real-time PCR assay for monitoring anaerobic fungal and cellulolytic bacterial populations within the rumen. FEMS Microbiol Ecol. Dec. 2006. 58(3):572-582. doi: 10.1111/j.1574-6941.2006.00190.x.
GenBank Accession No. NC_007622 Version No. NC_007622.1 *Staphylococcus aureus* RF122, complete sequence. Record created Nov. 29, 2005. 2 pages. Retrieved Aug. 30, 2021 at URL: https://www.ncbi.nlm.nih.gov/nuccore/NC_007622.

* cited by examiner

Delta G     -4.67 kcal/mole  
Base Pairs   3

```
5'            TCCTACGGGAGGCAGCAGT
              | | |   :   :   : : :
3'   TGACGACGGAGGGCATCCT
```

FIG 6A

Delta G     -10.24 kcal/mole  
Base Pairs   6

```
5'   TCCTACGGGAGGCAGCAGT
              :   :   | | | | | |
3'            CACGGTCGTCGGCGCCATTATGC
```

FIG 6B

METHODS AND COMPOSITIONS FOR DETECTING BACTERIAL CONTAMINATION

CROSS-REFERENCE

This application is a divisional of U.S. application Ser. No. 14/900,260, filed Dec. 21, 2015, now U.S. Pat. No. 10,392,670, issued Aug. 27, 2019, which is a National Stage Entry of International Application No. PCT/US14/47914, filed Jul. 23, 2014, which claims the benefit of U.S. Provisional Application No. 61/858,495, filed Jul. 25, 2013, each of which is entirely incorporated herein by reference.

SEQUENCE LISTING

The instant application contains a Sequence Listing which has been filed electronically in ASCII format and is hereby incorporated by reference in its entirety. Said ASCII copy, created on Oct. 24, 2019, is named 44964-701_401_SL.txt and is 40,939 bytes in size.

BACKGROUND OF THE INVENTION

Microbial contamination of transplant tissues and blood transfusion products is a major medical problem. Blood banks are faced with a great challenge in testing each platelet bag for microbial contamination prior to release for infusion into a patient. Part of this challenge relates to the relatively short shelf-life of platelet samples, typically 5-7 days and sometimes shorter. The challenge with respect to platelets is further complicated by standard storage conditions. Platelets, unlike most other transplantable tissues, do not tolerate refrigeration and disappear rapidly from the circulation of recipients if subjected to even very short periods of chilling. This cooling effect on platelet survival is thought to be irreversible and renders platelets unsuitable for transfusion. When platelets are exposed to temperatures lower than 20° C., they rapidly undergo modifications in shape indicative of impairment. The need to keep platelets at room temperature (e.g. 22-25° C.) prior to transfusion has imposed a unique set of costly and complex logistical requirements for platelet storage. Because platelets are metabolically active at room temperature, they are typically subjected to constant agitation in gas permeable containers to allow for the exchange of gases to prevent the toxic consequences of metabolic acidosis. These storage conditions encourage the growth of bacteria thereby creating a higher risk of bacterial infection. Because screening methods that rely on detection by culture can take longer than the usable shelf-life to detect contamination, contaminated platelets are often infused into patients, and the physician is notified subsequently that the platelets were contaminated as the culture results become available. Under the American Association of Blood Banks (A.A.B.B.) standard 5.1.5.1, blood banks or transfusion services are instructed to have methods to limit and detect bacterial contamination in all platelet concentrates. Nevertheless, the risk of transfusion with bacterially contaminated platelets may be as a high as 1 in 1,000 units, with perhaps 10% to 25% of such incidents resulting in adverse effects on patients. While some contamination may derive from donor bacteraemia, contamination at the time of collection by bacteria present on the skin or in blood packs are main sources of contamination that cannot be addressed through donor diagnostic screening.

Common methods to mitigate contamination include preventative measures (e.g. arm cleansing, diverting a first portion of collected blood, and filtration) and culture methodologies. As evidenced by the current rate of contamination, these procedures remain inadequate. Moreover, because culture-based detection methods require significant incubation periods (sometimes days), samples may not be used for a significant portion of their useful life, and when they are used, detection may not be complete. This is particularly true for contamination by bacteria that are relatively slow growing. For example, the mean detection times for *Bacillus* sp., Staphylococcal sp., Streptococcal sp., *Micrococcus luteus, Kocuria varians, Corynebacterium* sp., and *Propionibacterium* sp. have been estimated as 24 hours, 27 hours, 34 hours, 47 hours, 56 hours, 87 hours, and 97 hours, respectively, using standard culture methods.

One commercially available test is referred to as the BacT/ALERT test (bioMérieux, Inc., Durham, N.C.). Bacterial detection is based on the evolution of carbon dioxide by proliferating bacteria. A carbon-dioxide-sensitive liquid emulsion sensor at the bottom of the culture bottle changes color and is detected through alteration of light reflected on the sensor. Another method for bacterial detection involves measuring the oxygen content in a platelet preparation sample. An example is the Pall eBDS test (Pall Corporation, Port Washington, N.Y.). The approach to detection measures the oxygen content of air within the sample pouch as a surrogate marker for bacteria. An oxygen analyzer is used to measure the percent of oxygen in the headspace gas of the pouch or bag having the platelets. If bacteria are present in the platelet sample collected, an increasing amount of oxygen is consumed through the metabolic activity and proliferation of the bacteria in the sample during incubation, resulting in a measurable decrease in oxygen content of the plasma as well as the air within the sample pouch. While the non-specific measure of bacterial growth permits detection of many kinds of bacteria, the sensitivity is relatively low and requires long incubation times.

Alternative methods to the standard culture-based screens include bacterial antigen detection and nucleic acid-based screening. A major limitation on antigen-based methods is that they cannot be applied directly for testing of samples where the spectrum of bacterial pathogens is unknown. Detection of common bacterial nucleic acid sequences, such as 16S rRNA has been proposed to achieve a broader spectrum of detection, but such methods have so far been deemed less sensitive and specific than current culture methods and not appropriate for early testing of platelet samples.

SUMMARY OF THE INVENTION

The present disclosure provides methods, compositions, reaction mixtures, kits, and systems for detecting contamination of biological samples, such as platelet samples, with both a broad range and high specificity and sensitivity of detection. Detection of contamination according to the disclosure is also significantly more rapid than culture-based screening methodologies.

In one aspect, the disclosure provides a method of detecting bacterial contamination of a sample by any of a plurality of bacterial species, such as at least eight bacterial species. In one embodiment, the method comprises subjecting the sample or a portion thereof to a nucleic acid amplification reaction under conditions to yield a detectable amount of an amplicon of no more than about 800, 700, 600, 500, 400, 300, 200, 150, or 100 bases in a single reaction mixture, said reaction mixture comprising a single primer pair and a single detectable probe, wherein the primer pair flanks the amplicon, the amplicon comprises a conserved sequence to which the detectable probe hybridizes, and the conserved sequence is identical among the at least eight bacterial species; and detecting hybridization to the amplicon by the probe, wherein the hybridization by the probe yields a detectable signal indicative of bacterial contamination of the sample by any of the at least eight bacterial species. In some embodiments, the sample is a blood sample or a buffy coat sample, and the contamination is predictive or diagnostic of sepsis in the subject. In some embodiments, the sample is a platelet sample. In some embodiments, the platelet sample is a platelet concentrate isolated by aphaeresis. In some embodiments, nucleic acids isolated from less than 5 mL of the platelet concentrate are subjected to the nucleic acid amplification reaction. In some embodiments, the amplicon is generated from a bacterial 16S rRNA polynucleotide template. In some embodiments, the detecting of bacterial contamination is completed prior to transfusion into a recipient. In some embodiments, the amplification reaction yields a detectable amount of amplicon of no more than 300 bases, or no more than 150 bases. In some embodiments, the amplification reaction yields a detectable amount of amplicon of 100-200 bases. In some embodiments, all of the bacterial species are Gram-positive bacteria, Gram-negative bacteria, or a combination of both detected in the same reaction with probes having different detectable labels. In some embodiments, the at least eight bacterial species comprise a plurality of Gram-positive bacterial species and a plurality of Gram-negative bacterial species. In some embodiments, the bacterial species are selected from the group consisting of: *Staphylococcus aureus, Staphylococcus aureus* Mu3; *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Propionibacterium granulosum, Pseudomonas aeruginosa, Serratia marcescens, Bacillus cereus, Staphylococcus aureus* Mu50, *Yersinia enterocolitica, Staphylococcus simulans, Micrococcus luteus*, and *Enterobacter aerogenes*. In some embodiments, the method comprises detecting bacterial contamination by any of at least ten or fifteen bacterial species in a sample. In some embodiments, the single primer pair comprises a first primer comprising at least 10 contiguous nucleotides of a sequence as set forth in Table 2 (e.g., SEQ ID NO: 4, 7, or 9) and a second primer comprising at least 10 nucleotides of a sequence as set forth in Table 2 (e.g., SEQ ID NO: 5, 6, 8, or 10). In some embodiments, the first and second primers are selected from the primer sets disclosed in Table 15, or any combinations thereof. In some embodiments, the first and second primer pairs exhibits at least 80%, 90%, 91%, 92%, 93%, 94%, 95%, 96%, 97%, 98%, or 99% sequence homology to any of the primers or complements thereof disclosed in Table 2 or Table 15, when optimally aligned. In some embodiments, the probe comprises at least 10 contiguous nucleotides of a sequence as set forth in Table 3, or a complement thereof. In some embodiments, the nucleic acid amplification reaction contains less than 5 pg of starting nucleic acids from the bacterial contamination. In some embodiments, the nucleic acid amplification reaction is performed using a method selected from the group consisting of: polymerase chain reaction, real-time polymerase chain reaction, isothermal amplification, strand displacement amplification, rolling circle amplification, ligase chain reaction, transcription-mediated amplification, solid phase amplification, nucleic acid sequence-based amplification (NASBA), and linear amplification. In some embodiments, the nucleic acid amplification reaction is performed in a well, in a plate, in a tube, in a chamber, in a droplet, in a flow cell, in a slide, in a chip, attached to a solid substrate, attached to a bead, or in an emulsion. In some embodiments, the detectable signal has a linear range of detection across at least 5 logs. In some embodiments, the method further comprises determining the amount of bacterial contamination based on the probe signal.

In another aspect, the disclosure provides a method of detecting bacterial contamination of a sample. In one embodiment, the method comprises subjecting the sample or a portion thereof to a nucleic acid amplification reaction under conditions to yield a detectable amount of an amplicon of no more than about 800, 700, 600, 500, 400, 300, 200, 150, or 100 bases in a single reaction mixture, said reaction mixture comprising a single primer pair and a single detectable probe, wherein the primer pair flanks the amplicon, the amplicon comprises a conserved sequence to which the detectable probe hybridizes, and the sample or portion thereof has not been cultured at a temperature above 35° C. prior to amplification; and detecting hybridization to the amplicon by the probe, wherein the hybridization by the probe yields a detectable signal indicative of bacterial contamination of the sample. In some embodiments, the sample is a blood sample or a buffy coat sample, and the contamination is predictive or diagnostic of sepsis in the subject. In some embodiments, the sample is a platelet sample. In some embodiments, the platelet sample is a platelet concentrate isolated by aphaeresis. In some embodiments, nucleic acids isolated from less than 5 mL of the platelet concentrate are subjected to the nucleic acid amplification reaction. In some embodiments, nucleic acids isolated from less than 5 mL of the platelet concentrate are subjected to the nucleic acid amplification reaction. In some embodiments, the amplicon is generated from a bacterial 16S rRNA polynucleotide template. In some embodiments, the detecting of bacterial contamination is completed prior to transfusion into a recipient. In some embodiments, the amplification reaction yields a detectable amount of amplicon of no more than 300 bases, or no more than 150 bases. In some embodiments, the amplification reaction yields a detectable amount of amplicon of 100-200 bases. In some embodiments, the method comprises detecting bacterial contamination by any of at least ten or fifteen bacterial species in a sample. In some embodiments, the single primer pair comprises a first primer comprising at least 10 contiguous nucleotides of a sequence as set forth in SEQ ID NO: 4, 7, or 9 and a second primer comprising at least 10 nucleotides of a sequence as set forth in SEQ ID NO: 5, 6, 8, or 10. In some embodiments, the probe comprises at least 10 contiguous nucleotides of a sequence as set forth in Table 3, or a complement thereof. In some embodiments, the nucleic acid amplification reaction contains less than 5 pg of starting nucleic acids from the bacterial contamination. In some embodiments, the nucleic acid amplification reaction is performed using a method selected from the group consisting of: polymerase chain reaction, real-time polymerase chain reaction, isothermal amplification, strand displacement amplification, rolling circle amplification, ligase chain reaction, transcription-mediated amplification, solid phase amplification, nucleic acid sequence-based amplification (NASBA), and linear amplification. In some embodiments, the nucleic acid amplification reaction is performed in a well, in a plate, in a tube, in a chamber, in a droplet, in a flow cell, in a slide, in a chip, attached to a solid substrate, attached to a bead, or in an emulsion. In some embodiments, the detectable signal has a linear range of detection across at least 5 logs. In some embodiments, the method further comprises determining the amount of bacterial contamination based on the probe signal.

In one aspect, the disclosure provides a method of rapidly detecting bacterial contamination in a sample within 24 hours after obtaining the sample. In one embodiment, the method comprises subjecting the sample or a portion thereof to a nucleic acid amplification reaction with a single primer pair and a single detectable probe in a single reaction mixture under conditions to yield a detectable amount of an amplicon of no more than about 800, 700, 600, 500, 400, 300, 200, 150, or 100 bases, wherein the primer pair flanks the amplicon, the amplicon comprises a conserved sequence to which the detectable probe hybridizes, and amplification of about 1 pg-5 pg of DNA from any one of the species has a cycle threshold value ($C_T$) of less than 30; and within about 24 hours after obtaining said sample, detecting hybridization to said amplicon by said probe, wherein said hybridization by said probe yields a detectable signal indicative of bacterial contamination of the sample, thereby detecting the contamination within about 24 hours from obtaining said sample. In some embodiments, the sample is a blood sample or a buffy coat sample, and the contamination is predictive or diagnostic of sepsis in the subject. In some embodiments, the sample is a platelet sample. In some embodiments, the platelet sample is a platelet concentrate isolated by aphaeresis. In some embodiments, nucleic acids isolated from less than 5 mL of the platelet concentrate are subjected to the nucleic acid amplification reaction. In some embodiments, the detection yields a detectable signal indicative of bacterial contamination of a platelet sample having a bacterial load of about 1.0 colony forming unit per mL (CFU/mL). In some embodiments, nucleic acids isolated from less than 5 mL of the platelet concentrate are subjected to the nucleic acid amplification reaction. In some embodiments, the amplicon is generated from a bacterial 16S rRNA polynucleotide template. In some embodiments, the detecting of bacterial contamination is completed prior to transfusion into a recipient. In some embodiments, the amplification reaction yields a detectable amount of amplicon of no more than 300 bases, or no more than 150 bases. In some embodiments, the amplification reaction yields a detectable amount of amplicon of 100-200 bases. In some embodiments, the method comprises detecting bacterial contamination by any of at least ten or fifteen bacterial species in a sample. In some embodiments, the single primer pair comprises a first primer comprising at least 10 contiguous nucleotides of a sequence as set forth in SEQ ID NO: 4, 7, or 9 and a second primer comprising at least 10 nucleotides of a sequence as set forth in SEQ ID NO: 5, 6, 8, or 10. In some embodiments, the probe comprises at least 10 contiguous nucleotides of a sequence as set forth in Table 3, or a complement thereof. In some embodiments, the nucleic acid amplification reaction contains less than 5 pg of starting nucleic acids from the bacterial contamination. In some embodiments, the nucleic acid amplification reaction is performed using a method selected from the group consisting of: polymerase chain reaction, real-time polymerase chain reaction, isothermal amplification, strand displacement amplification, rolling circle amplification, ligase chain reaction, transcription-mediated amplification, solid phase amplification, nucleic acid sequence-based amplification (NASBA), and linear amplification. In some embodiments, the nucleic acid amplification reaction is performed in a well, in a plate, in a tube, in a chamber, in a droplet, in a flow cell, in a slide, in a chip, attached to a solid substrate, attached to a bead, or in an emulsion. In some embodiments, the detectable signal has a linear range of detection across at least 5 logs. In some embodiments, the method further comprises determining the amount of bacterial contamination based on the probe signal.

In another aspect, the disclosure provides a method of detecting bacterial contamination by any of a plurality of bacterial species from different genera in a sample (e.g. a biological sample of a subject). In one embodiment, the method comprises performing a nucleic acid amplification reaction on the sample or a portion thereof with a single primer pair to yield a detectable amount of an amplicon of no more than about 800, 700, 600, 500, 400, 300, 200, 150, or 100 bases of a 16S rRNA polynucleotide, wherein amplification of about 1 pg-5 pg of DNA from any one of the species has a cycle threshold value ($C_T$) of less than 30; and detecting the amplicon with one or more detectable probes, wherein each of the one or more detectable probes specifically hybridizes to a conserved sequence, and the conserved sequence is identical among a plurality of bacterial species from different genera. In some embodiments, the sample is a blood sample or a buffy coat sample, and the contamination is predictive or diagnostic of sepsis in the subject. In some embodiments, the sample is a platelet sample. In some embodiments, the $C_T$ for a negative control sample is at least 5 cycles higher than the $C_T$ for a sample containing 1 pg-5 pg of DNA from any one of the at least 5 bacterial species. In some embodiments, the one or more detectable probes comprises no more than 5 different probes, or no more than 2 different probes. In some embodiments, the one or more detectable probes consists of one probe. In some embodiments, the detecting of bacterial contamination is completed prior to transfusion into a recipient. In some embodiments, the amplification reaction yields a detectable amount of amplicon of no more than 300 bases, or no more than 150 bases. In some embodiments, the amplification reaction yields a detectable amount of amplicon of 100-200 bases. In some embodiments, all of the bacterial species are Gram-positive bacteria, Gram-negative bacteria, or a combination of both detected in the same reaction with probes having different detectable labels. In some embodiments, the plurality of bacterial species comprise a plurality of Gram-positive bacterial species from different genera and a plurality of Gram-negative bacterial species from different genera. In some embodiments, the one or more detectable probes comprise a first probe that specifically hybridizes to a conserved sequence common among the Gram-positive bacterial species and absent in at least some of the Gram-negative species, and a second probe that specifically hybridizes to a conserved sequence common among the Gram-negative bacterial species and absent in at least some of the Gram-positive species. In some embodiments, the bacterial species are selected from the group consisting of: *Staphylococcus aureus, Staphylococcus aureus* Mu3; *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Propionibacterium granulosum, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes*. In some embodiments, the method comprises detecting bacterial contamination by any of at least ten or fifteen bacterial species in a sample. In some embodiments, the single primer pair comprises a first primer comprising at least 10 contiguous nucleotides of a sequence as set forth in SEQ ID NO: 4, 7, or 9 and a second primer comprising at least 10 nucleotides of a sequence as set forth in SEQ ID NO: 5, 6, 8, or 10. In some embodiments, the probe comprises at least 10 contiguous nucleotides of a sequence as set forth in Table 3, or a complement thereof. In some embodiments, the nucleic acid amplification reaction contains less than 5 pg of starting nucleic acids from the bacterial contamination. In some embodiments, the nucleic acid amplification reaction is performed using a method selected from the group consisting of: polymerase chain reaction, real-time polymerase chain reaction, isothermal amplification, strand displacement amplification, rolling circle amplification, ligase chain reaction, transcription-mediated amplification, solid phase amplification, nucleic acid sequence-based amplification (NASBA), and linear amplification. In some embodiments, the nucleic acid amplification reaction is performed in a well, in a plate, in a tube, in a chamber, in a droplet, in a flow cell, in a slide, in a chip, attached to a solid substrate, attached to a bead, or in an emulsion. In some embodiments, the probe yields a signal that has a linear range of detection across at least 5 logs. In some embodiments, the method further comprises determining the abundance of the plurality of bacterial species based on the probe signal.

In one aspect, the disclosure provides a composition for amplification and detection of a portion of a 16S rRNA polynucleotide. In some embodiments, the portion is less than about 800, 700, 600, 500, 400, 300, 200, 150, or 100 nucleotides in length. In one embodiment, the composition comprises a first primer comprising at least 10 contiguous nucleotides of the sequence as set forth Table 2 or Table 15 including but not limited to SEQ ID NO: 9; a second primer comprising at least 10 contiguous nucleotides of the sequence as set forth in Table 2 or Table 15 including but not limited to SEQ ID NO: 10; and a probe comprising at least 10 contiguous nucleotides of the sequence as set forth in Table 3 including but not limited to SEQ ID NO: 16, or the complement thereof. In one embodiment, the composition comprises primers that, in an amplification reaction with a target 16S rRNA polynucleotide, amplify an amplicon of at least 50 nucleotides in length, the amplicon having 90% sequence identity with any of sequences listed in Table 1 including but not limited to SEQ ID NO: 1-3 when optimally aligned; and one or more probes that specifically hybridize to either strand of the amplicon. In some embodiments, the composition is in a container, such as a well, a plate, a tube, a chamber, a flow cell, or a chip. In some embodiments, the composition is in a dehydrated form. In some embodiments, in an amplification reaction with a target 16S rRNA polynucleotide, amplification of about 1 pg-5 pg of DNA from any one of a plurality of target species by the primers and probes has a cycle threshold value ($C_T$) of less than 30.

In another aspect, the disclosure provides a method of detecting bacterial contamination of a platelet sample by any of at least five bacterial species. The method comprises: subjecting the sample or a portion thereof to a nucleic acid amplification reaction under conditions to yield a detectable amount of an amplicon of no more than about 800 bases in a reaction mixture, said reaction mixture comprising a first forward primer and a first reverse primer, wherein the first forward primer and the first reverse primer each hybridizes to a separate region that is conserved amongst at least 5 different bacterial genomes; detecting from said reaction mixture a signal indicative of the presence of said amount of an amplicon, thereby detecting bacterial contamination of a platelet sample by any of the at least five bacterial species. In one embodiment, the first forward and first reverse primer each hybridizes to a separate region that is conserved amongst at least 6, 7, 8, 9, 10, 11, 12, 13, 14, 15, 16, 17, 18, 19, 20, 21, 22, 23, 24, 25 or even more different bacterial genomes. The conserved region can encompass the region from 9 to 28, from 32 to 48, from 522 to 545, from 888 to 903, from 916 to 937, from 939 to 973, from 975 to 994, from 957 to 981, from 1093 to 1125, from 1184 to 1206, from 1231 to 1252, from 1378 to 1396, from 1398 to 1422, or from 1496 to 1516, of 16S rRNA of *Staphylococcus aureus* (GenBank accession Number NC_007622) or the corresponding regions in any one of the bacterial genomes: *Staphylococcus aureus* Mu3; *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Serratia marcescens, Bacillus cereus, Propionibacterium sp., Staphylococcus aureus* Mu50, *Yersinia enterocolitica, Staphylococcus simulans, Micrococcus luteus,* and *Enterobacter aerogenes*. Any of the primers disclosed herein including the primer sets listed in Table 15 can be utilized for practice of this and other methods disclosed herein. In some embodiment, the first forward primer and the first reverse primer each exhibits at least 80%, 85%, 90%, 95%, 96%, 97%, 98%, 99%, or 100% sequence homology with the separate region of the target bacterial sequence when optimally aligned. In some embodiment, the reaction mixture further comprises a second forward primer exhibiting at least 80%, 85%, 90%, 95%, 96%, 97%, 98%, 99%, or 100% sequence homology when optimally aligned with any or all of the at least 5, 6, 7, 8, 9, 10, 11, 12, 13, 14, 15, 16, 17, 18, 19, 20, 21, 22, 23, 24, 25 or more bacterial species. In some embodiment, the reaction mixture further comprises a second reverse primer exhibiting at least 80%, 85%, 90%, 95%, 96%, 97%, 98%, 99%, or 100% sequence homology when optimally aligned with any or all of the at least 5, 6, 7, 8, 9, 10, 11, 12, 13, 14, 15, 16, 17, 18, 19, 20, 21, 22, 23, 24, 25 or more bacterial species. The region of homology can include but are not limited to any conserved regions disclosed herein, e.g., from 9 to 28, from 32 to 48, from 522 to 545, from 888 to 903, from 916 to 937, from 939 to 973, from 975 to 994, from 957 to 981, from 1093 to 1125, from 1184 to 1206, from 1231 to 1252, from 1378 to 1396, from 1398 to 1422, or from 1496 to 1516, of 16S rRNA of *Staphylococcus aureus* (GenBank accession Number NC_007622) or the corresponding regions in any one of the bacterial genomes referenced herein. Where desired, the reaction mixture further comprises a detectable label, including but not limited to a DNA-binding dye or other label molecules disclosed herein. In some embodiment, the nucleic acid amplification is performed under conditions such that about 1 pg-5 pg of DNA from any one of the at least 5, 6, 7, 8, 9, 10, 11, 12, 13, 14, 15, 16, 17, 18, 19, 20, 21, 22, 23, 24, 25 or more bacterial species has a cycle threshold value ($C_T$) of less than 30.

In one aspect, the disclosure provides a reaction mixture for amplification and detection of a portion of a 16S rRNA polynucleotide. In some embodiments, the portion is less than about 800, 700, 600, 500, 400, 300, 200, 150, or 100 nucleotides in length. In some embodiments, the reaction mixture comprises sample nucleic acid; primers that, in an amplification reaction with a target 16S rRNA polynucleotide, amplify an amplicon of at least 50 nucleotides in length, the amplicon having 90% sequence identity with any of SEQ ID NO: 1-3 when optimally aligned; a probe that specifically hybridizes to either strand of the amplicon; and a polymerase; wherein the reaction mixture is in a reaction site. In some embodiments, the reaction site is a droplet, a well, a plate, a tube, a chamber, a flow cell, or a chip. In some embodiments, in an amplification reaction with a target 16S rRNA polynucleotide, amplification of about 1 pg-5 pg of DNA from any one of a plurality of target species by the primers and probes has a cycle threshold value ($C_T$) of less than 30.

In one aspect, the disclosure provides a kit for the detection of bacterial contamination in a sample, such as in a platelet sample. In one embodiments, the kit comprises a first primer comprising at least 10 contiguous nucleotides of a sequence as set forth in Table 2 or Table 15 including but not limited to SEQ ID NO: 9; a second primer comprising at least 10 contiguous nucleotides of a sequence as set forth in Table 2 or Table 15 including but not limited to SEQ ID NO: 10; a probe comprising at least 10 contiguous nucleotides of a sequence as set forth in Table 3 including but not limited to SEQ ID NO: 16, or the complement thereof.

In one aspect, the disclosure provides a method for using a kit of the disclosure. In one embodiment, the method comprises performing a nucleic acid amplification reaction on a sample or a portion thereof with a single primer pair to yield a detectable amount of an amplicon of no more than about 800, 700, 600, 500, 400, 300, 200, 150, or 100 bases of a 16S rRNA polynucleotide, wherein amplification of about 1 pg-5 pg of DNA from any one of a plurality of bacterial species from different genera has a cycle threshold value ($C_T$) of less than 30; and detecting the amplicon with one or more detectable probes, wherein each of the one or more detectable probes specifically hybridizes to a conserved sequence, and the conserved sequence is identical among a plurality of bacterial species from different genera.

In one aspect, the disclosure provides a system for detecting bacterial contamination of a sample (e.g. a platelet sample, a blood sample, or a buffy coat sample) by any of a plurality of bacterial species from different genera. In one embodiment, the system comprises a computer configured to receive a customer request to perform a detection reaction on a sample; an amplification system that performs a nucleic acid amplification reaction on the sample or a portion thereof in response to the customer request, wherein the amplification reaction yields a detectable amount of an amplicon of no more than about 800, 700, 600, 500, 400, 300, 200, 150, or 100 bases of a 16S rRNA polynucleotide using a single primer pair and single probe, and further wherein amplification of 1 pg-5 pg of DNA from any one of the at least five genera has a $C_T$ of less than 30; and a report generator that sends a report to a recipient, wherein the report contains results for detection of a signal intensity produced by the probe. In some embodiments, the report generator identifies the sample as contaminated or not contaminated based on the signal intensity produced by the probe. In some embodiments, the recipient is the customer.

In one aspect, the disclosure provides a computer readable medium. In some embodiments, the computer readable medium comprises codes that, upon execution by one or more processors, implement a method of detecting bacterial contamination of a platelet sample by any of a plurality of bacterial species from different genera. In one embodiment, the method implemented upon execution of the codes comprises receiving a customer request to perform a detection reaction on a sample; performing a nucleic acid amplification reaction on the sample or a portion thereof in response to the customer request, wherein the amplification reaction yields a detectable amount of an amplicon of no more than about 800, 700, 600, 500, 400, 300, 200, 150, or 100 bases of 16S rRNA using a single primer pair and single probe, and further wherein amplification of 1 pg-5 pg of DNA from any one of the at least five genera has a $C_T$ of less than 30; and generating a report that contains results for detection of a signal intensity produced by the probe.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A and 6B illustrate results of a sample analysis of hybridization between primers and probes described by Liu et al.

DETAILED DESCRIPTION OF THE INVENTION

Figure 1:
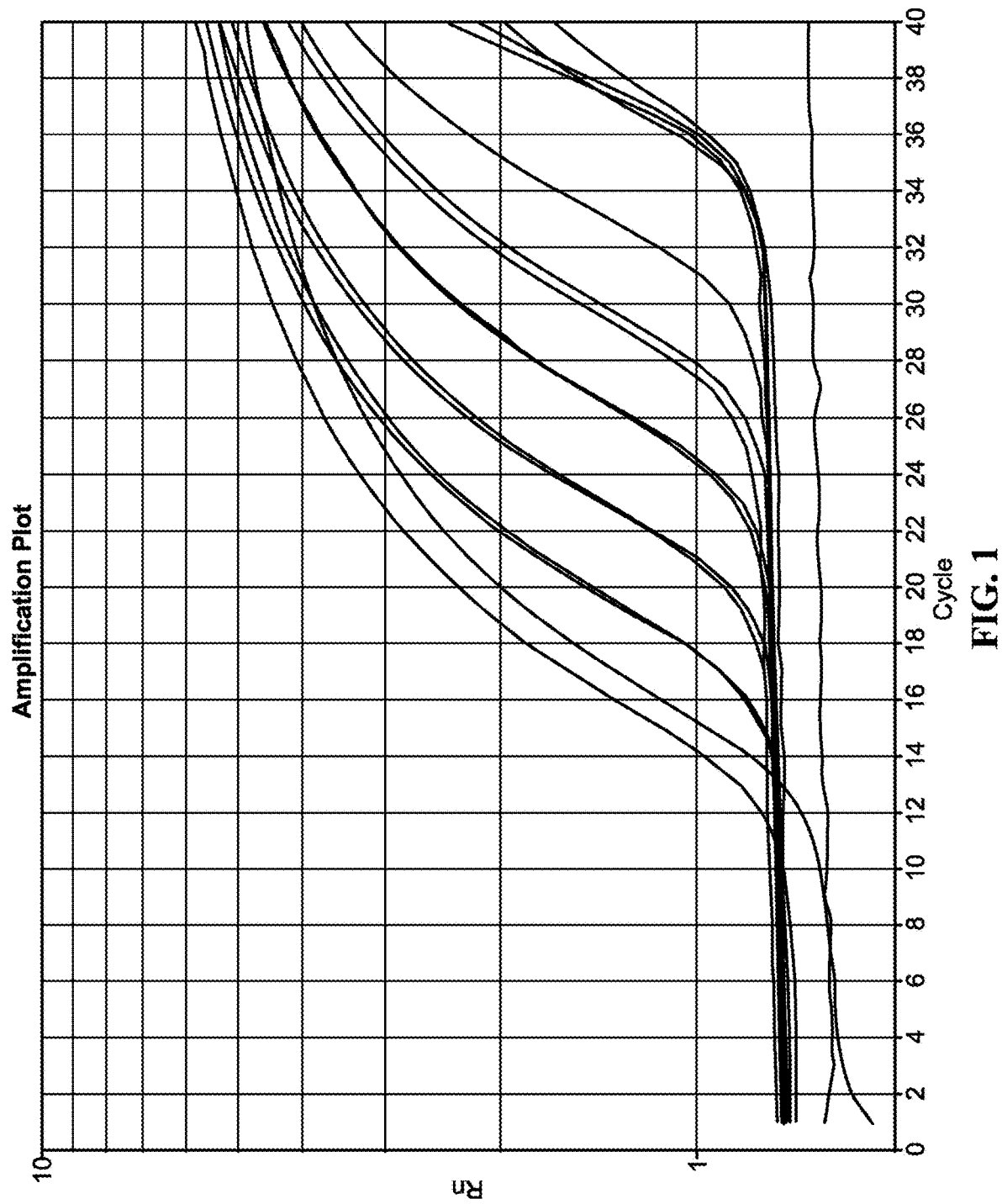
FIG. 1 is a graph illustrating results of nucleic acid amplification reactions.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

As used in the specification and claims, the singular form "a", "an" and "the" include plural references unless the context clearly dictates otherwise. For example, the term "a cell" includes a plurality of cells, including mixtures thereof.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction.

In general, a "nucleotide probe," "probe," or "tag oligonucleotide" refers to a polynucleotide used for detecting or identifying its corresponding target polynucleotide in a hybridization reaction by hybridization with a corresponding target sequence. Thus, a nucleotide probe is hybridizable to one or more target polynucleotides. Tag oligonucleotides can be perfectly complementary to one or more target polynucleotides in a sample, or contain one or more nucleotides that are not complemented by a corresponding nucleotide in the one or more target polynucleotides in a sample.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the enzymatic cleavage of a polynucleotide by an endonuclease. A sequence capable of hybridizing with a given sequence is referred to as the "complement" of the given sequence.

The term "hybridizable" as applied to a polynucleotide refers to the ability of the polynucleotide to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. The hybridization reaction may constitute a step in a more extensive process, such as the initiation of a PCR reaction, or the enzymatic cleavage of a polynucleotide by a ribozyme. A sequence hybridized with a given sequence is referred to as the "complement" of the given sequence.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "platelet sample" and "platelet concentrate" are used interchangeably to refer to a biological sample of a subject comprising platelets derived from a platelet purification process. Platelets can be purified away from one or more other blood components by a variety of methods, such as by centrifugation or aphaeresis. Such purified platelets may subsequently be combined, diluted, divided, or further purified, all of which produce samples comprising platelets derived from a platelet purification process.

In one aspect, the disclosure provides a method of detecting bacterial contamination of a platelet sample by any of a plurality of bacterial species, such as at least eight bacterial species. In one embodiment, the method comprises subjecting the sample or a portion thereof to a nucleic acid amplification reaction under conditions to yield a detectable amount of an amplicon of no more than about 800, 700, 600, 500, 400, 300, 200, 150, or 100 bases in a single reaction mixture, said reaction mixture comprising a single primer pair and a single detectable probe, wherein the primer pair flanks the amplicon, the amplicon comprises a conserved sequence to which the detectable probe hybridizes, and the conserved sequence is identical among the at least eight bacterial species; and detecting hybridization to the amplicon by the probe, wherein the hybridization by the probe yields a detectable signal indicative of bacterial contamination of the platelet sample by any of the at least eight bacterial species.

In another aspect, the disclosure provides a method of detecting bacterial contamination of a platelet sample. In one embodiment, the method comprises subjecting the sample or a portion thereof to a nucleic acid amplification reaction under conditions to yield a detectable amount of an amplicon of no more than about 800, 700, 600, 500, 400, 300, 200, 150, or 100 bases in a single reaction mixture, said reaction mixture comprising a single primer pair and a single detectable probe, wherein the primer pair flanks the amplicon, the amplicon comprises a conserved sequence to which the detectable probe hybridizes, and the sample or portion thereof has not been cultured at a temperature above 35° C. prior to amplification; and detecting hybridization to the amplicon by the probe, wherein the hybridization by the probe yields a detectable signal indicative of bacterial contamination of the platelet sample.

In one aspect, the disclosure provides a method of rapidly detecting bacterial contamination in a platelet sample within 24 hours after obtaining the sample. In one embodiment, the method comprises subjecting the sample or a portion thereof to a nucleic acid amplification reaction with a single primer pair and a single detectable probe in a single reaction mixture under conditions to yield a detectable amount of an amplicon of no more than about 800, 700, 600, 500, 400, 300, 200, 150, or 100 bases, wherein the primer pair flanks the amplicon, the amplicon comprises a conserved sequence to which the detectable probe hybridizes, and amplification of about 1 pg-5 pg of DNA from any one of the species has a cycle threshold value ($C_T$) of less than 30; and within about 24 hours after obtaining said sample, detecting hybridization to said amplicon by said probe, wherein said hybridization by said probe yields a detectable signal indicative of bacterial contamination of the platelet sample, thereby detecting the contamination within about 24 hours from obtaining said sample.

In another aspect, the disclosure provides a method of detecting bacterial contamination by any of a plurality of bacterial species from different genera in a biological sample of a subject. In one embodiment, the method comprises performing a nucleic acid amplification reaction on the sample or a portion thereof with a single primer pair to yield a detectable amount of an amplicon of no more than about 800, 700, 600, 500, 400, 300, 200, 150, or 100 bases of a 16S rRNA polynucleotide, wherein amplification of about 1 pg-5 pg of DNA from any one of the species has a cycle threshold value ($C_T$) of less than 30; and detecting the amplicon with one or more detectable probes, wherein each of the one or more detectable probes specifically hybridizes to a conserved sequence, and the conserved sequence is identical among a plurality of bacterial species from different genera.

In any of the various aspects, nucleic acids may be derived from a variety of sample sources. Nucleic acids may optionally, but not necessarily, be isolated and/or purified before further manipulation, such as in a nucleic acid amplification reaction. For example, a biological sample may be subjected to a polymerase chain reaction (PCR) procedure without a separate extraction step, such that cell-free nucleic acids are amplified from an unpurified sample. As a further example, a sample may be subjected to cell lysis conditions, either immediately before or during a nucleic acid amplification reaction, without purifying the nucleic acids away from other cellular components. In some embodiments, nucleic acids (e.g. DNA, RNA, or both) are purified from a biological sample before subjecting the nucleic acid to an amplification reaction. Various methods of nucleic acid purification are known in the art, and may vary with the type of biological sample. For example, biological samples may include tissue and/or fluid from a subject. In general, a biological fluid includes any treated or untreated fluid associated with living organisms, including, but not limited to, blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid or a cryoprotective fluid; and platelets separated from plasma and resuspended in physiological fluid or a cryoprotective fluid. Other non-limiting examples of biological samples include skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, micropiota, meconium, breast milk, and/or other excretions or body tissues. In some embodiments, the sample to be tested is whole blood. In some embodiments, the sample to be tested is buffy coat. In some embodiments, the tissue analyzed is a portion of a tissue to be transplanted or surgically grafted, such as an organ (e.g. heart, kidney, liver, lung, etc.), skin, bone, nervous tissue, tendons, blood vessels, fat, cornea, blood, or a blood component. In some embodiments, the sample is from a subject, such as a mammal, including but not limited to murines, simians, humans, farm animals, sport animals, or pets. In some embodiments, detection of contamination in the sample is the basis for medical action, such as making a diagnosis or treating the subject. For example, contamination may be diagnostic or predictive of sepsis in the subject. Corrective medical intervention, such as administering a therapeutic agent, may be taken.

In some embodiments, the sample to be tested is a platelet sample. Methods for purifying platelets away from other components of whole blood are known in the art, including methods utilizing centrifugation and/or filtration (e.g.

apheresis). When separated as a component of whole blood, platelets can be concentrated, re-suspended in plasma and/or platelet additive solutions, leukoreduced by passage through a filtration device, and/or stored in platelet storage bags kept on flatbed at a temperature of about 22° C. A platelet sample may comprise a pool of platelet samples from separate purification procedures, or portions thereof. In some embodiments, a platelet sample is a portion of a sample of purified platelets from which platelets have been removed, such as by centrifugation.

Nucleic acids may be extracted from a biological sample using any suitable method known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles (e.g. beads) to which nucleic acids can specifically or non-specifically bind, followed by isolation of the particles using a magnet, and washing and eluting the nucleic acids from the particles (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA (including but not limited to mRNA, rRNA, tRNA), or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after subsequent manipulation, such as to remove excess or unwanted reagents, reactants, or products.

In any of the various aspects, a nucleic acid amplification reaction can involve any of a variety of methods for nucleic acid amplification. In general, "amplification" refers to any process by which the copy number of a target sequence is increased. Numerous amplification-based methods for the detection and quantification of target nucleic acids are known in the art. The polymerase chain reaction (PCR) uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from RNA, and the cDNA is then amplified by PCR to produce multiple copies of DNA (see e.g. U.S. Pat. Nos. 5,322,770 and 5,310,652).

Amplification methods may involve changes in temperature (such as in a heat denaturation step), or may be isothermal processes that do not include a heat denaturation step. An example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemi-modified restriction endonuclease recognition site, and polymerase-mediated primer extension from the 3'-end of the nick to displace an existing strand and produce a strand for the next round of primer annealing, nicking, and strand displacement, resulting in geometric amplification of product (see e.g., U.S. Pat. Nos. 5,270,184 and 5,455,166). Thermophilic SDA (tSDA) uses thermophilic endonucleases and polymerases at higher temperatures in essentially the same method (European Pat. No. 0684315).

Other examples of amplification methods include rolling circle amplification (RCA) (e.g., Lizardi, "Rolling Circle Replication Reporter Systems," U.S. Pat. No. 5,854,033); helicase dependent amplification (HDA) (e.g. U.S. Pat. Appl. US 20040058378), and loop-mediated isothermal amplification (LAMP) (e.g., Notomi et al., "Process for Synthesizing Nucleic Acid," U.S. Pat. No. 6,410,278).

Further examples of nucleic acid amplification reactions include transcription-based amplification methods such as nucleic acid sequence based amplification, also referred to as NASBA (e.g., Malek et al., U.S. Pat. No. 5,130,238); methods which rely on the use of an RNA replicase to amplify the probe molecule itself, commonly referred to as Qβ replicase (e.g., Lizardi, P. et al. (1988) *BioTechnol.* 6, 1197-1202); and self-sustained sequence replication (e.g., Guatelli, J. et al. (1990) *Proc. Natl. Acad. Sci. USA* 87, 1874-1878; Landgren (1993) *Trends in Genetics* 9, 199-202; and HELEN H. LEE et al. NUCLEIC ACID AMPLIFICATION TECHNOLOGIES (1997)). Another transcription-based amplification method is transcription-mediated amplification, commonly referred to as TMA, which synthesizes multiple copies of a target nucleic acid sequence autocatalytically under conditions of substantially constant temperature, ionic strength, and pH, in which multiple RNA copies of the target sequence autocatalytically generate additional copies (see e.g., U.S. Pat. Nos. 5,480,784; and 5,399,491). Additional examples of nucleic acid amplification methods include ligase chain reaction (see e.g. U.S. Pat. Nos. 5,494,810 and 5,830,711), and solid-phase amplification methods (e.g. bridge amplification with primers attached to a solid surface, such as a slide or a bead; see e.g. U.S. Pat. Nos. 5,641,658 and 7,985,565).

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to as a "nicking enzyme" or a "nicking endonuclease." The SDA primer then hybridizes to the target sequence. The SDA reaction mixture also contains a polymerase (an "SDA polymerase") and a mixture of all four deoxynucleoside-triphosphates (also called deoxynucleotides or dNTPs, i.e. dATP, dTTP, dCTP and dGTP, commonly used in primer extension reactions), at least one species of which is a substituted or modified dNTP; thus, the SDA primer is extended, to form a modified primer, sometimes referred to as a "newly synthesized strand." The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'→3' exonuclease activity. However, if less than all the nucleotides are substituted, the polymerase preferably lacks 5'→3' exonuclease activity. As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are known in the art including but not limited to HincII, HindII, AvaI, Fnu4HI, TthIIII, NcII, BstXI, BamHI, etc. A chart depicting suitable enzymes, and their corresponding recognition sites and the modified dNTP to use is found in U.S. Pat. No. 5,455,166, hereby incorporated by reference. Once nicked, a polymerase (an "SDA polymerase") is used to extend the newly nicked strand, 5'→3', thereby creating another newly synthesized strand. The polymerase chosen should be able to initiate 5'→3' polymerization at a nick site, should also displace the polymerized strand downstream from the nick, and should lack 5'→3'-exonuclease activity (this may be additionally accomplished by the addition of a blocking agent). Suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase. In general, SDA does not require thermocycling. The temperature of the reaction is generally set to be high enough to prevent non-specific hybridization but low enough to allow specific hybridization; this is typically from about 37° C. to about 42° C., depending on the enzymes. In some embodiment, as for other amplification techniques described herein, a second primer extension reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands. Accordingly, amplification may be linear or non-linear (e.g. exponential).

NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. A main difference between NASBA and TMA is that NASBA utilizes the addition of RNAse H to effect RNA degradation, and TMA relies on inherent RNAse H activity of a reverse transcriptase. In general, these techniques may be described as follows. A single stranded target nucleic acid, usually an RNA target sequence (sometimes referred to as "the first target sequence" or "the first template"), is contacted with a first primer, generally referred to herein as a "NASBA primer" (although "TMA primer" is also suitable). Starting with a DNA target sequence is described below. These primers generally have a length of 25-100 nucleotides, with NASBA primers of approximately 50-75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (a "NASBA reverse transcriptase") and a mixture of the four dNTPs, such that the first NASBA primer is extended, to form a modified first primer, comprising a hybridization complex of RNA (the first template) and DNA (the newly synthesized strand). By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myeloblastosis virus reverse transcriptase ("AMV RT") and the Moloney murine leukemia virus RT. When the amplification reaction is TMA, the reverse transcriptase enzyme further comprises a RNA degrading activity. In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from E. coli and calf thymus. The ribonuclease activity degrades the first RNA template in the hybridization complex, resulting in a disassociation of the hybridization complex leaving a first single stranded newly synthesized DNA strand, sometimes referred to as "the second template." In addition, the NASBA reaction also includes a second NASBA primer, generally comprising DNA (although as for all the probes and primers herein, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. The antisense promoter and transcription initiation site can be that of the T7 RNA polymerase, although other RNA polymerase promoters and initiation sites can be used as well. The second primer hybridizes to the second template, and a DNA polymerase, also termed a "DNA-directed DNA polymerase," also present in the reaction, synthesizes a third template (a second newly synthesized DNA strand), resulting in second hybridization complex comprising two newly synthesized DNA strands. Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage φII, *Salmonella* phage sp6, or *Pseudomonas* phage gh-1. In some embodiments, TMA and NASBA are used with starting DNA target sequences, a first primer comprising the RNA polymerase promoter, and a DNA polymerase enzyme to generate a double stranded DNA hybrid with the newly synthesized strand comprising the promoter sequence. The hybrid is then denatured and the second primer added.

Another example of an isothermal amplification reaction is Single Primer Isothermal Amplification (SPIA). This amplification technique is disclosed in WO2001020035 and U.S. Pat. No. 6,251,639, which are incorporated by reference herein. Generally, the method includes hybridizing chimeric RNA/DNA amplification primers to the probes or target. Preferably the DNA portion of the probe is 3' to the RNA. Optionally, the method includes hybridizing a polynucleotide comprising a termination polynucleotide sequence to a region of the template that is 5' with respect to hybridization of the composite primer to the template. Following hybridization of the primer to the template, the primer is extended with DNA polymerase. Subsequently, the RNA is cleaved from the composite primer with an enzyme that cleaves RNA from an RNA/DNA hybrid. Subsequently, an additional RNA/DNA chimeric primer is hybridized to the template such that the first extended primer is displaced from the target probe. The extension reaction is repeated, whereby multiple copies of the probe sequence are generated. When only one SPIA primer is used, the amplification reaction proceeds linearly. When a reverse SPIA primer with complementarity to the first primer extension product is also used, the amplification reaction is non-linear.

In some embodiments, the nucleic acid amplification reaction is a PCR reaction. Conditions favorable to the amplification of target sequences by PCR can be determined by methods known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 2, 3, 4, 5, 6, 7, 8, 9, 10 or more steps, and cycled steps may be preceded and/or followed by one or more steps not included in those steps that are cycled (e.g. an initial melting step or a final incubation step). Steps can comprise any temperature or gradient of temperatures, suitable for achieving the purpose of the given step, including but not limited to, primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles.

In some embodiments of any of the various aspects, the nucleic acid amplification reaction comprises 3'-end extension of one or more primers, e.g. about, more than about, or less than about 1, 2, 3, 4, 5, 6, 7, 8, 9, 10, or more primers. In some embodiments, primer extension in the nucleic acid amplification reaction involves only one pair of primers. In other embodiments, primer extension in the nucleic acid amplification reaction involves multiple pairs of primers, such as 2, 3, 4, 5, or more primer pairs. In some embodiments, a pair of primers consists of a first primer and a second primer, wherein the first primer comprises a sequence that is hybridizable to at least a portion of one or more target polynucleotides, and further wherein the second primer comprises a sequence that is hybridizable to at least a portion of the complement of a first primer extension product. When the target polynucleotide is double-stranded, the sequence of the second primer that is hybridizable to at least a portion of the complement of a first primer extension product may also be hybridizable to at least a portion of the complementary strand of the target polynucleotide. When an amplification reaction contains a plurality of primer pairs, the plurality of primer pairs may be distinct (as in two different primers for each pair), overlapping (such as one forward primer paired with two or more different reverse primers), or combinations of distinct pairs and overlapping pairs. An amplification primer can be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). Typically, when a primer comprises a complementary portion and a non-complementary portion, the portion that is complementary to a target sequence is located at the 3'-end of the primer. Primer pairs can be designed to amplify a target sequence of any desired length. As used herein, "amplicon" refers to the target sequence that is amplified from the target polynucleotide in the nucleic acid amplification reaction, in single- or double-stranded form. When an amplicon is amplified by a pair of primers, the amplicon is generally flanked by the pair of primers, such that one primer hybridizes at the 5' end of the target sequence and the other primer hybridizes to the complement of the 3' end of the target sequence. In some embodiments, the amplicon is about, or less than about 1000, 900, 800, 700, 600, 500, 400, 300, 250, 200, 175, 150, 125, 100, 90, 80, 70, 60, 50, 40, 30, 25, or fewer nucleotides in length. In some embodiments, the amplicon is about, or more than about, 50, 100, 200, 300, 400, 500, 750, 1000, or more nucleotides in length. In some embodiments, amplicon length is between any two of these endpoints, such as 25-1000, 30-500, 50-400, 50-250, 50-150, or 100-200 nucleotides in length. Primers may be selected based on conformance to any of a variety of design considerations, which may be used alone or in combination with any other design consideration disclosed herein or known in the art. Additional non-limiting examples of optional design considerations for primers include: avoiding runs of the same nucleotide (e.g. 3, 4, 5, or more of the same nucleotide in a row); proximity to the probe without overlapping probe hybridization site (e.g. about or less than about 0, 1, 2, 3, 4, 5, 6, 7, 8, 9, 10, 15, 25, 30, 40, 50, 75, 100, or more nucleotides between the 3' end of a primer and the 5' end of a probe along the same strand); G-C content within about 20%-80%, melting temperature ($T_m$) within a selected range (e.g. about 55-65° C., 58-62° C., or 58-60° C.); having no more than two G and/or C bases within the last five nucleotides at the 3' end; primers in a pair having similar $T_m$ (e.g. the same $T_m$, or $T_m$'s within about 1-2° C. of each other); minimal secondary structure (e.g. about or fewer than about 5, 4, 3, 2, or 1 Watson-Crick paired bases when optimally folded, such as by analysis with mFold (see e.g. Zuker et al., Nucl. Acid Res, 2003, 31: 3406-3415)); minimal hybridization between primers in a reaction as homodimers or heterodimers (e.g. about or fewer than about 10, 9, 8, 7, 6, 5, 4, 3, 2, or 1 Watson-Crick paired bases when optimally aligned); and minimal hybridization between a primer and corresponding probe (e.g. about or fewer than about 10, 9, 8, 7, 6, 5, 4, 3, 2, or 1 Watson-Crick paired bases when optimally aligned). In some embodiments, primers specifically amplify amplicons that are about or at least about 25, 50, 75, 100, 125, 150, or 175 nucleotides in length, and have about or at least about 80%, 85%, 90%, 95%, 97.5%, 99%, 99.5%, or more sequence identity with a sequence in Table 1 (or a complement thereof) when optimally aligned. Methods and algorithms for determining optimal sequence alignment are known in the art, any of which may be used to determine percent sequence identity. One example of an algorithm for determining sequence identity between two sequences includes the Basic Local Alignment Search Tool (BLAST), as maintained by the National Center for Biotechnology Information at blast.ncbi.nlm.nih.gov.

In some embodiments, primer pairs are immobilized on a solid support. Examples of solid supports include, but are not limited to, inorganic materials such as silica based substrates (e.g. glass, quartz, fused silica, silicon, or the like), other semiconductor materials, and organic materials such as polymer materials (e.g. polymethylmethacrylate, polyethylene, polypropylene, polystyrene, cellulose, agarose, or any of a variety of organic substrate materials conventionally used as supports for reactive media). In addition to the variety of materials useful as solid supports, solid support structures may be in any of a variety of physical configurations, including but not limited to microparticles, beads, nanoparticles, nanocrystals, fibers, microfibers, nanofibers, nanowires, nanotubes, mats, planar sheets, planar wafers or slides, multiwell plates, optical slides including additional structures, capillaries, microfluidic channels, and the like. In some embodiments, amplification on a solid support comprises bridge amplification. General methods of bridge amplification are known in the art. See for example WO/1998/044151 and WO/2000/018957.

Of particular interest are primer sequences capable of specific hybridization to regions conserved amongst at least 5, 10, 15, 20 or more different bacterial genomes. For example, a forward and a reverse primer each hybridizes to a separate region that is conserved amongst at least 5, 10, 15, 20 or more different bacterial genomes are selected. These conserved regions include but not limited to from 9 to 28, from 32 to 48, from 522 to 545, from 888 to 903, from 916 to 937, from 939 to 973, from 975 to 994, from 957 to 981, from 1093 to 1125, from 1184 to 1206, from 1231 to 1252, from 1378 to 1396, from 1398 to 1422, or from 1496 to 1516 of 16S rRNA of *Staphylococcus aureus* (GenBank accession Number NC_007622) or the corresponding regions in any one of the bacterial genomes: *Staphylococcus aureus* Mu3; *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Serratia marcescens, Bacillus cereus, Propionibacterium* sp., *Staphylococcus aureus* Mu50, *Yersinia enterocolitica, Staphylococcus simulans, Micrococcus luteus*, and *Enterobacter aerogenes*.

In some embodiments, the subject primers are capable of specific hybridization to conserved regions of at least 5, 10, 15, 20 or more different bacterial genomes, and hence allow specific amplification and detection of any type of the at least 5, 10, 15, 20 or more different bacterial genomes. The design of such primers and sets thereof allows for simultaneous determination of bacterial infection across a wide set of bacterial strains. In some embodiment, such detection occurs in a single amplification reaction with a single pair of primers, and optionally with one or more optional primers to provide additional bacterial coverage. These primers and sets thereof can be used in conjunction with probes disclosed herein or other labeling molecules such as DNA-binding dyes (e.g., SYBR® Green) and the like.

Primer extension in a nucleic acid amplification reaction can be carried out by any suitable polymerase known in the art, such as a DNA polymerase, many of which are commercially available. DNA polymerases can comprise DNA-dependent DNA polymerase activity, RNA-dependent DNA polymerase activity, or DNA-dependent and RNA-dependent DNA polymerase activity. DNA polymerases can be thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEP-VENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof. In some embodiments, enzymes produced using bacteria are highly purified, such that a no-template control amplification reaction does not produce an amplification signal above background levels after about, or more than about 25, 30, 35, 40, 45, or more cycles of a PCR reaction.

In some embodiments of any of the various aspects, nucleic acid amplification products are detected during and/or at the completion of the amplification process. Amplification product detection can be conducted in real time in an amplification assay. In some embodiments, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems. Non-limiting examples of DNA-binding dyes include SYBR® green, SYBR blue, DAPI, propidium iodine, Hoechst, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In some embodiments, sequence specific oligonucleotide probes are employed in the nucleic acid amplification reaction to facilitate the detection and/or quantification of the amplified products. Probe-based quantitative amplification relies on the sequence-specific detection of a desired amplified product, such as by specific hybridization between a probe and a target sequence within an amplification product. Examples of target-specific probes include, without limitation, TaqMan® probes and molecular beacons. Generic methods for performing probe-based quantitative amplification are known in the art (see e.g. U.S. Pat. No. 5,210,015). Hybridization can be performed under various stringencies. Suitable hybridization conditions are generally such that the recognition interaction between the probe and target polynucleotide is both sufficiently specific and sufficiently stable as to provide preferential hybridization between an oligonucleotide probe and/or primer and the intended target sequence. Conditions that increase the stringency of a hybridization reaction are known in the art, and include optimization of annealing temperature and/or salt concentration. An oligonucleotide probe can be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). In some embodiments, a plurality of probes are used in a single nucleic acid amplification reaction, such as about or less than about 2, 3, 4, 5, 6, 7, 8, 9, 10, 15, 20, 25, or more probes. In some embodiments, a single nucleic acid amplification reaction contains only two probes, such as one that specifically hybridizes to a sequence from one or more Gram-positive bacteria (e.g. about or more than about 1, 2, 3, 4, 5, 6, 7, 8, 9, 10, or more) and a second that specifically hybridizes to a sequence from one or more Gram-negative bacteria (e.g. about or more than about 1, 2, 3, 4, 5, 6, 7, 8, 9, 10, or more). In some embodiments, a single nucleic acid amplification reaction contains only one probe, such as a probe that specifically hybridizes to a sequence that is identical among a plurality of different bacterial species (e.g. about or more than about 2, 3, 4, 5, 6, 7, 8, 9, 10, 11, 12, 13, 14, 15, 16, 17, 18, 19, 20, 25, 30, 40, 50, or more species) and/or identical among bacteria from a plurality of different genera (e.g. about or more than about 2, 3, 4, 5, 6, 7, 8, 9, 10, 11, 12, 13, 14, 15, 16, 17, 18, 19, 20, 25, 30, 40, 50, or more genera). Probes may be selected based on conformance to any of a variety of design considerations, which may be used alone or in combination with any other design consideration disclosed herein or known in the art. Additional non-limiting examples of optional design considerations for probes include: avoiding runs of the same nucleotide (e.g. 3, 4, 5, or more of the same nucleotide in a row); proximity to an amplification primer hybridization site without overlapping (e.g. about or less than about 0, 1, 2, 3, 4, 5, 6, 7, 8, 9, 10, 15, 25, 30, 40, 50, 75, 100, or more nucleotides between the 3' end of a primer and the 5' end of a probe along the same strand); G-C content within about 20%-80%, melting temperature ($T_m$) within a selected range (e.g. about 8-10° C. higher than a corresponding primer $T_m$); and having more C's than G's; no G on the 5' end. In some embodiments, a probe specifically hybridizes to amplicons that are about or at least about 25, 50, 75, 100, 125, 150, or 175 nucleotides in length, and have about or at least about 80%, 85%, 90%, 95%, 97.5%, 99%, 99.5%, or more sequence identity with a sequence in Table 1 when optimally aligned. Methods and algorithms for determining optimal sequence alignment are known in the art, any of which may be used to determine percent sequence identity. One example of an algorithm for determining sequence identity between two sequences includes the Basic Local Alignment Search Tool (BLAST), as maintained by the National Center for Biotechnology Information at blast.ncbi.nlm.nih.gov.

For a convenient detection of the probe-target complexes formed during the hybridization assay, the nucleotide probes can be conjugated to a detectable label. Suitable detectable labels can include any composition detectable by photochemical, biochemical, spectroscopic, immunochemical, electrical, optical, or chemical means. A wide variety of appropriate detectable labels are known in the art, which include fluorescent labels, chemiluminescent labels, radioactive isotope labels, enzymatic labels, and ligands. The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. In some embodiments, each of a plurality of probes in a single reaction is conjugated to a different detectable label (e.g. fluorescent dyes with different emission spectra), such that signal corresponding to amplification of different targets can be differentiated. Enzymatic labels are typically detected by providing the enzyme with a substrate and measuring the reaction product produced by the action of the enzyme on the substrate; and finally colorimetric labels are detected by simply visualizing the colored label.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. A sequence-specific probe is included in the PCR reaction. A typical TaqMan probe is an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter. A variety of reporter-quencher pairs are known in the art. Some pairs interact through fluorescence resonance energy transfer (FRET). Molecules commonly used in FRET as reporters or quenchers include, but are not limited to, fluorescein dyes (e.g., FAM, JOE, and HEX), rhodamine dyes (e.g, R6G, TAMRA, ROX), cyanine dyes (e.g, Cy3, Cy3.5, Cy5, Cy5.5, and Cy7), DABCYL, and EDANS. Whether a fluorescent dye acts as a reporter or a quencher is defined by its excitation and emission spectra, and by the fluorescent dye with which it is paired. For example, FAM is most efficiently excited by light with a wavelength of 488 nm, and emits light with a spectrum of 500 to 650 nm, and an emission maximum of 525 nm. FAM is a suitable reporter label for use with, e.g., TAMRA as a quencher, which has its excitation maximum at 514 nm. Examples of non-fluorescent or dark quenchers that dissipate energy absorbed from a fluorescent dye include the Black Hole Quenchers™ marketed by Biosearch Technologies, Inc, (Novato, Calif., USA). The Black Hole Quenchers™ are structures comprising at least three radicals selected from substituted or unsubstituted aryl or heteroaryl compounds, or combinations thereof, wherein at least two of the residues are linked via an exocyclic diazo bond (see, e.g., International Publication No. WO2001086001). Other dark quenchers include Iowa Black quenchers (e.g., Iowa Black FQ™ and Iowa Black RQ™), Eclipse® Dark Quenchers (Epoch Biosciences, Inc, Bothell, Wash.), and Zen™ quenchers (Integrated DNA Technologies, Inc.; Coralville, Iowa). Additional non-limiting examples of quenchers are also provided in U.S. Pat. No. 6,465,175.

In some embodiments, hybridization of a bound probe is detected using a molecular beacon oligonucleotide probe, such as described in U.S. Pat. No. 5,925,517, PCT Application No. WO1995013399, and U.S. Pat. No. 6,150,097. In a typical molecular beacon, a central target-recognition sequence is flanked by arms that hybridize to one another when the probe is not hybridized to a target strand, forming a hairpin structure, in which the target-recognition sequence is in the single-stranded loop of the hairpin structure, and the arm sequences form a double-stranded stem hybrid. When the probe hybridizes to a target, a relatively rigid helix is formed, causing the stem hybrid to unwind and forcing the arms apart. A FRET pair, such as the fluorophore EDANS and the quencher DABCYL (or other pairs described herein or known in the art), may be attached to the arms by alkyl spacers. When the molecular beacon is not hybridized to a target strand, the fluorophore's emission is quenched. When the Molecular Beacon is hybridized to a target strand, the FRET pair is separated, and the fluorophore's emission is not quenched. Emitted fluorescence signals the presence of target strands. Signal can be detected during a nucleic acid amplification reaction, such as with a fluorimeter at the end of each cycle in a PCR reaction. Signal intensity increases with an increasing amount of target sequence.

As disclosed in Whitcombe et al., Detection Of PCR Products Using Self-probing Amplicons and Fluorescence, Nature Biotechnology 17: 804-807 (August 1999), detection of PCR products may be accomplished with self-probing amplicons. A Scorpion Primer carries a 5' extension comprising a probe element, a pair of self-complimentary stem sequences, and a fluorophore/quencher pair. The extension is "protected" from being copied by the inclusion of a blocking hexethylene glycol (HEG) monomer. After a round of PCR extension from a primer, a newly synthesized target region is now attached to the same strand as the probe. Following a second round of denaturation and annealing, the probe and target hybridize, the probe subsequently fluorescing. Accordingly, a "probe" as described herein, may be present as a portion of a primer.

In some embodiments of any of the various aspects, a target sequence amplified in the nucleic acid amplification reaction is the sequence of a portion of a conserved bacterial polynucleotide. In some embodiments, an amplified portion of a conserved polynucleotide exhibits about or more than about 80%, 85%, 90%, 95%, 97.5%, or higher homology across different bacterial genera. Examples of conserved polynucleotide sequences include, but are not limited to, nucleotide sequences found in the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, cox1 gene and nifD gene. In some embodiments, the conserved polynucleotide is a portion of a 16S rRNA polynucleotide (e.g. rRNA, rDNA, amplification product, or combination of these). A listing of almost 40,000 aligned 16S rDNA sequences greater than 1250 nucleotides in length can be found on the Greengenes web application, a publicly accessible database run by Lawrence Berkeley National Laboratory. Other publicly accessible databases include GenBank, Michigan State University's ribosomal database project, the Max Planck Institute for Marine Microbiology's Silva database, and the National Institute of Health's NCBI. Non-limiting examples of amplification target sequences are shown in Table 1. In some embodiments, an amplicon is about or at least about 25, 50, 75, 100, 125, 150, or 175 nucleotides in length, and has about or at least about 80%, 85%, 90%, 95%, 97.5%, 99%, 99.5%, or more sequence identity with a sequence in Table 1 when optimally aligned. Methods and algorithms for determining optimal sequence alignment are known in the art, any of which may be used to determine percent sequence identity. One example of an algorithm for determining sequence identity between two sequences includes the Basic Local Alignment Search Tool (BLAST), as maintained by the National Center for Biotechnology Information at blast.ncbi.nlm.nih.gov.

In some embodiments, a portion of a conserved polynucleotide is specifically amplified by a pair of primers consisting of a first primer and a second primer that are specifically hybridizable to a sequence that is identical among a plurality of different bacterial species (e.g. about or more than about 2, 3, 4, 5, 6, 7, 8, 9, 10, 11, 12, 13, 14, 15, 16, 17, 18, 19, 20, 25, 30, 40, 50, or more) and/or identical among bacteria from a plurality of different genera (e.g. about or more than about 2, 3, 4, 5, 6, 7, 8, 9, 10, 11, 12, 13, 14, 15, 16, 17, 18, 19, 20, 25, 30, 40, 50, or more). Amplification with a single pair of universal primers can thus amplify polynucleotides from a plurality of different organisms in a single reaction. In some embodiments, a primer pair comprises a first primer comprising at least about 10, 11, 12, 13, 14, 15, 16, 17, 18, 19, 20, 25, or more contiguous nucleotides from a sequence in Table 1 at its 3'-end, and a second primer comprising the complement of least about 10, 11, 12, 13, 14, 15, 16, 17, 18, 19, 20, 25, or more contiguous nucleotides from the same Table 1 sequence at its 3'-end. In some embodiments, one or more primers in a nucleic acid amplification reaction comprise at least about 10, 11, 12, 13, 14, 15, or all nucleotides of a sequence selected from Table 2 at their 3'-ends. In some embodiments, a first primer comprising at least about 10 nucleotides from SEQ ID NO: 4 at its 3' end is used in combination with a second primer comprising at least about 10 nucleotides from SEQ ID NO: 5 or 6 at its 3' end. In some embodiments, a first primer comprising at least about 10 nucleotides from SEQ ID NO: 7 at its 3' end is used in combination with a second primer comprising at least about 10 nucleotides from SEQ ID NO: 8 at its 3' end. In some embodiments, a first primer comprising at least about 10 nucleotides from SEQ ID NO: 9 at its 3' end is used in combination with a second primer comprising at least about 10 nucleotides from SEQ ID NO: 10 at its 3' end.

In some embodiments of the various aspects, the presence, absence, and/or quantity of a plurality of organisms are detected in a single reaction. In some embodiments, the organisms detected are microorganisms, non-limiting examples of which include viruses, viroids, bacteria, archaea, fungi, and protozoa. In some embodiments, the microorganisms are bacteria. The bacteria detected may be Gram-positive, Gram-negative, or combinations of Gram-positive and Gram-negative bacteria. Non-limiting examples of bacteria that may be detected in a single reaction include two or more (e.g. 2, 3, 4, 5, 6, 7, 8, 9, 10, or more) of *Staphylococcus aureus*, *Staphylococcus aureus* Mu3; *Staphylococcus epidermidis*, *Streptococcus agalactiae*, *Streptococcus pyogenes*, *Streptococcus pneumonia*, *Escherichia coli*, *Citrobacter koseri*, *Clostridium perfringens*, *Enterococcus faecalis*, *Klebsiella pneumonia*, *Lactobacillus acidophilus*, *Listeria monocytogenes*, *Propionibacterium granulosum*, *Pseudomonas aeruginosa*, *Serratia marcescens*, *Bacillus cereus*, *Staphylococcus aureus* Mu50, *Yersinia enterocolitica*, *Staphylococcus simulans*, *Micrococcus luteus*, and *Enterobacter aerogenes*. In some embodiments, all bacteria detected are detected with a single probe complementary to a sequence shared among all bacteria to be detected. The target sequence flanked and amplified by a pair of universal primers may be different among a plurality of different organisms having the conserved polynucleotide (e.g. have one or more insertion, deletion, substitution, or combinations thereof), identical among a plurality of different organisms having the conserved polynucleotide, or combinations of these. Typically, the target sequence flanked and amplified by a pair of universal primers comprises one or more conserved internal regions of nucleotide sequence that are identical among a plurality of different bacterial species (e.g. about or more than about 2, 3, 4, 5, 6, 7, 8, 9, 10, 11, 12, 13, 14, 15, 16, 17, 18, 19, 20, 25, 30, 40, 50, or more) and/or identical among bacteria from a plurality of different genera (e.g. about or more than about 2, 3, 4, 5, 6, 7, 8, 9, 10, 11, 12, 13, 14, 15, 16, 17, 18, 19, 20, 25, 30, 40, 50, or more), which conserved internal region may be used as a probe target. In some embodiments, a conserved internal region is identical among a plurality of Gram-positive bacteria and not among Gram-negative bacteria, or vice versa. In some embodiments, a conserved internal region is about, or at least about 10, 11, 12, 13, 14, 15, 16, 17, 18, 19, 20, 25, 30, 40, 50, 75, 100, or more nucleotides in length. In some embodiments, primers are selected such that the amplicon sequence among the species and/or genera to be detected is about or at least about 80%, 85%, 90%, 95%, 97.5%, 98%, 99%, 99.5%, or higher sequence identity across the species and/or genera to be detected. In some embodiments, primers are selected to produce an amplicon within a target length across the species and/or genera to be detected, such as any amplicon length described herein.

In some embodiments, a plurality of bacterial species and/or genera are detected (and optionally quantified) by hybridization between an amplified conserved internal region and a probe oligonucleotide. In general, a positive signal from a probe that specifically hybridizes to a conserved internal region is indicative of the presence of the target sequence, indicating that at least one organism having that target sequence was present in the sample from which the nucleic acids were derived. In this way, the presence, absence, and/or quantity of a plurality of species and/or genera can be detected with a common probe. In some embodiments, the probe comprises at least about 10, 11, 12, 13, 14, 15, 16, 17, 18, 19, 20, 25, or more contiguous nucleotides from a sequence in Table 1, or a sequence complementary thereto. In some embodiments, one or more probes in a nucleic acid amplification reaction comprise at least about 10, 11, 12, 13, 14, 15, or all nucleotides of a sequence selected from Table 3, or a complement thereof. In some embodiments, one or more probes comprising at least 10 nucleotides from SEQ ID NO: 11, 12, or 13 (or complements thereof) are used to detect amplification products amplified by primers based on SEQ ID NO: 4-6. In some embodiments, one or more probes comprising at least 10 nucleotides from SEQ ID NO: 14 or 15 (or complements thereof) are used to detect amplification products amplified by primers based on SEQ ID NO: 7-8. In some embodiments, a probe comprising at least 10 nucleotides from SEQ ID NO: 16 (or a complement thereof) is used to detect amplification products amplified by primers based on SEQ ID NO: 9-10.

In some embodiments of any of the various aspects, primers and probes are selected to maximize sensitivity of target polynucleotide detection. In some embodiments, sensitivity is measured in terms of cycle threshold ($C_T$) value. In the initial cycles of PCR, there is little change in fluorescence signal. This defines the baseline for an amplification plot (a plot of fluorescence intensity over cycle number). An increase in fluorescence above the baseline indicates the detection of accumulated PCR product. A fixed fluorescence threshold can be set above the baseline. The parameter $C_T$ is defined as the fractional cycle number at which the fluorescence passes the fixed threshold, typically an intensity that is statistically significant above the baseline or background and in the log-linear phase of amplification. Software for calculating the threshold level of fluorescence in a given reaction or set of reactions are typically included in real-time PCR analysis software packages. One common method for setting the threshold is determining the baseline (background) average signal and setting a threshold 10-fold higher than the baseline average signal. Alternatively, a threshold value may be set at about 10 times the standard deviation of baseline emission. A plot of the log of initial target copy number for a set of standards versus $C_T$ is typically a straight line. Quantification of the amount of target in unknown samples is accomplished by measuring $C_T$ and using the standard curve to determine starting copy number. In some embodiments, detection has a linear range of detection over about or more than about 3, 4, 5, 6, 7, 8, or more logs. In some embodiments, amplification of about or less than about 10 pg, 5 pg, 4 pg, 3 pg, 2 pg, 1 pg, 0.5 pg, 0.1 pg, or range between any of these (e.g. 0.5-4 pg, 1 pg-5 pg, 1 pg-3 pg, etc) of genomic DNA from any one of the bacterial species detectable by a probe in the amplification reaction has a $C_T$ of less than 30. In some embodiments, amplification of about or less than about 15000, 10000, 5000, 2500, 1500, 1000, 500, 200, 100, 50, or fewer starting copies of a target sequence detectable by a probe in the amplification reaction has a $C_T$ of less than 30. In some embodiments, amplification of about 1 pg of genomic DNA from any one of the bacterial species detectable by a probe in the amplification reaction has a $C_T$ of about or less than about 30, 29, 28, 27, 26, 25, or lower. In some embodiments, the $C_T$ for a negative control sample is at least 2 cycles (e.g. at least 2, 3, 4, 5, 6, 7, 8, 9, 10, or more cycles) higher than the $C_T$ for a sample containing about 100 pg, 10 pg, 5 pg, 4 pg, 3 pg, 2 pg, 1 pg, 0.5 pg, 0.1 pg, or range between any of these (e.g. 0.5-4 pg, 1 pg-5 pg, 1 pg-3 pg, 5 pg-10 pg, etc) of genomic DNA from any one of the bacterial species detectable by a probe in the amplification reaction. Typically, a negative control is an amplification reaction that has all reaction reagents, but no template is added (e.g. add water instead of template, or polynucleotides known to lack a target amplicon, such as human genomic DNA in the case of a bacteria-specific amplicon). In some embodiments, bacterial contamination is detected in nucleic acid from about or less than about 25 mL, 20 mL, 15 mL, 10 mL, 5 mL, 4 mL, 3 mL, 2 mL, 1 mL, 0.1 mL or less of a platelet concentrate. In some embodiments, amplification is performed on a platelet sample or portion thereof without first incubating the sample to promote bacterial growth, such as at a temperature above about 30° C., 35° C., or 37° C. In some embodiments, detection yields a detectable signal indicative of bacterial contamination of a platelet sample having a bacterial load of about or less than about 50, 25, 10, 5, 4, 3, 2, 1, 0.1 or fewer colony forming units per mL (CFU/mL) in a platelet sample. In some embodiments, detection yields a detectable signal indicative of bacterial contamination of a platelet sample when nucleic acids derived from fewer than 50000, 40000, 30000, 25000, 20000, 15000, 10000, 7500, 5000, 2500, 1250, 1000, 750, 500, 250, 100, 50, 25, 10, 5, or fewer CFU are present in the detection reaction. In some embodiments, a detectable signal is obtained for a reaction containing nucleic acids derived from 5 to 50000 CFU, 500 to 25000 CFU, 1000 to 10000 CFU, or 25 to 2500 CFU. In some embodiments, detection is completed prior to transfusion of a donated platelet sample, and if a positive signal is detected (indicating bacterial contamination), the donated platelets are not transfused into a recipient. In some embodiments, a positive signal for a sample having contamination at or above any of the disclosed detection thresholds is detected within about 48, 24, 12, 6, 4, 2, or fewer hours from obtaining the sample from a subject (e.g. from withdrawing blood from a subject).

In some embodiments of any of the aspects described herein, a detection procedure is initiated at a time just prior to use of the biological sample (e.g. prior to administering a blood sample or blood-derived sample, such as a platelet sample, to a subject), and yields a result prior to such use, regardless of when the sample was collected. For example, a biological sample may be tested for contamination about or less than about 12, 11, 10, 9, 8, 7, 6, 5, 4, 3, 2, or 1 hour before a planned use of the biological sample, and a detection result is obtained before the time of such planned use (e.g. 1, 2, 3, 4, 5, or more hours before use). In some embodiments, a sample is tested within about 5 hours of planned use, and a result is obtained prior to such planned use. In some embodiments, a sample is tested within about 2 hours of planned use, and a result is obtained prior to such planned use. In some embodiments, a sample is tested within about 1 hour of planned use, and a result is obtained prior to such planned use. In some embodiments, the biological sample is discarded without using it if bacterial contamination is detected by the detection method. In some embodiments, the planned use of the biological sample proceeds if bacterial contamination is not detected. In some embodiments, the sample that is tested prior to use was collected about or more than about 1, 2, 3, 4, 5, 6, 7, 8, 9, 10, or more days prior to the planned use. In some embodiments, the sample that is tested prior to use was collected about or more than about 5 days prior to the planned use.

In one aspect, the disclosure provides a system for use in any of the methods disclosed herein. In some embodiments, the system is used for detecting bacterial contamination of a sample, such as a platelet sample, by any of a plurality of bacterial species from different genera. In one embodiment, the system comprises: a computer configured to receive a customer request to perform a detection reaction on a sample; an amplification system that performs a nucleic acid amplification reaction on the sample or a portion thereof in response to the customer request, wherein the amplification reaction yields a detectable amount of an amplicon of no more than about 500 bases of a 16S rRNA polynucleotide using a single primer pair and single probe, and further wherein amplification of 1 pg-5 pg of DNA from any one of the at least five genera has a $C_T$ of less than 30; and a report generator that sends a report to a recipient, wherein the report contains results for detection of a signal intensity produced by the probe.

In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to perform a detection reaction on a sample. The computer may receive the customer request directly (e.g. by way of an input device such as a keyboard, mouse, or touch screen operated by the customer or a user entering a customer request) or indirectly (e.g. through a wired or wireless connection, including over the internet). Non-limiting examples of customers include the subject providing the sample, medical personnel, clinicians, laboratory personnel, insurance company personnel, or others in the health care industry.

In some embodiments, the system comprises an amplification system for performing a nucleic acid amplification reaction on a sample or a portion thereof, responsive to receipt of a customer request by the computer. The amplification system may include a liquid handler, a thermocycler, an optical detector, and/or processor for analyzing detection data. In some embodiments, one or more steps in sample processing, nucleic acid isolation, amplification, and/or analysis are automated by the amplification system. In some embodiments, automation may comprise the use of one or more liquid handlers and associated software. Several commercially available liquid handling systems can be utilized to run the automation of such processes (see for example liquid handlers from Perkin-Elmer, Caliper Life Sciences, Tecan, Eppendorf, Apricot Design, Velocity 11). In some embodiments, detecting comprises a real-time detection instrument. Exemplary real-time instruments include, but are not limited to, the ABI PRISM® 7000 Sequence Detection System, the ABI PRISM® 7700 Sequence Detection System, the Applied Biosystems 7300 Real-Time PCR System, the Applied Biosystems 7500 Real-Time PCR System, the Applied Biosystems 7900 HT Fast Real-Time PCR System (all from Applied Biosystems); the LightCycler™ System (Roche Diagnostics GmbH); the Mx3000P™ Real-Time PCR System, the Mx3005P™ Real-Time PCR System, and the Mx4000® Multiplex Quantitative PCR System (Stratagene, La Jolla, Calif.); and the Smart Cycler System (Cepheid, distributed by Fisher Scientific). Additional non-limiting examples of automated systems for processing and/or assaying samples include COBAS® AmpliPrep/COBAS® TaqMan® systems (Roche Molecular Systems), TIGRIS DTS systems (Hologic Gen-Probe, San Diego, Calif.), PANTHER systems (Hologic Gen-Probe, San Diego, Calif.), BD MAX™ system (Becton Dickinson), GeneXpert System (Cepheid), Filmarray® (BioFire Diagnostics), iCubate systems, IDBox systems (Luminex), EncompassMDx™ (Rheonix), Liat™ Aanlyzer (IQuum), Biocartis' Molecular Diagnostic Platform, Enigma® ML systems (Enigma Diagnosstics), T2Dx® systems (T2 Biosystems), Verigene® system (NanoSphere), Great Basin's Diagnostic System, Unyvero™ System (Curetis), PanNAT systems (Micronics), Spartan™ RX systems (Spartan Bioscience), Atlas io system (Atlas Genetics), Idylla platform (Biocartis), ARIES (Luminex), GenMark's automated PCR platform (e.g. eSensor systems), 3M Integrated Cycler (Focus Diagnostics), and Alere i automated PCR platform (Alere). Descriptions of real-time instruments can be found in, among other places, their respective manufacturer's users manuals; McPherson; DNA Amplification: Current Technologies and Applications, Demidov and Broude, eds., Horizon Bioscience, 2004; and U.S. Pat. No. 6,814,934.

In some embodiments, the system comprises a report generator that sends a report to a recipient, wherein the report contains results for detection of a signal intensity produced by the probe. The report generator may send a report automatically in response to production of fluorescence intensity data by the amplification system, such as in the form of data analysis performed by real-time PCR analysis software. Alternatively, the report generator may send a report in response to instructions from an operator. A report may contain raw signal intensity data, processed signal intensity data (e.g. graphical displays, identification of $C_T$ values, calculation of starting amount of template polynucleotide), a conclusion that bacterial contamination was or was not detected, and/or quantification of an amount of contamination in the source sample (such as in CFU/mL). The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, an individual, a health care provider, a health care manager, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

Figure 5:
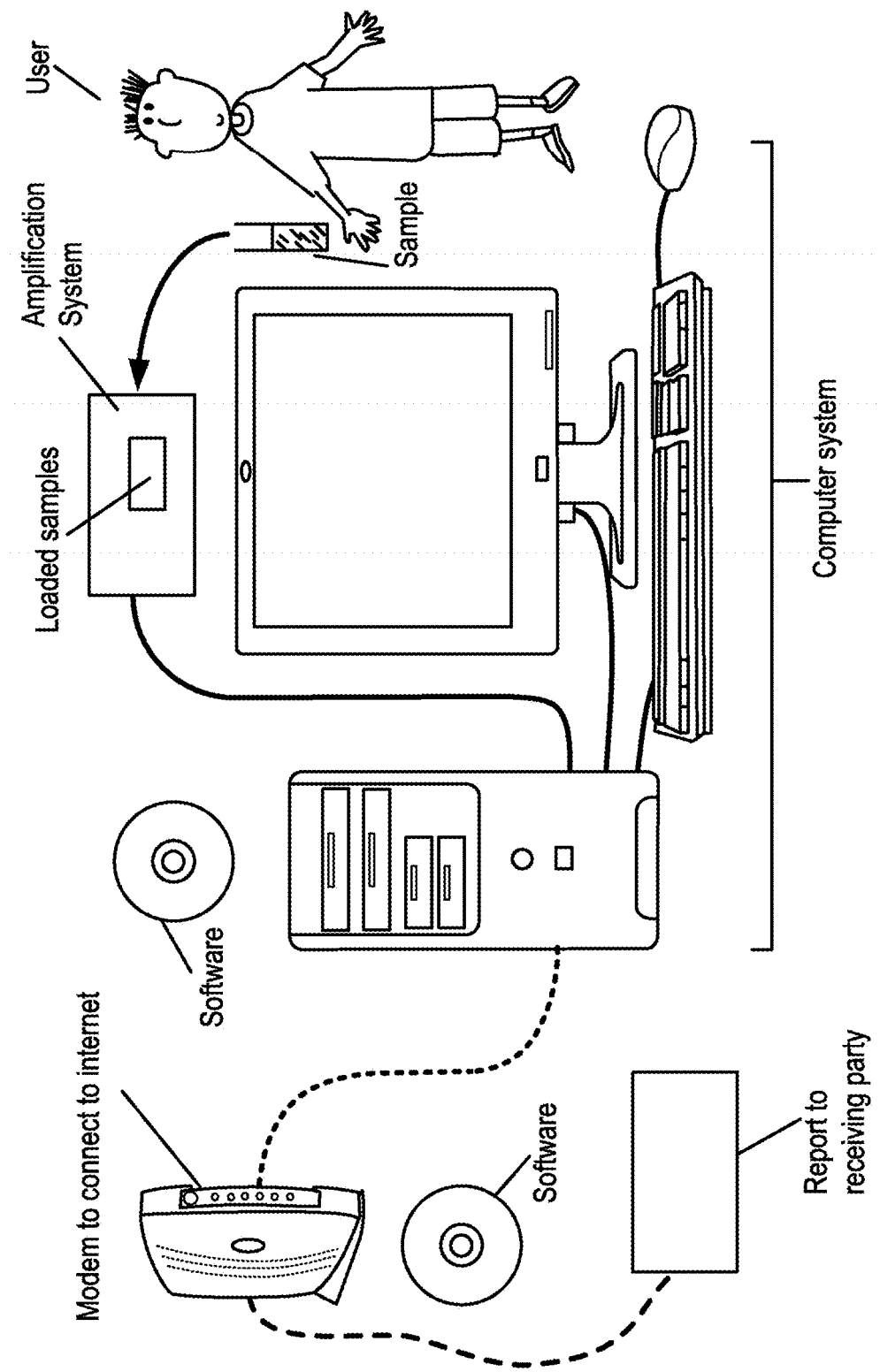
FIG. 5 is an illustration depicting an example sample analysis system.

FIG. 5 illustrates an example system for detecting bacterial contamination of a sample. The system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web.

In one aspect, the disclosure provides a computer-readable medium comprising codes that, upon execution by one or more processors, implements a method according to any of the methods disclosed herein. In some embodiments, execution of the computer readable medium implements a method of detecting bacterial contamination of a biological sample, such as a platelet sample, by any of a plurality of bacterial species from different genera. In one embodiment, execution of the computer readable medium implements a method comprising: responsive to a customer request to perform a detection reaction on a sample, performing a nucleic acid amplification reaction on the sample or a portion thereof in response to the customer request, wherein the amplification reaction yields a detectable amount of an amplicon of no more than about 500 bases of 16S rRNA using a single primer pair and single probe, and further wherein amplification of 1 pg-5 pg of DNA from any one of the at least five genera has a $C_T$ of less than 30; and generating a report that contains results for detection of a signal intensity produced by the probe.

Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

In one aspect, the disclosure provides compositions for amplifying and detecting at least a portion of a conserved polynucleotide. Compositions can comprise one or more elements disclosed herein in relation to any of the various aspects, in any combination. In some embodiments, the conserved polynucleotide is a 16S rRNA polynucleotide (e.g. 16S rRNA, DNA containing a 16S rRNA gene, 16S rRNA and/or rDNA amplification products, or combinations of these). In some embodiments the portion of the 16S rRNA polynucleotide amplified is about or less than about 1000, 900, 800, 700, 600, 500, 400, 300, 250, 200, 175, 150, 125, 100, 90, 80, 70, 60, 50, or fewer nucleotides in length. In some embodiments, the composition comprises: a first primer comprising at least about 10, 11, 12, 13, 14, 15, or all nucleotides of SEQ ID NO: 9; a second primer comprising at least about 10, 11, 12, 13, 14, 15, or all nucleotides of SEQ ID NO: 10; and a probe comprising at least about 10, 11, 12, 13, 14, 15, or all nucleotides of SEQ ID NO: 16. In some embodiments, the composition comprises primers that, in an amplification reaction with a target 16S rRNA polynucleotide, amplify an amplicon of at least 50 nucleotides in length, the amplicon having 90% sequence identity with any of SEQ ID NO: 1-3 when optimally aligned; and a probe that specifically hybridizes to either strand of the amplicon. In some embodiments, the primers and probes are selected in accordance with one or more parameters disclosed herein. For example, primers and probes may be selected such that amplification of about 1 pg-5 pg of DNA from any one of a plurality of target species has a cycle threshold value ($C_T$) of less than 30. Compositions may be contained in any suitable container, such as a well of a multi-well plate, a plate, a tube, a chamber, a flow cell, a chamber or channel of a micro-fluidic device, or a chip. In some embodiments, the composition is in a dehydrated form, such as a bead or film adhered to a surface of a container.

In one aspect, the disclosure provides a reaction mixture for amplification and detection of a conserved polynucleotide. Reaction mixtures can comprise one or more elements disclosed herein in relation to any of the various aspects, in any combination. In some embodiments, the conserved polynucleotide is a 16S rRNA polynucleotide (e.g. 16S rRNA, DNA containing a 16S rRNA gene, 16S rRNA and/or rDNA amplification products, or combinations of these). In some embodiments the portion of the 16S rRNA polynucleotide amplified is about or less than about 1000, 900, 800, 700, 600, 500, 400, 300, 250, 200, 175, 150, 125, 100, 90, 80, 70, 60, 50, or fewer nucleotides in length. In some embodiments, the reaction mixture comprises: a first primer comprising at least about 10, 11, 12, 13, 14, 15, or all nucleotides of SEQ ID NO: 9; a second primer comprising at least about 10, 11, 12, 13, 14, 15, or all nucleotides of SEQ ID NO: 10; and a probe comprising at least about 10, 11, 12, 13, 14, 15, or all nucleotides of SEQ ID NO: 16. In some embodiments, the reaction mixture comprises primers that, in an amplification reaction with a target 16S rRNA polynucleotide, amplify an amplicon of at least 50 nucleotides in length, the amplicon having 90% sequence identity with any of SEQ ID NO: 1-3 when optimally aligned; and a probe that specifically hybridizes to either strand of the amplicon. In some embodiments, the primers and probes are selected in accordance with one or more parameters disclosed herein. For example, primers and probes may be selected such that amplification of about 1 pg-5 pg of DNA from any one of a plurality of target species has a cycle threshold value ($C_T$) of less than 30. Reaction mixtures may be contained in any suitable reaction site. The reaction site may be a container, such as a well of a multi-well plate, a plate, a tube, a chamber, a flow cell, a chamber or channel of a micro-fluidic device, or a chip. The reaction site may be a partition within a solution, such as a droplet (e.g. within an emersion mixture). In some embodiments, the composition is in a dehydrated form, such as a bead or film adhered to a surface of a container.

In one aspect, the disclosure provides kits for detection of bacterial contamination of a biological sample, such as a platelet sample. Kits can comprise one or more elements disclosed herein in relation to any of the various aspects, in any combination. In some embodiments, the kit comprises: a first primer comprising at least about 10, 11, 12, 13, 14, 15, or all nucleotides of SEQ ID NO: 9; a second primer comprising at least about 10, 11, 12, 13, 14, 15, or all nucleotides of SEQ ID NO: 10; and a probe comprising at least about 10, 11, 12, 13, 14, 15, or all nucleotides of SEQ ID NO: 16. Reagents and other materials in a kit may be contained in any suitable container, and may be in an immediately usable form or require combination with other reagents in the kit or reagents supplied by a user (e.g. dilution of a concentrated composition or reconstitution of a lyophilized composition). A kit may provide buffers, non-limiting examples of which include sodium carbonate buffer, a sodium bicarbonate buffer, a borate buffer, a Tris buffer, a MOPS buffer, a HEPES buffer, and combinations thereof. A kit may comprise a control sample, e.g., a known bacterium for control of DNA extraction procedures and/or purified DNA for use as a positive control or quantification standard. In some embodiments, the kit comprises instructions for use of the kit in accordance with one or more methods disclosed herein. In some embodiments, a method for using the kit comprises performing a nucleic acid amplification reaction on a sample or a portion thereof with a single primer pair to yield a detectable amount of an amplicon of no more than about 500 bases of a 16S rRNA polynucleotide, wherein amplification of about 1 pg-5 pg of DNA from any one of a plurality of bacterial species from different genera has a cycle threshold value ($C_T$) of less than 30; and detecting the amplicon with one or more detectable probes, wherein each of the one or more detectable probes specifically hybridizes to a conserved sequence, and the conserved sequence is identical among a plurality of bacterial species from different genera.

TABLE 1

Exemplary Amplification Target Sequences

| | |
|---|---|
| SEQ ID NO: 1 | CAAGGTTGAAACTCAAAGGAATTGACGGGGACCCGCACAAGCGGTGGAGCATGTGGTTTAATTC GAAGCAACGCGAAGAACCTTACC |
| SEQ ID NO: 2 | GCAACGCGAAGAACCTTACCAAATCTTGACATCCTTTGACAACTCTAGAGATAGAGCCTTCCCCTT CGGGGGACAAAGTGACAGGTGGTGCATGGTTGTCGTCAGCTCGTGTCGTGAGATGTTGGGTTAA GTCCCGCA |
| SEQ ID NO: 3 | GCAACGAGCGCAACCCTTAAGCTTAGTTGCCATCATTAAGTTGGGCACTCTAAGTTGACTGCCGG TGACAAACCGGAGGAAGGTGGGGATGACGTCAAATCATCATGCCCCTTATGATTTGGGCTACAC ACGTGCTACAATGG |
| SEQ ID NO: 20 | CTTGCATGTATTAGGCACGCCGCCAGCGTTCATCCTGAGCCAGGATCAAACTCT |
| SEQ ID NO: 21 | AGAGTTTGATCCTGGCTCAGGATGAACGCTGGCGGCGTGCCTAATACATGCAAGT |
| SEQ ID NO: 22 | GGCGTGCCTAATACATGCAAGTCGAGCGAACGGACGAGAAGCTTGCTTCTCTGATGTTAGCGGC GGACGGGTGAGTAA |
| SEQ ID NO: 23 | CGTGCCTAATACATGCAAGTCGAGCGAACGGACGAGAAGCTTGCTTCTCTGATGTTAGCGGCGG ACGGGTGAGTAA |

TABLE 1-continued

Exemplary Amplification Target Sequences

SEQ ID NO: 24  GGCGTGCCTAATACATGCAAGTCGAGCGAACGGACGAGAAGCTTGCTTCTCTGATGTTAGCGGC
GGACGGGTGAGTAACACGTGGATAACCTACCTATAAGACTGGGATAACTTCGGGAAACCGGAGC
TAATACCGGATAATATTTTGAACCGCATGGTTCAAAAGTGAAAGACGGTCTTGCTGTCACTTATA
GATGGATCCGCGCTGCATTAGCTAGTTGGTAAGGTAACGGCTTACCAAGGCAACGATGCATAGC
CGACCTGAGAGGGTGATCGGCCACACTGGAACTGAGACACGGTCCAGACTCCTACGGGAGGCA
GCAGTAGGGAATCTTCCGCAATGGGCGAAAGCCTGACGGAGCAACGCCGCGTGAGTGATGAAG
GTCTTCGGATCGTAAAACTCTGTTATTAGGGAAGAACATATGTGTAAGTAACTGTGCACATCTTG
ACGGTACCTAATCAGAAAGCCACGGCTAACTACGTGCCAGCAGCCGCGGTAATACGTAGGTGGC
AAGCGTTATCCGGAATTATTGGGCGTAAAG

SEQ ID NO: 25  CGTGCCTAATACATGCAAGTCGAGCGAACGGACGAGAAGCTTGCTTCTCTGATGTTAGCGGCGG
ACGGGTGAGTAACACGTGGATAACCTACCTATAAGACTGGGATAACTTCGGGAAACCGGAGCTA
ATACCGGATAATATTTTGAACCGCATGGTTCAAAAGTGAAAGACGGTCTTGCTGTCACTTATAGA
TGGATCCGCGCTGCATTAGCTAGTTGGTAAGGTAACGGCTTACCAAGGCAACGATGCATAGCCG
ACCTGAGAGGGTGATCGGCCACACTGGAACTGAGACACGGTCCAGACTCCTACGGGAGGCAGCA
GTAGGGAATCTTCCGCAATGGGCGAAAGCCTGACGGAGCAACGCCGCGTGAGTGATGAAGGTC
TTCGGATCGTAAAACTCTGTTATTAGGGAAGAACATATGTGTAAGTAACTGTGCACATCTTGACG
GTACCTAATCAGAAAGCCACGGCTAACTACGTGCCAGCAGCCGCGGTAATACGTAGGTGGCAAG
CGTTATCCGGAATTATTGGGCGTAAAG

SEQ ID NO: 26  TTACTCACCCGTCCGCCGCTAACATCAGAGAAGCAAGCTTCTCGTCCGTTCGCTCGACTTGCATGT
ATTAGGCACGCCGCCAGCGTTCATCCTGAGCCAGGATCAAACTCT

SEQ ID NO: 27  AGTCTGGACCGTGTCTCAGTTCCAGTGTGGCCGATCACCCTCTCAGGTCGGCTATGCATCGTTGCC
TTGGTAAGCCGTTACCTTACCAACTAGCTAATGCAGCGCGGATCCATCTATAAGTGACAGCAAGA
CCGTCTTTCACTTTTGAACCATGCGGTTCAAAATATTATCCGGTATTAGCTCCGTTTCCCGAAGTT
ATCCCAGTCTTATAGGTAGGTTATCCACGTGTTACTCACCCGTCCGCCGCTAACATCAGAGAAGCA
AGCTTCTCGTCCGTTCGCTCGACTTGCATGTATTAGGCACGCCGCCAGCGTTCATCCTGAGCCAGG
ATCAAACTCT

SEQ ID NO: 28  CGCGCTTTACGCCCAATAATTCCGGATAACGCTTGCCACCTACGTATTACCGCGGCTGCTGGCACG
TAGTTAGCCGTGGCTTTCTGATTAGGTACCGTCAAGATGTGCACAGTTACTTACACATATGTTCTT
CCCTAATAACAGAGTTTTACGATCCGAAGACCTTCATCACTCACGCGGCGTTGCTCCGTCAGGCTT
TCGCCCATTGCGGAAGATTCCCTACTGCTGCCTCCCGTAGGAGTCTGGACCGTGTCTCAGTTCCAG
TGTGGCCGATCACCCTCTCAGGTCGGCTATGCATCGTTGCCTTGGTAAGCCGTTACCTTACCAACT
AGCTAATGCAGCGCGGATCCATCTATAAGTGACAGCAAGACCGTCTTTCACTTTTGAACCATGCG
GTTCAAAATATTATCCGGTATTAGCTCCGTTTCCCGAAGTTATCCCAGTCTTATAGGTAGGTTAT
CCACGTGTTACTCACCCGTCCGCCGCTAACATCAGAGAAGCAAGCTTCTCGTCCGTTCGCTCGACT
TGCATGTATTAGGCACGCCGCCAGCGTTCATCCTGAGCCAGGATCAAACTCT

SEQ ID NO: 29  TTTGATCCCCACGCTTTCGCACATCAGCGTCAGTTACAGACCAGAAAGTCGCCTTCGCCACTGGTG
TTCCTCCATATCTCTGCGCATTTCACCGCTACACATGGAATTCCACTTTCCTCTTCTGCACTCAAGTT
TTCCAGTTTCCAATGACCCTCCACGGTTGAGCCGTGGGCTTTCACATCAGACTTAAAAAACCGCCT
ACGCGCGCTTTACGCCCAATAATTCCGGATAACGCTTGCCACCTACGTATTACCGCGGCTGCTGGC
ACGTAGTTAGCCGTGGCTTTCTGATTAGGTACCGTCAAGATGTGCACAGTTACTTACACATATGTT
CTTCCCTAATAACAGAGTTTTACGATCCGAAGACCTTCATCACTCACGCGGCGTTGCTCCGTCAGG
CTTTCGCCCATTGCGGAAGATTCCCTACTGCTGCCTCCCGTAGGAGTCTGGACCGTGTCTCAGTTC
CAGTGTGGCCGATCACCCTCTCAGGTCGGCTATGCATCGTTGCCTTGGTAAGCCGTTACCTTACCA
ACTAGCTAATGCAGCGCGGATCCATCTATAAGTGACAGCAAGACCGTCTTTCACTTTTGAACCATG
CGGTTCAAAATATTATCCGGTATTAGCTCCGTTTCCCGAAGTTATCCCAGTCTTATAGGTAGGTT
ATCCACGTGTTACTCACCCGTCCGCCGCTAACATCAGAGAAGCAAGCTTCTCGTCCGTTCGCTCGA
CTTGCATGTATTAGGCACGCCGCCAGCGTTCATCCTGAGCCAGGATCAAACTCT

SEQ ID NO: 30  CGGCTAACTACGTGCCAGCAGCCGCGGTAATACGTAGGTGGCAAGCGTTATCCGGAATTATTGG
GCGTAAAGCGCG

SEQ ID NO: 31  CCAGCAGCCGCGGTAATACGTAGGTGGCAAGCGTTATCCGGAATTATTGGGCGTAAAGCGCG

SEQ ID NO: 32  CCAGCAGCCGCGGTAATACGTAGGTGGCAAGCGTTATCCGGAATTATTGGGCGTAAAG

SEQ ID NO: 33  TGTGTAGCGGTGAAATGCGCAGAGATATGGAGGAACACCAGTGGCGAAGGCGACTTTCTGGTCT
GTAACTGACGCTGATGTGCGAAAGCGTGGGGATCAA

SEQ ID NO: 34  TGTGTAGCGGTGAAATGCGCAGAGATATGGAGGAACACCAGTGGCGAAGGCGACTTTCTGGTCT
GTAACTGACGCTGATGTGCGAAAGCGTGGGATCAAACAGGATTAGATACCCTGGTAGTCCACG
CCGTAAACGATG

SEQ ID NO: 35  CCGCCTGGGGAGTACGACCGCAAGGTTGAAACTCAAAGGAATTGACGGGGACCCGCACAAGCG
GTGGAGCATGTGGTTTAATTCGAAGCAACGCGAAGAACCTTACC

SEQ ID NO: 36  GGGAGTACGACCGCAAGGTTGAAACTCAAAGGAATTGACGGGGACCCGCACAAGCGGTGGAGC
ATGTGGTTTAATTCGAAGCAACGCGAAGAACCTTACC

SEQ ID NO: 37  CGCAAGGTTGAAACTCAAAGGAATTGACGGGGACCCGCACAAGCGGTGGAGCATGTGGTTTAAT
TCGAAGCAACGCGAAGAACCTTACC

SEQ ID NO: 38  GCAAGGTTGAAACTCAAAGGAATTGACGGGGACCCGCACAAGCGGTGGAGCATGTGGTTTAATT
CGAAGCAACGCGAAGAACCTTACC

TABLE 1-continued

Exemplary Amplification Target Sequences

| | |
|---|---|
| SEQ ID NO: 39 | CGGTGAATACGTTCCCGGGTCTTGTACACACCGCCCGTCACACCACGAGAGTTTGTAACACCCGA<br>AGCCGGTGGAGTAACCTTTTAGGAGCTAGCCGTCGAAGGTGGGACAAATGATTGGGGTGAAGTC<br>GTAACAAGG |
| SEQ ID NO: 40 | CGGTGAATACGTTCCCGGGTCTTGTACACACCGCCCGTCACACCACGAGAGTTTGTAACACCCGA<br>AGCCGGTGGAGTAACCTTTTAGGAGCTAGCCGTCGAAGGTGGGACAAATGATTGGGGTGAAGTC<br>GTAACAAGGTAGC |
| SEQ ID NO: 41 | TGTACACACCGCCCGTCACACCACGAGAGTTTGTAACACCCGAAGCCGGTGGAGTAACCTTTTAG<br>GAGCTAGCCGTCGAAGGTGGGACAAATGATTGGGGTGAAGTCGTAACAAGGTAGCCGTATCGG<br>AAGGTGCGGCTGGATCACCTCCTT |

TABLE 2

Exemplary Primer Sequences

| | |
|---|---|
| SEQ ID NO: 4 | GGTAAGGTTCTTCGCGTTGC |
| SEQ ID NO: 5 | CAAGGTTGAAACTCAAAGGAATTGA |
| SEQ ID NO: 6 | CAAGGTTAAAACTCAAATGAATTGA |
| SEQ ID NO: 7 | TGCGGGACTTAACCCAACAT |
| SEQ ID NO: 8 | GCAACGCGAAGAACCTTACC |
| SEQ ID NO: 9 | CCATTGTAGCACGTGTGTAGCC |
| SEQ ID NO: 10 | GCAACGAGCGCAACCC |
| SEQ ID NO: 42 | GGTAAGGTTCTACGCGTTGC |
| SEQ ID NO: 43 | CAAGGCTGAAACTCAAAGGAATTGA |
| SEQ ID NO: 44 | CAAGGCTAAAACTCAAAGGAATTGA |
| SEQ ID NO: 45 | TACGGGACTTAACCCAACAT |
| SEQ ID NO: 46 | GCAACGCGTAGAACCTTACC |
| SEQ ID NO: 47 | CCATTGTAGCATGCGTGAAGCC |
| SEQ ID NO: 48 | GTAACGAGCGCAACCC |
| SEQ ID NO: 49 | CCATTGTAGCACGTGTGTAGCCC |
| SEQ ID NO: 50 | CCATTGTAGCATGCGTGAAGCCC |
| SEQ ID NO: 51 | AGAGTTTGATCCTGGCTCAG |
| SEQ ID NO: 52 | TGCATGTATTAGGCACGCC |
| SEQ ID NO: 53 | TGCATGTGTTAGGCCTGCC |
| SEQ ID NO: 54 | TGCATGTGTTAAGCACGCC |
| SEQ ID NO: 55 | ACTTGCATGTATTAGGCACG |
| SEQ ID NO: 56 | ACTTGCATGTGTTAGGCCTG |
| SEQ ID NO: 57 | ACTTGCATGTGTTAAGCACG |
| SEQ ID NO: 58 | TTACTCACCCGTCCGCC |
| SEQ ID NO: 59 | TTACTCACCCGTTCGCA |
| SEQ ID NO: 60 | TTACTCACCCATCCGCC |
| SEQ ID NO: 61 | TTACTCACCCGTTCGCC |
| SEQ ID NO: 62 | AGTCTGGACCGTGTCTCAGTTC |
| SEQ ID NO: 63 | AGTCTGGGCCGTGTCTCAGTCC |
| SEQ ID NO: 64 | AGTTTGGGCCGTGTCTCAGTCC |
| SEQ ID NO: 65 | AGTCTGGGCCGTATCTCAGTCC |
| SEQ ID NO: 66 | CTTTACGCCCAATAATTCCG |
| SEQ ID NO: 67 | CTTTACGCCCAGTAATTCCG |
| SEQ ID NO: 68 | CTTTACGCCCAATAAATCCG |
| SEQ ID NO: 69 | TTTGATCCCCACGCTTT |
| SEQ ID NO: 70 | TTTGCTCCCCACGCTTT |
| SEQ ID NO: 71 | TTCGCTACCCATGCTTT |
| SEQ ID NO: 72 | TTCGCTCCCCACGCTTT |
| SEQ ID NO: 73 | CGGCTAACTACGTGCCAGC |
| SEQ ID NO: 74 | CGGCTAACTCCGTGCCAGC |
| SEQ ID NO: 75 | CGGCTAACTTCGTGCCAGC |
| SEQ ID NO: 76 | CCAGCAGCCGCGGTAAT |
| SEQ ID NO: 77 | CCAGCAGCCGCGGTGAT |
| SEQ ID NO: 78 | CGCGCTTTACGCCCAATA |
| SEQ ID NO: 79 | TGCGCTTTACGCCCAGTA |
| SEQ ID NO: 80 | CTCGCTTTACGCCCAATA |
| SEQ ID NO: 81 | AGCCCTTTACGCCCAATA |
| SEQ ID NO: 82 | TGTGTAGCGGTGAAATGCG |
| SEQ ID NO: 83 | GGTGTAGCGGTGAAATGCG |
| SEQ ID NO: 84 | GTGTAGCGGTGGAATGCG |
| SEQ ID NO: 85 | GTGGAGCGGTGGAATGCG |
| SEQ ID NO: 86 | TTGATCCCCACGCTTTCG |
| SEQ ID NO: 87 | TTGCTCCCCACGCTTTCG |
| SEQ ID NO: 88 | TCGCTACCCATGCTTTCG |

TABLE 2-continued

Exemplary Primer Sequences

| | |
|---|---|
| SEQ ID NO: 89 | TCGCTCCCCACGCTTTCG |
| SEQ ID NO: 90 | CATCGTTTACGGCGTGGA |
| SEQ ID NO: 91 | CATCGTTTACAGCGTGGA |
| SEQ ID NO: 92 | CATCGTTTACGGCATGGA |
| SEQ ID NO: 93 | CACCGTTTACAGCGTGGA |
| SEQ ID NO: 94 | GGGAGTACGACCGCAAGGT |
| SEQ ID NO: 95 | GGGGAGTACGGCCGCAAGG |
| SEQ ID NO: 96 | CCGCCTGGGGAGTACG |
| SEQ ID NO: 97 | CGCAAGGTTGAAACTCAAAGG |
| SEQ ID NO: 98 | CGCAAGGTTAAAACTCAAATG |
| SEQ ID NO: 99 | CGCAAGGCTGAAACTCAAAGG |
| SEQ ID NO: 100 | CGCAAGGCTAAAACTCAAAGG |
| SEQ ID NO: 101 | GCAAGGTTGAAACTCAAAGGAATT |
| SEQ ID NO: 102 | GCAAGGTTAAAACTCAAATGAATT |
| SEQ ID NO: 103 | GCAAGGCTGAAACTCAAAGGAATT |
| SEQ ID NO: 104 | GCAAGGCTAAAACTCAAAGGAATT |
| SEQ ID NO: 105 | CGGTGAATACGTTCCCGG |
| SEQ ID NO: 106 | CCTTGTTACGACTTCACCCCA |
| SEQ ID NO: 107 | CCTTGTTACGACTTAGTCCTA |
| SEQ ID NO: 108 | CGGTGAATACGTTCCCGG |
| SEQ ID NO: 109 | GCTACCTTGTTACGACTTCACCC |
| SEQ ID NO: 110 | GTTACCTTGTTACGACTTCACCC |
| SEQ ID NO: 111 | GCTACCTTGTTACGACTTAGTCC |
| SEQ ID NO: 112 | TGTACACACCGCCCGTCACA |
| SEQ ID NO: 113 | TGTACACACCGCCCGTCAAG |
| SEQ ID NO: 114 | AAGGAGGTGATCCAGCCGC |
| SEQ ID NO: 115 | AAGGAGGTGATCCAACCGC |
| SEQ ID NO: 116 | TTTGATCCTGGCTCAG |
| SEQ ID NO: 117 | TTTGATCATGGCTCAG |
| SEQ ID NO: 118 | GAACGCTGGCGGC |
| SEQ ID NO: 119 | GCCTAATACATGCAAGT |
| SEQ ID NO: 120 | GCCTAACACATGCAAGT |
| SEQ ID NO: 121 | GGCGTGCCTAATACATGCA |
| SEQ ID NO: 122 | GGCAGGCCTAACACATGCA |
| SEQ ID NO: 123 | GGCGTGCTTAACACATGCA |
| SEQ ID NO: 124 | CGTGCCTAATACATGCAAGT |
| SEQ ID NO: 125 | CAGGCCTAACACATGCAAGT |
| SEQ ID NO: 126 | CGTGCTTAACACATGCAAGT |

TABLE 3

Exemplary Probe Sequences

| | |
|---|---|
| SEQ ID NO: 11 | TCGAATTAAACCACATGCTCCACCGCT |
| SEQ ID NO: 12 | TCGAATTAATCCGCATGCTCCGCCGCT |
| SEQ ID NO: 13 | TCGAATTAAACCACATGCTCCGCTACT |
| SEQ ID NO: 14 | AGCTGACGACAGCCATGCAGCACCT |
| SEQ ID NO: 15 | AGCTGACGACAACCATGCACCACCT |
| SEQ ID NO: 16 | TGACGTCATCCCCACCTTCCTCC |
| SEQ ID NO: 127 | AGCTGACGACAGCCATGCACCACCT |
| SEQ ID NO: 128 | ACACGAGCTGACGACAACCATGCACCACCTGT |
| SEQ ID NO: 129 | ACAGGTGCTGCATGGCTGTCGTCAGCTCGTGT |
| SEQ ID NO: 130 | ACAGGTGGTGCATGGCTGTCGTCAGCTCGTGT |
| SEQ ID NO: 131 | AACGCTGGCGGCGTGC |
| SEQ ID NO: 132 | AACGCTGGCGGCAGGC |
| SEQ ID NO: 133 | CGGCGTGCCTAATACATGCAAG |
| SEQ ID NO: 134 | CGGCAGGCCTAACACATGCAAG |
| SEQ ID NO: 135 | CGGCAGGCTTAACACATGCAAG |
| SEQ ID NO: 136 | CGGCGTGCTTAACACATGCAAG |
| SEQ ID NO: 137 | CGTAGGTGGCAAGCGTTATCCGGAA |
| SEQ ID NO: 138 | CGGAGGGTGCAAGCGTTAATCGGAA |
| SEQ ID NO: 139 | CGTAGGTCCCGAGCGTTGTCCGGAT |
| SEQ ID NO: 140 | CAGTGGCGAAGGCGACTTTCTG |
| SEQ ID NO: 141 | CAGGGGGCCGCCTTCGCCACCG |
| SEQ ID NO: 142 | CAGAGAGCCGCTTTCGCCACCG |
| SEQ ID NO: 143 | GGGATCAAACAGGATTAGATACCCTGGT |
| SEQ ID NO: 144 | GGGAGCAAACAGGATTAGATACCCTGGT |
| SEQ ID NO: 145 | GGGAGCGAACAGGCTTAGATACCCTGGT |
| SEQ ID NO: 146 | ACAAGCGGTGGAGCATGTGGTTTAATTC |
| SEQ ID NO: 147 | ACAAGCGGCGGAGCATGCGGATTAATTC |
| SEQ ID NO: 148 | ACAAGTAGCGGAGCATGTGGTTTAATTC |
| SEQ ID NO: 149 | AGCGGTGGAGCATGTGGTTTAATTCG |
| SEQ ID NO: 150 | AGCGGCGGAGCATGCGGATTAATTCG |
| SEQ ID NO: 151 | AGTAGCGGAGCATGTGGTTTAATTCG |
| SEQ ID NO: 152 | AAGCGGTGGAGCATGTGGTTTAATTCG |
| SEQ ID NO: 153 | AGCGGCGGAGCATGCGGATTAATTCG |
| SEQ ID NO: 154 | AGTAGCGGAGCATGTGGTTTAATTCG |
| SEQ ID NO: 155 | TGTACACACCGCCCGTCA |

TABLE 15

Exemplary Pairing of Sequences as Primers

| | Included or Optional | Bacteria Target Coverage |
|---|---|---|
| Exemplary Primer Set 1 | | |
| SEQ ID NO: 4 | Included | *Staphylococcus aureus, Staphylococcus aureus* Mu3; |
| SEQ ID NO: 5 | Included | *Staphylococcus epidermidis, Streptococcus agalactiae,* |
| SEQ ID NO: 6 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Staphylococcus aureus* Mu50, *Yersinia enterocolitica, Staphylococcus simulans, Micrococcus luteus,* and *Enterobacter aerogenes* |
| SEQ ID NO: 42 | Optional | Improves *Propionibacterium* sp. amplification based on sequence homology |
| SEQ ID NO: 43 | Optional | Improves *Bacillus cereus* amplification based on sequence homology |
| SEQ ID NO: 44 | Optional | Improves *Propionibacterium* sp. amplification based on sequence homology |
| Exemplary Primer Set 2 | | |
| SEQ ID NO: 7 | Included | *Staphylococcus aureus, Staphylococcus aureus* Mu3; |
| SEQ ID NO: 8 | Included | *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 45 | Optional | Improves *Pseudomonas aeruginosa* amplification based on sequence homology |
| SEQ ID NO: 46 | Optional | Improves *Propionibacterium* sp. amplification based on sequence homology |
| Exemplary Primer Set 3 | | |
| SEQ ID NO: 9 | Included | *Staphylococcus aureus, Staphylococcus aureus* Mu3; |
| SEQ ID NO: 10 | Included | *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Propionibacterium* sp., *Pseudomonas aeruginosa, Lactobacillus acidophilus, Listeria monocytogenes, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 47 | Optional | Improves *Propionibacterium* sp. amplification based on sequence homology |
| SEQ ID NO: 48 | Optional | Improves *Pseudomonas aeruginosa* amplification based on sequence homology |
| Exemplary Primer Set 4 | | |
| SEQ ID NO: 51 | Included | *Staphylococcus aureus, Staphylococcus aureus* Mu3; |
| SEQ ID NO: 52 | Included | *Staphylococcus epidermidis, Streptococcus agalactiae,* |
| SEQ ID NO: 53 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 54 | Optional | Improves *Propionibacterium* sp. amplification based on sequence homology |
| Exemplary Primer Set 5 | | |
| SEQ ID NO: 51 | Included | *Staphylococcus aureus, Staphylococcus aureus* Mu3; *Staphylococcus epidermidis, Streptococcus agalactiae, Streptococcus pyogenes, Streptococcus pneumonia, Escherichia coli, Citrobacter koseri, Enterococcus faecalis, Klebsiella pneumonia, Lactobacillus acidophilus, Listeria* monocytogenes, *Pseudomonas aeruginosa, Serratia marcescens, Bacillus cereus,* |

TABLE 15-continued

Exemplary Pairing of Sequences as Primers

| | Included or Optional | Bacteria Target Coverage |
|---|---|---|
| | | *Staphylococcus aureus* Mu50, *Yersinia enterocolitica*, *Staphylococcus simulans*, *Micrococcus luteus*, and *Enterobacter aerogenes* |
| SEQ ID NO: 55 | Included | |
| SEQ ID NO: 56 | Included | |
| SEQ ID NO: 57 | Optional | Improves *Propionibacterium* sp. and *Clostridium perfringens* amplification based on sequence homology |
| Exemplary Primer Set 6 | | |
| SEQ ID NO: 58 | Included | *Staphylococcus aureus*, *Staphylococcus aureus* Mu3; |
| SEQ ID NO: 59 | Included | *Staphylococcus epidermidis*, *Streptococcus agalactiae*, |
| SEQ ID NO: 121 | Included | *Streptococcus pyogenes*, *Streptococcus pneumonia*, *Escherichia* |
| SEQ ID NO: 122 | Included | *coli*, *Citrobacter koseri*, *Clostridium perfringens*, *Enterococcus faecalis*, *Klebsiella pneumonia*, *Listeria monocytogenes*, *Pseudomonas aeruginosa*, *Serratia marcescens*, *Bacillus cereus*, *Staphylococcus aureus* Mu50, *Yersinia enterocolitica*, *Staphylococcus simulans*, *Micrococcus luteus*, and *Enterobacter aerogenes* |
| SEQ ID NO: 60 | Optional | Improves *Lactobacillus acidophilus* amplification based on sequence homology |
| SEQ ID NO: 61 | Optional | Improves *Propionibacterium* sp. amplification based on sequence homology |
| SEQ ID NO: 123 | Optional | Improves *Propionibacterium* sp. amplification based on sequence homology |
| Exemplary Primer Set 7 | | |
| SEQ ID NO: 58 | Included | *Staphylococcus aureus*, *Staphylococcus aureus* Mu3; |
| SEQ ID NO: 59 | Included | *Staphylococcus epidermidis*, *Streptococcus agalactiae*, |
| SEQ ID NO: 124 | Included | *Streptococcus pyogenes*, *Streptococcus pneumonia*, *Escherichia* |
| SEQ ID NO: 125 | Included | *coli*, *Citrobacter koseri*, *Enterococcus faecalis*, *Klebsiella pneumonia*, *Listeria monocytogenes*, *Pseudomonas aeruginosa*, *Serratia marcescens*, *Bacillus cereus*, *Staphylococcus aureus* Mu50, *Yersinia enterocolitica*, *Staphylococcus simulans*, *Micrococcus luteus*, and *Enterobacter aerogenes* |
| SEQ ID NO: 60 | Optional | Improves *Lactobacillus acidophilus* amplification based on sequence homology |
| SEQ ID NO: 61 | Optional | Improves *Propionibacterium* sp. amplification based on sequence homology |
| SEQ ID NO: 126 | Optional | Improves *Propionibacterium* sp. and *Clostridium perfringens* amplification based on sequence homology |
| Exemplary Primer Set 8 | | |
| SEQ ID NO: 66 | Included | *Staphylococcus aureus*, *Staphylococcus aureus* Mu3; |
| SEQ ID NO: 67 | Included | *Staphylococcus epidermidis*, *Streptococcus agalactiae*, |
| SEQ ID NO: 68 | Included | *Streptococcus pyogenes*, *Streptococcus pneumonia*, *Escherichia* |
| SEQ ID NO: 121 | Included | *coli*, *Citrobacter koseri*, *Clostridium perfringens*, *Enterococcus* |
| SEQ ID NO: 122 | Included | *faecalis*, *Klebsiella pneumonia*, *Lactobacillus acidophilus*, *Listeria monocytogenes*, *Pseudomonas aeruginosa*, *Serratia marcescens*, *Bacillus cereus*, *Staphylococcus aureus* Mu50, *Yersinia enterocolitica*, *Staphylococcus simulans*, *Micrococcus luteus*, and *Enterobacter aerogenes* |
| SEQ ID NO: 123 | Optional | Improves *Propionibacterium* sp. amplification based on sequence homology |
| Exemplary Primer Set 9 | | |
| SEQ ID NO: 66 | Included | *Staphylococcus aureus*, *Staphylococcus aureus* Mu3; |
| SEQ ID NO: 67 | Included | *Staphylococcus epidermidis*, *Streptococcus agalactiae*, |
| SEQ ID NO: 68 | Included | *Streptococcus pyogenes*, *Streptococcus pneumonia*, *Escherichia* |
| SEQ ID NO: 124 | Included | *coli*, *Citrobacter koseri*, *Enterococcus faecalis*, *Klebsiella* |
| SEQ ID NO: 125 | Included | *pneumonia*, *Lactobacillus acidophilus*, *Listeria monocytogenes*, *Pseudomonas aeruginosa*, *Serratia marcescens*, *Bacillus cereus*, *Staphylococcus aureus* Mu50, *Yersinia enterocolitica*, *Staphylococcus simulans*, *Micrococcus luteus*, and *Enterobacter aerogenes* |
| SEQ ID NO: 126 | Optional | Improves *Propionibacterium* sp. and *Clostridium perfringens* amplification based on sequence homology |
| Exemplary Primer Set 10 | | |
| SEQ ID NO: 51 | Included | *Staphylococcus aureus*, *Staphylococcus aureus* Mu3; |
| SEQ ID NO: 58 | Included | *Staphylococcus epidermidis*, *Streptococcus agalactiae*, |

TABLE 15-continued

Exemplary Pairing of Sequences as Primers

| | Included or Optional | Bacteria Target Coverage |
|---|---|---|
| SEQ ID NO: 59 | Included | *Streptococcus pyogenes, Streptococcus pneumonia, Escherichia coli, Citrobacter koseri, Clostridium perfringens, Enterococcus faecalis, Klebsiella pneumonia, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 60 | Optional | Improves *Lactobacillus acidophilus* amplification based on sequence homology |
| SEQ ID NO: 61 | Optional | Improves *Propionibacterium* sp. amplification based on sequence homology |
| Exemplary Primer Set 11 | | |
| SEQ ID NO: 51 | Included | *Staphylococcus aureus, Staphylococcus aureus* Mu3; |
| SEQ ID NO: 62 | Included | *Staphylococcus epidermidis, Streptococcus agalactiae,* |
| SEQ ID NO: 63 | Included | *Streptococcus pyogenes, Streptococcus pneumonia, Escherichia coli, Citrobacter koseri, Clostridium perfringens, Enterococcus faecalis, Klebsiella pneumonia, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 64 | Optional | Improves *Lactobacillus acidophilus* amplification based on sequence homology |
| SEQ ID NO: 65 | Optional | Improves *Propionibacterium* sp. amplification based on sequence homology |
| Exemplary Primer Set 12 | | |
| SEQ ID NO: 51 | Included | *Staphylococcus aureus, Staphylococcus aureus* Mu3; |
| SEQ ID NO: 66 | Included | *Staphylococcus epidermidis, Streptococcus agalactiae,* |
| SEQ ID NO: 67 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Propionibacterium granulosum, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 68 | Included | |
| Exemplary Primer Set 13 | | |
| SEQ ID NO: 51 | Included | *Staphylococcus aureus, Staphylococcus aureus* Mu3; |
| SEQ ID NO: 69 | Included | *Staphylococcus epidermidis, Streptococcus agalactiae,* |
| SEQ ID NO: 70 | Included | *Streptococcus pyogenes, Streptococcus pneumonia, Escherichia coli, Citrobacter koseri, Clostridium perfringens, Enterococcus faecalis, Klebsiella pneumonia, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 71 | Optional | Improves *Lactobacillus acidophilus* amplification based on sequence homology |
| SEQ ID NO: 72 | Optional | Improves *Propionibacterium* sp. amplification based on sequence homology |
| Exemplary Primer Set 14 | | |
| SEQ ID NO: 73 | Included | *Staphylococcus aureus, Staphylococcus aureus* Mu3; |
| SEQ ID NO: 74 | Included | *Staphylococcus epidermidis, Streptococcus agalactiae,* |
| SEQ ID NO: 63 | Included | *Streptococcus pyogenes, Streptococcus pneumonia, Escherichia coli, Citrobacter koseri, Clostridium perfringens, Enterococcus faecalis, Klebsiella pneumonia, Listeria monocytogenes, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 62 | Included | |
| SEQ ID NO: 75 | Optional | Improves *Pseudomonas aeruginosa* amplification based on sequence homology |
| SEQ ID NO: 64 | Optional | Improves *Lactobacillus acidophilus* amplification based on sequence homology |
| SEQ ID NO: 65 | Optional | Improves *Propionibacterium* sp. amplification based on sequence homology |

TABLE 15-continued

Exemplary Pairing of Sequences as Primers

| | Included or Optional | Bacteria Target Coverage |
|---|---|---|
| Exemplary Primer Set 15 | | |
| SEQ ID NO: 76 | Included | *Staphylococcus aureus, Staphylococcus aureus* Mu3; |
| SEQ ID NO: 78 | Included | *Staphylococcus epidermidis, Streptococcus agalactiae,* |
| SEQ ID NO: 79 | Included | *Streptococcus pyogenes, Streptococcus pneumonia, Escherichia* |
| SEQ ID NO: 80 | Included | *coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 77 | Optional | Improves *Propionibacterium* sp. amplification based on sequence homology |
| SEQ ID NO: 81 | Optional | Improves *Propionibacterium* sp. amplification based on sequence homology |
| Exemplary Primer Set 16 | | |
| SEQ ID NO: 76 | Included | *Staphylococcus aureus, Staphylococcus aureus* Mu3; |
| SEQ ID NO: 66 | Included | *Staphylococcus epidermidis, Streptococcus agalactiae,* |
| SEQ ID NO: 67 | Included | *Streptococcus pyogenes, Streptococcus pneumonia, Escherichia* |
| SEQ ID NO: 68 | Included | *coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 77 | Optional | Improves *Propionibacterium* sp. amplification based on sequence homology |
| Exemplary Primer Set 17 | | |
| SEQ ID NO: 82 | Included | *Staphylococcus aureus, Staphylococcus aureus* Mu3; |
| SEQ ID NO: 83 | Included | *Staphylococcus epidermidis, Streptococcus agalactiae,* |
| SEQ ID NO: 86 | Included | *Streptococcus pyogenes, Streptococcus pneumonia, Escherichia* |
| SEQ ID NO: 87 | Included | *coli, Citrobacter koseri, Clostridium perfringens, Enterococcus faecalis, Klebsiella pneumonia, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 84 | Optional | Improves *Lactobacillus acidophilus* amplification based on sequence homology |
| SEQ ID NO: 85 | Optional | Improves *Propionibacterium* sp. amplification based on sequence homology |
| SEQ ID NO: 88 | Optional | Improves *Lactobacillus acidophilus* amplification based on sequence homology |
| SEQ ID NO: 89 | Optional | Improves *Propionibacterium* sp. amplification based on sequence homology |
| Exemplary Primer Set 18 | | |
| SEQ ID NO: 82 | Included | *Staphylococcus aureus, Staphylococcus aureus* Mu3; |
| SEQ ID NO: 83 | Included | *Staphylococcus epidermidis, Streptococcus agalactiae,* |
| SEQ ID NO: 90 | Included | *Streptococcus pyogenes, Streptococcus pneumonia, Escherichia* |
| SEQ ID NO: 91 | Included | *coli, Citrobacter koseri, Clostridium perfringens, Enterococcus faecalis, Klebsiella pneumonia, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 84 | Optional | Improves *Lactobacillus acidophilus* amplification based on sequence homology |
| SEQ ID NO: 85 | Optional | Improves *Propionibacterium* sp. amplification based on sequence homology |
| SEQ ID NO: 92 | Optional | Improves *Lactobacillus acidophilus* amplification based on sequence homology |
| SEQ ID NO: 93 | Optional | Improves *Propionibacterium* sp. amplification based on sequence homology |
| Exemplary Primer Set 19 | | |
| SEQ ID NO: 96 | Included | *Staphylococcus aureus, Staphylococcus aureus* Mu3; |
| SEQ ID NO: 4 | Included | *Staphylococcus epidermidis, Streptococcus agalactiae,* |

TABLE 15-continued

Exemplary Pairing of Sequences as Primers

| | Included or Optional | Bacteria Target Coverage |
|---|---|---|
| | | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus*, and *Enterobacter aerogenes* |
| SEQ ID NO: 42 | Optional | Improves *Propionibacterium* sp. amplification based on sequence homology |
| Exemplary Primer Set 20 | | |
| SEQ ID NO: 94 | Included | *Staphylococcus aureus, Staphylococcus aureus* Mu3; |
| SEQ ID NO: 95 | Included | *Staphylococcus epidermidis, Streptococcus agalactiae,* |
| SEQ ID NO: 4 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus*, and *Enterobacter aerogenes* |
| SEQ ID NO: 42 | Optional | Improves *Propionibacterium* sp. amplification based on sequence homology |
| Exemplary Primer Set 21 | | |
| SEQ ID NO: 98 | Included | *Staphylococcus aureus, Staphylococcus aureus* Mu3; |
| SEQ ID NO: 4 | Included | *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Staphylococcus aureus* Mu50, *Yersinia enterocolitica, Staphylococcus simulans, Micrococcus luteus*, and *Enterobacter aerogenes* |
| SEQ ID NO: 99 | Optional | Improves *Bacillus cereus* amplification based on sequence homology |
| SEQ ID NO: 100 | Optional | Improves *Propionibacterium* sp. amplification based on sequence homology |
| SEQ ID NO: 42 | Optional | Improves *Propionibacterium* sp. amplification based on sequence homology |
| Exemplary Primer Set 22 | | |
| SEQ ID NO: 102 | Included | *Staphylococcus aureus, Staphylococcus aureus* Mu3; |
| SEQ ID NO: 4 | Included | *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Staphylococcus aureus* Mu50, *Yersinia enterocolitica, Staphylococcus simulans, Micrococcus luteus*, and *Enterobacter aerogenes* |
| SEQ ID NO: 103 | Optional | Improves *Bacillus cereus* amplification based on sequence homology |
| SEQ ID NO: 104 | Optional | Improves *Propionibacterium* sp. amplification based on sequence homology |
| SEQ ID NO: 42 | Optional | Improves *Propionibacterium* sp. amplification based on sequence homology |
| Exemplary Primer Set 23 | | |
| SEQ ID NO: 105 | Included | *Staphylococcus aureus, Staphylococcus aureus* Mu3; |
| SEQ ID NO: 106 | Included | *Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus*, and *Enterobacter aerogenes* |
| SEQ ID NO: 107 | Optional | Improves *Propionibacterium* sp. amplification based on sequence homology |

TABLE 15-continued

Exemplary Pairing of Sequences as Primers

Included or Optional Bacteria Target Coverage

Exemplary Primer Set 24

| | | |
|---|---|---|
| SEQ ID NO: 108 | Included | *Staphylococcus aureus, Staphylococcus aureus* Mu3; |
| SEQ ID NO: 109 | Included | *Staphylococcus epidermidis, Streptococcus agalactiae,* |
| SEQ ID NO: 110 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 111 | Optional | Improves *Propionibacterium* sp. amplification based on sequence homology |

Exemplary Primer Set 25

| | | |
|---|---|---|
| SEQ ID NO: 112 | Included | *Staphylococcus aureus, Staphylococcus aureus* Mu3; |
| SEQ ID NO: 114 | Included | *Staphylococcus epidermidis, Streptococcus agalactiae,* |
| SEQ ID NO: 115 | Included | *Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Pseudomonas aeruginosa, Serratia marcescens, Bacillus cereus, Staphylococcus aureus* Mu50, *Yersinia enterocolitica, Staphylococcus simulans, Micrococcus luteus,* and *Enterobacter aerogenes* |
| SEQ ID NO: 113 | Optional | Improves *Propionibacterium* sp. amplification based on sequence homology |

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

An example pair of primers and an example probe for the corresponding amplicon were evaluated for specificity, detection range, and ability to detect a variety of bacterial species from multiple different genera. In this example, a primer having sequence SEQ ID NO: 9, a primer having sequence SEQ ID NO: 10, and a probe having sequence SEQ ID NO: 16, were used to amplify and detect a conserved portion of 16S rRNA gene. The primers and probe were designed against the sequence SEQ ID NO: 3. Real-time PCR reactions were prepared with the indicated amount of bacterial genomic DNA, as well as primers, probe, enzyme, dNTP's, and other standard reagents.

Figure 2:
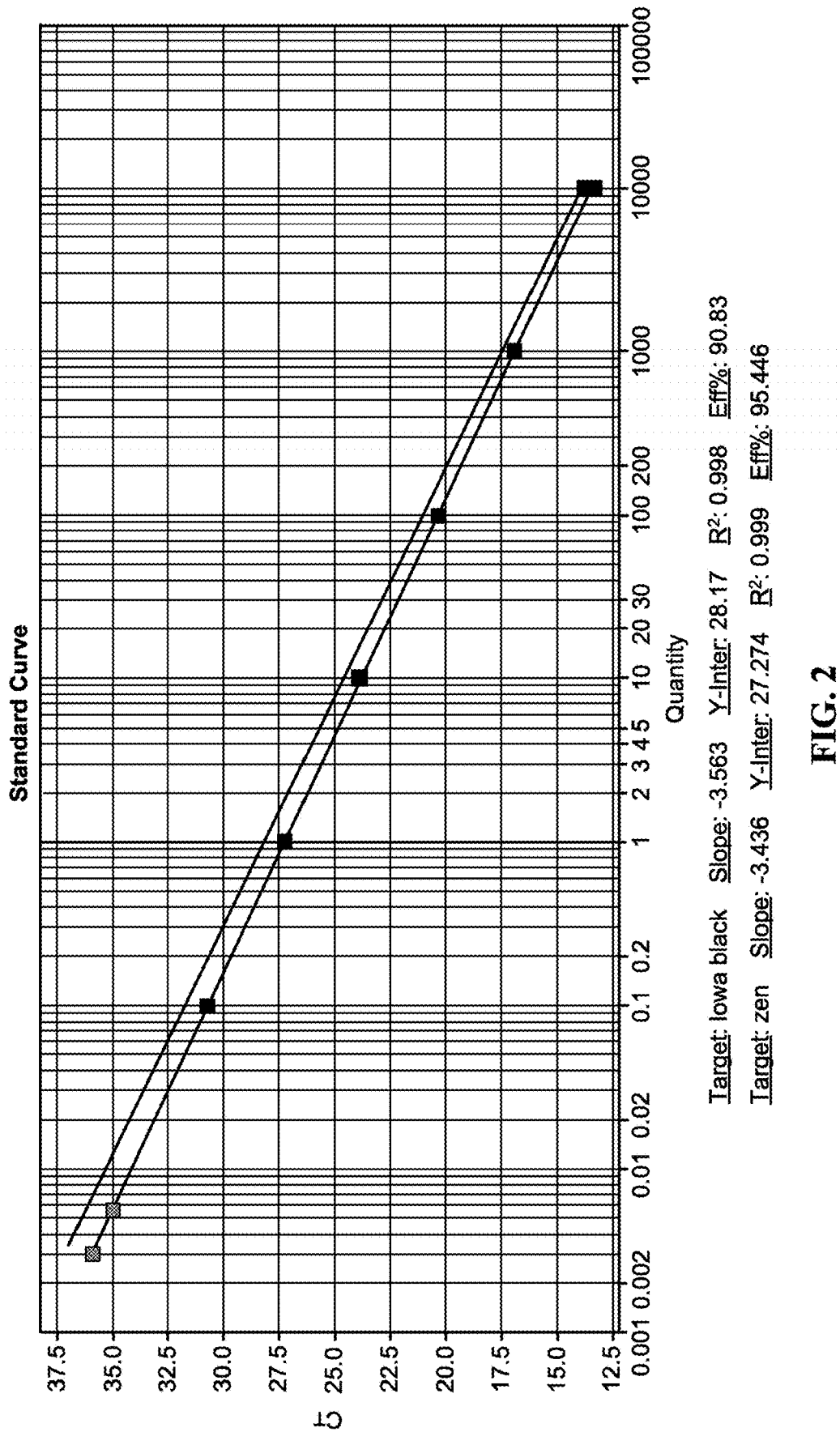
FIG. 2 is a graph illustrating the detection range of a nucleic acid amplification assay.

To evaluate sensitivity of the primer-probe combination, amplification reactions containing 10 ng, 1 ng, 100 pg, 10 pg, 1 pg, and 0.1 pg of *E. coli* DNA extract were prepared in duplicate. No-template controls, containing all common reagents but replacing DNA extract with water, were prepared in quadruplicate. A graphical display of the results of real-time PCR amplification is shown in FIG. 1. A log-scale of arbitrary fluorescence intensity along the y-axis (0 to 10) is plotted against cycle number along the x-axis (0 to 40). From left to right, the first pair of curves correspond to the 10 ng sample (average $C_T$ of about 14.5), followed by overlapping pairs of curves corresponding to the 1 ng, 100 pg, 10 pg, 1 pg, and 0.1 pg samples ($C_T$'s of about 17.5, 21, 24.5, 27.5, and 31). Without wishing to be bound by theory, it is possible that the amplification signal around $C_T$ of 36 for the four no-template control samples may result from residual bacterial polynucleotides in the commercially obtained enzyme. Nevertheless, specific amplification signals with this combination of primers and probe provide a 6-log range of detection, with 0.1 pg of starting template detected at least 5 full cycles before signal from the negative control. In fact, the detection over this range is linear, as shown in FIG. 2 ($R^2$ of about 0.999, and amplification efficiency of about 95.5% over this range), and may therefore be used to quantify amounts of starting material in unknown samples.

In a similar series of amplification reactions, this set of primers and probes were tested for amplifying and detecting 100 pg of DNA from *Staphylococcus aureus* Mu3 (also known as methicillin-resistant *Staphylococcus aureus*), *Staphylococcus aureus, Staphylococcus epidermidis, Streptococcus agalactiae, Streptococcus pyogenes,* and *Streptococcus pneumoniae,* alongside 10 pg of *E. coli* for comparison, and a no-template control (NTC), all in duplicate. It is noted that the tested bacteria include both Gram-positive and Gram-negative bacteria. Real-time amplification results are shown in Table 4 ("EP" refers to endpoint).

TABLE 4

| Sample | | $C_T$ | End Point (at c40) |
|---|---|---|---|
| *Staphylococcus aureus* Mu3 | 100 pg | 22.2 | 130832 |
| *Staphylococcus aureus* Mu3 | 100 pg | 21.7 | 136136 |
| *Staphylococcus aureus* | 100 pg | 21.8 | 124004 |
| *Staphylococcus aureus* | 100 pg | 21.8 | 135570 |
| *Staphylococcus epidermidis* | 100 pg | 19.0 | 132983 |
| *Staphylococcus epidermidis* | 100 pg | 18.9 | 144509 |

TABLE 4-continued

| Sample | | $C_T$ | End Point (at c40) |
|---|---|---|---|
| Streptococcus agalactiae | 100 pg | 20.2 | 116510 |
| Streptococcus agalactiae | 100 pg | 20.4 | 90608 |
| Streptococcus pyogenes | 100 pg | 21.0 | 135415 |
| Streptococcus pyogenes | 100 pg | 21.0 | 136506 |
| Streptococcus pneumonia | 100 pg | 21.3 | 141007 |
| Streptococcus pneumonia | 100 pg | 21.2 | 132592 |
| E. coli | 10 pg | 28.6 | 93763 |
| E. coli | 10 pg | 28.6 | 94028 |
| NTC | 0 | 35.9 | 55749 |
| NTC | 0 | 35.3 | 57366 |

In a further series of amplification reactions, sensitivity of the same set of primers and probe were tested for amplifying and detecting 1 pg or 10 pg of DNA (as indicated) from *Staphylococcus aureus* Mu3, *Staphylococcus aureus*, *Staphylococcus epidermidis*, *Streptococcus agalactiae*, *Streptococcus pyogenes*, *Streptococcus pneumoniae*, *Citrobacter koseri*, *Clostridium perfringens*, *Enterococcus faecalis*, *Klebsiella pneumoniae*, *Lactobacillus acidophilus*, *Listeria monocytogenes*, *Propionibacterium granulosum*, *Pseudomonas aeruginosa*, *Serratia marcescens*, and *Escherichia coli*, as compared to a no-template control (NTC). Real-time amplification results are shown in Table 5A (an asterisk denotes an outlier excluded from calculations of average and standard deviation (SD); "reaction" is abbreviate "rxn").

TABLE 5A

| Sample Name | $C_T$ | End Point (cycle 32) |
|---|---|---|
| Staphylococcus aureus Strain | 24.6 | 146298 |
| Mu3 (10 pg/rxn) | 24.0 | 150759 |
| | 23.9 | 144630 |
| | 23.9 | 160607 |
| Average | 24.1 | 150573 |
| SD | 0.3 | 7172 |
| Staphylococcus aureus Strain | 24.6 | 140140 |
| (10 pg/rxn) | 24.7 | 149047 |
| | 24.8 | 143579 |
| | 24.9 | 141319 |
| Average | 24.7 | 143521 |
| SD | 0.1 | 3950 |
| Staphylococcus epidermidis | 25.1 | 143624 |
| (10 pg/rxn) | 25.4 | 131812 |
| | 24.9 | 149217 |
| | 25.4 | 140835 |
| Average | 25.2 | 141372 |
| SD | 0.3 | 7264 |
| Streptococcus agalactiae | 23.6 | 154101 |
| (10 pg/rxn) | 23.6 | 162176 |
| | 23.3 | 155802 |
| | 22.9 | 174359 |
| Average | 23.3 | 161610 |
| SD | 0.3 | 9183 |
| Streptococcus pneumoniae | 20.2 | 231483 |
| (10 pg/rxn) | 24.8 | 150798 |
| | 24.7 | 143049 |
| | 24.9 | 143045 |
| Average | 23.7 | 167094 |
| SD | 2.3 | 43082 |
| Streptococcus pyogenes | 24.5 | 146391 |
| (10 pg) | 24.7 | 142812 |
| | 24.6 | 152659 |
| | 25.0 | 150118 |
| Average | 24.7 | 147995 |
| SD | 0.2 | 4309 |
| Citrobacter koseri | 21.5 | 180338 |
| (100 pg/rxn) | 21.2 | 174188 |
| | 21.2 | 173076 |
| | 32 * | 36959 |

TABLE 5A-continued

| Sample Name | $C_T$ | End Point (cycle 32) |
|---|---|---|
| Average | 21.3 | 175868 |
| SD | 0.2 | 3911 |
| Clostridium perfringens | 20.5 | 223840 |
| (100 pg/rxn) | 20.2 | 214568 |
| | 20.5 | 197004 |
| | 20.3 | 208528 |
| Average | 20.4 | 210985 |
| SD | 0.2 | 11249 |
| Enterococcus faecalis | 21.6 | 191301 |
| (100 pg/rxn) | 21.6 | 187678 |
| | 21.7 | 197721 |
| | 21.8 | 193930 |
| Average | 21.7 | 192658 |
| SD | 0.1 | 4238 |
| Klebsiella pneumoniae | 22.0 | 170031 |
| (100 pg/rxn) | 22.0 | 179388 |
| | 22.0 | 175661 |
| | 22.0 | 175162 |
| Average | 22.0 | 175060 |
| SD | 0.0 | 3847 |
| Lactobacillus acidophilus | 20.9 | 191479 |
| (100 pg/rxn) | 22.8 | 157107 |
| | 21.0 | 181977 |
| | 21.0 | 176702 |
| Average | 21.4 | 176816 |
| SD | 0.9 | 14492 |
| Listeria monocytogenes | 20.6 | 204487 |
| (100 pg/rxn) | 20.7 | 190711 |
| | 20.6 | 194739 |
| | 21.2 | 202970 |
| Average | 20.8 | 198227 |
| SD | 0.3 | 6592 |
| Propionibacterium granulosum | 28.0 | 89600 |
| (100 pg/rxn) | 27.6 | 101429 |
| | 27.6 | 97531 |
| | 27.5 | 93514 |
| Average | 27.7 | 95519 |
| SD | 0.2 | 5100 |
| Pseudomonas aeruginosa | 21.1 | 194285 |
| (100 pg/rxn) | 21.0 | 186576 |
| | 21.0 | 184570 |
| | 21.1 | 177176 |
| Average | 21.1 | 185652 |
| SD | 0.1 | 7033 |
| Serratia marcescens | 21.1 | 193938 |
| (100 pg/rxn) | 21.0 | 173987 |
| | 21.1 | 195749 |
| | 21.4 | 188730 |
| Average | 21.1 | 188101 |
| SD | 0.2 | 9868 |
| Escherichia coli | 21.5 | 167341 |
| (100 pg/rxn) | 21.4 | 190853 |
| | 21.4 | 194130 |
| | 21.5 | 172951 |
| Average | 21.4 | 181319 |
| SD | 0.1 | 13171 |
| NTC | 32.0 | 39254 |
| | 32.0 | 36797 |
| | 32.0 | 37280 |
| | 32.0 | 38202 |
| Average | 32.0 | 37883 |
| SD | 0.0 | 1084 |

Similar reactions were prepared to test amplification of DNA from *B. cereus* as template (100 pg), with separate reactions for *E. coli* template (100 pg) and no-template control for comparison. Real-time amplification results are shown in Table 5B.

TABLE 5B

| Sample Name | $C_T$ | End Point (cycle 32) |
|---|---|---|
| B. cereus | 22.0 | 97954 |
| (100 pg/rxn) | 21.9 | 92258 |
|  | 21.9 | 95435 |
|  | 21.8 | 97702 |
|  | 22.0 | 98468 |
|  | 21.9 | 97108 |
| Average | 21.9 | 96488 |
| SD | 0.1 | 2321 |
| E. coli | 26.3 | 61129 |
| (100 pg/rxn) | 26.3 | 58532 |
| Average | 26.3 | 59830 |
| SD | 0.0 | 1836 |
| NTC | 32.0 | 16770 |
|  | 32.0 | 18341 |
|  | 32.0 | 14549 |
| Average | 32.0 | 16445 |
| SD | 0.0 | 2681 |

Example 2: Comparison of Probe and Primer Sets

Real-time PCR reactions were prepared as in Example 1 for 100 pg of *Staphylococcus aureus*, 100 pg of *E. coli*, or a no template control (NTC), using one of three primer sets and corresponding probe(s) as indicated below. Primer set 1 consisted of a forward primer having sequence SEQ ID NO: 4 and two reverse primers, one having sequence SEQ ID NO: 5 and the other having sequence SEQ ID NO: 6. Amplification products of primer set 1 were detected with a mixture of three probes having sequences of SEQ ID NO: 11-13, each of which was detected independently based on association with a different reporter. Primer set 1 probes were designed to collectively detect a broad range of bacteria. SEQ ID NO: 12, for example, was designed to detect species other than *S. aureus* and *E. coli*. Final reagent concentrations for each primer set 1 amplification reaction were as follows: 1× Taqman Universal Master Mix II; 500 nM of each primer; and 500 nm of each probe. Primer set 2 consisted of a primer having sequence SEQ ID NO: 7 and a primer having sequence SEQ ID NO: 8. Amplification products of primer set 2 were detected with a mixture of two probes having sequences SEQ ID NO: 14-15, each of which was detected independently based on association with a different reporter. Primer set 2 probes were designed to collectively detect a broad range of bacteria, with SEQ ID NO: 14 designed to detect multiple Gram-negative bacteria (though not exclusively), and SEQ ID NO: 15 designed to detect multiple Gram-positive bacteria (though exclusively). Final reagent concentrations for each primer set 2 amplification reaction were as follows: 1× Taqman Universal Master Mix II; 500 nM of each primer; and 500 nm of each probe. Primer set 3 consisted of a primer pair as detailed in Example 1, the amplification products of which were detected with a probe having sequence SEQ ID NO: 16. The primer set 3 probe was designed to detect multiple bacteria. Final reagent concentrations for each primer set 3 amplification reaction were as follows: 1× Taqman Universal Master Mix II; 500 nM of each primer; 500 nm of the probe. PCR amplifications were performed according to TaqMan kit manufacturer recommendations (Life Technologies—Applied Biosystems, Carlsbad, Calif.). Each amplification was performed in duplicate for each template, and the $C_T$ of each ($C_T$ 1 and $C_T$ 2) are provided in Table 6. As indicated by Table 6, multiple probes produced results similar to those obtained for the probe-primer set described in Example 1.

Results for probe SEQ ID NO: 12 were as expected based on the sequences for which it was designed. Results for SEQ ID NO: 14-15 were as expected based on the sequences for which they were designed. For example, SEQ ID NO: 14 produced an early $C_T$ for *E. coli*, a Gram-negative bacteria. Also, SEQ ID NO: 15 produced the earliest $C_T$ for *S. aureus*, a Gram-positive bacteria, while also able to detect *E. coli*, though with a later $C_T$.

TABLE 6

| Probe | Template | Reporter | $C_T1$ | $C_T2$ | $C_T$ Mean | $C_T$ SD |
|---|---|---|---|---|---|---|
| SEQ ID NO: 11 | NTC | FAM | 32.3 | 35.9 | 34.1 | 2.6 |
|  | S. aureus | FAM | 24.0 | 24.1 | 24.1 | 0.1 |
|  | E. coli | FAM | 24.2 | 24.1 | 24.2 | 0.0 |
| SEQ ID NO: 12 | NTC | JOE | 36.0 | 40.0 | 36.0 | 2.8 |
|  | S. aureus | JOE | 40.0 | 40.0 | 40.0 | 0.0 |
|  | E. coli | JOE | 40.0 | 25.3 | 32.6 | 10.4 |
| SEQ ID NO: 13 | NTC | TAMARA | 33.3 | 37.0 | 35.2 | 2.6 |
|  | S. aureus | TAMARA | 25.1 | 25.2 | 25.2 | 0.1 |
|  | E. coli | TAMARA | 25.7 | 40.0 | 25.5 | 10.1 |
| SEQ ID NO: 14 | NTC | FAM | 35.5 | 36.0 | 35.7 | 0.3 |
|  | S. aureus | FAM | 40.0 | 40.0 | 40.0 | 0.0 |
|  | E. coli | FAM | 23.2 | 23.2 | 23.2 | 0.0 |
| SEQ ID NO: 15 | NTC | JOE | 36.1 | 34.1 | 35.1 | 1.4 |
|  | S. aureus | JOE | 23.5 | 23.5 | 23.5 | 0.0 |
|  | E. coli | JOE | 25.8 | 26.0 | 25.9 | 0.1 |
| SEQ ID NO: 16 | NTC | FAM | 37.1 | 36.9 | 37.0 | 0.1 |
|  | S. aureus | FAM | 22.4 | 22.4 | 22.4 | 0.0 |
|  | E. coli | FAM | 22.3 | 22.2 | 22.3 | 0.1 |

Example 3: Simulated Platelet Samples—No Signal from Human DNA

Figure 3A:
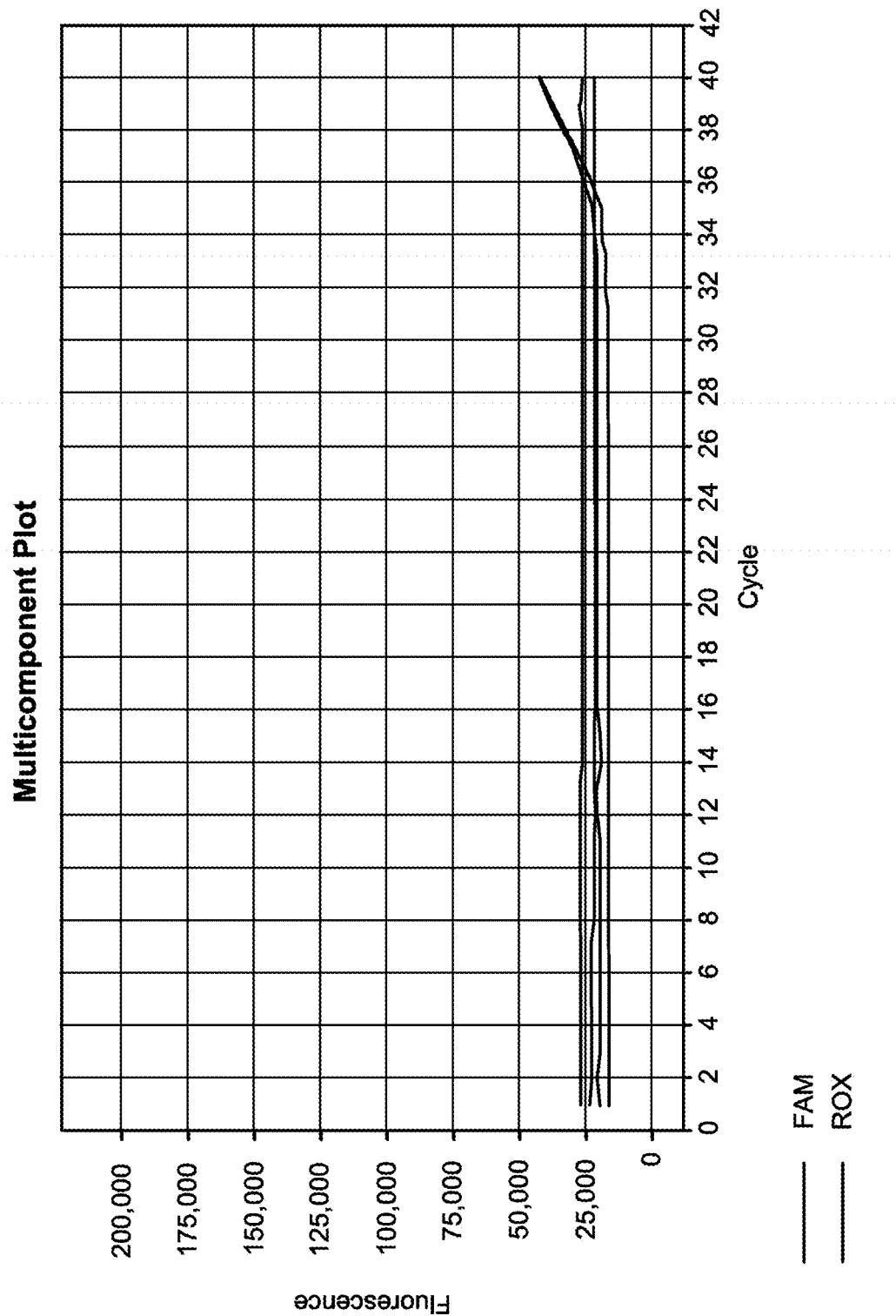
FIGS. 3A and 3B are graphs illustrating results of nucleic acid amplification reactions.
Figure 3B:
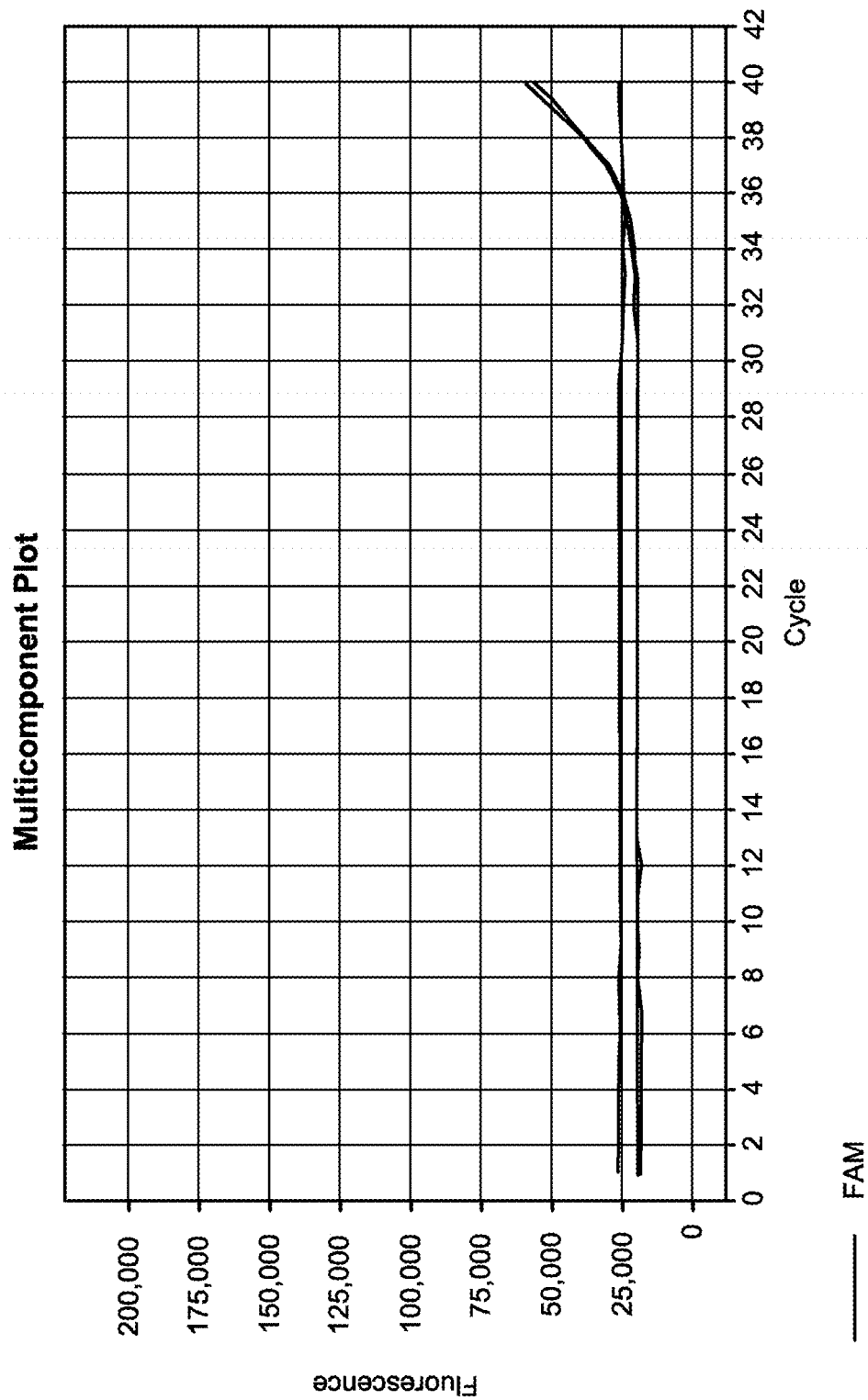

DNA extracted from a patient sample, such as a platelet sample, will typically include human genomic DNA. Accordingly, a sample set of primers and a probe were tested in an amplification reaction in the presence of human genomic DNA. Real-time PCR reactions were prepared as in Example 1, including the same primers and probe. However, instead of bacterial DNA, amplification reactions included 10 ng of human genomic DNA, or water as the no-template control, both in duplicate. A graphical display of the results of real-time PCR amplification for the human DNA and the no-template control are shown in FIGS. 3A and 3B, respectively. No amplification signal was obtained for the human DNA samples until around cycle 39 (FAM), indicating that the primers and probe are specific to bacterial sequences and would specifically amplify those sequences in a mixed sample containing human DNA. Moreover, the end-point signal intensity for the human DNA sample was actually lower than that of the no-template control, suggesting that human DNA in a sample may actually reduce formation of potentially non-specific amplification products at late cycles.

Example 4: Probe Set Comparison

Figure 4A:
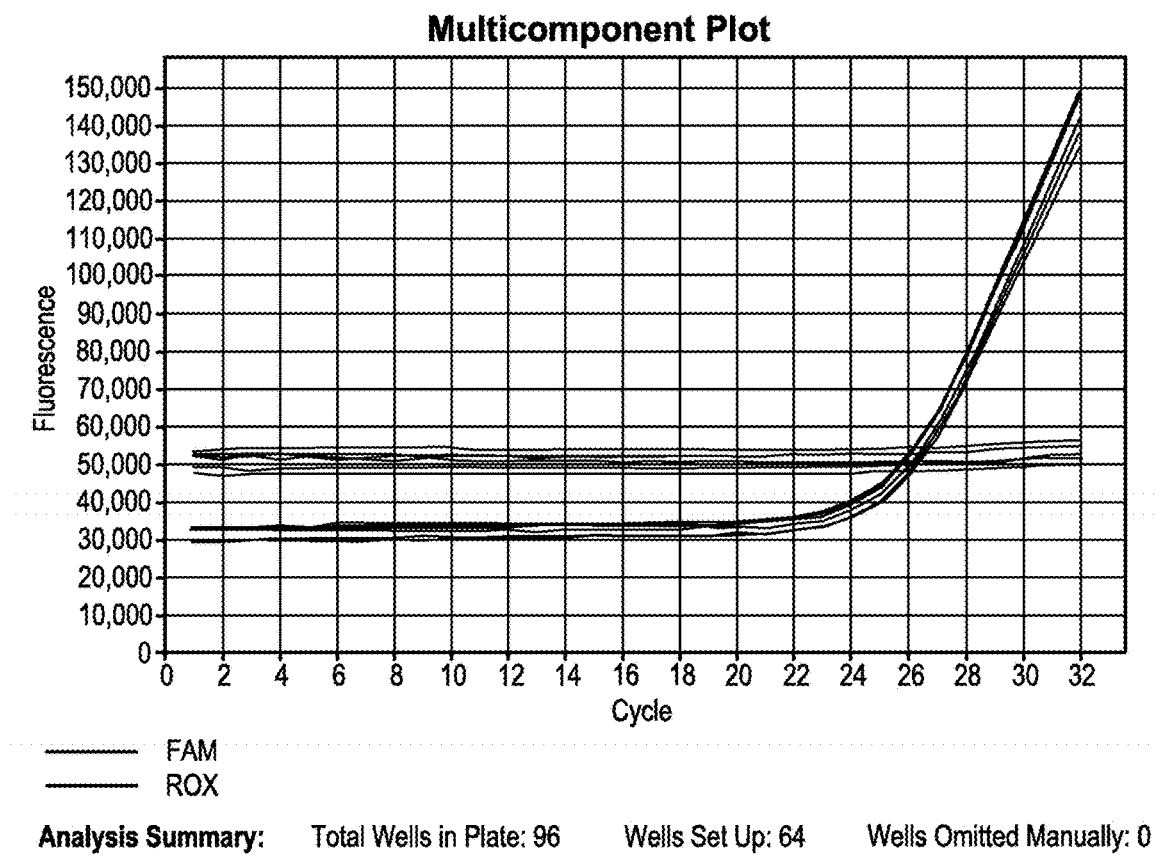
FIGS. 4A and 4B are graphs illustrating results of nucleic acid amplification reactions.
Figure 4A:
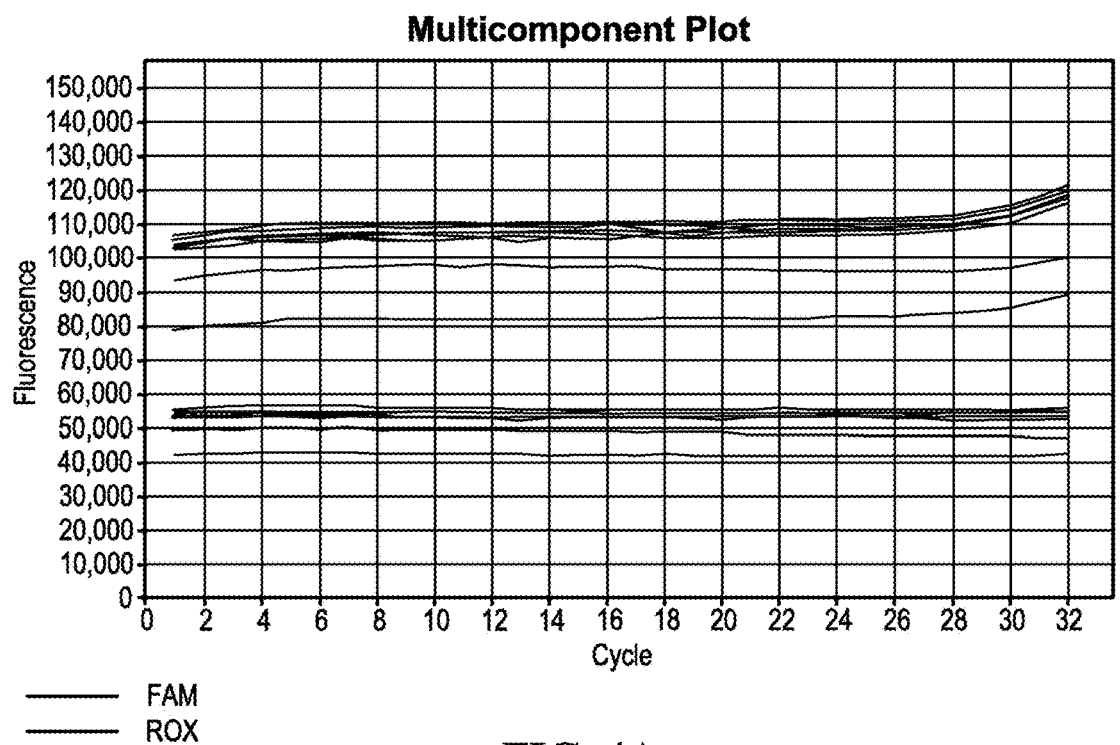
Figure 4B:
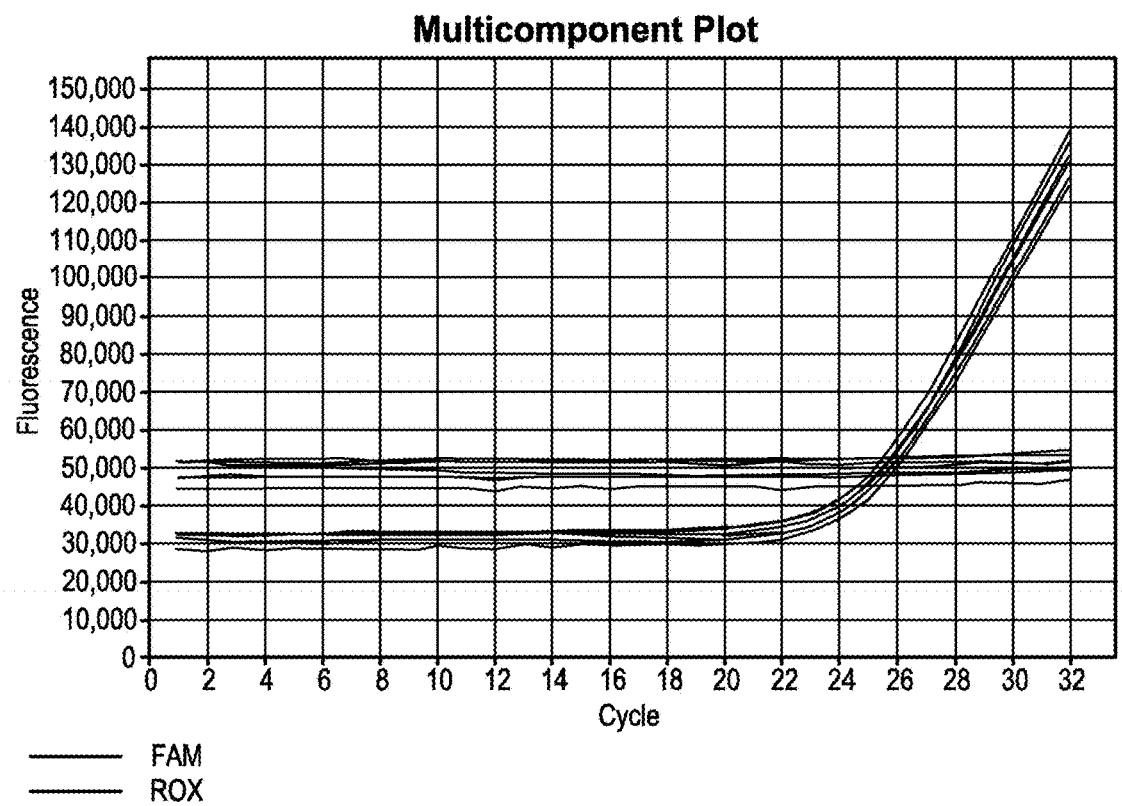
Figure 4B:
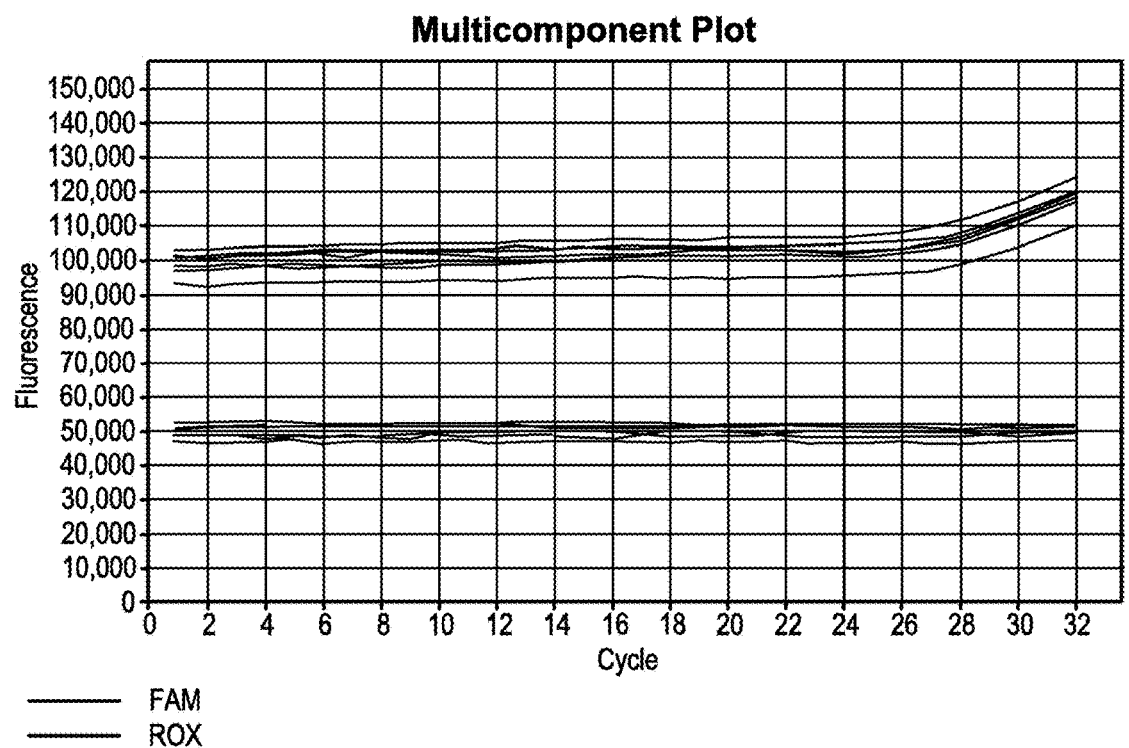

Examples 1-3 demonstrate the specificity and sensitivity of bacterial polynucleotide detection of primers and probes in accordance with the disclosure. In this example, the sensitivity of the primers and probes described in Example 1 (collectively, "Set 3") were compared to primers and probes described by Liu et al. (Chin. J. Blood Transfusion, September 2008, vol. 21, No. 9) and Nadkarni et al. (Microbiology (2002), 148, 257-266). Liu and Nadkarni describe use of primers having sequences SEQ ID NO: 17 (TCC-TACGGGAGGCAGCAGT) and SEQ ID NO: 18 (GGAC-TACCAGGGTATCTAATCCTGTT) to amplify a 466 bp region of bacterial 16S rRNA detected with a probe having sequence SEQ ID NO: 19 (CGTAT-TACCGCGGCTGCTGGCAC), collectively the "Liu Set." Nadkarni describes the manual selection of this large amplicon due to an inability to identify an amplicon having corresponding primer and probe target sequences sufficiently conserved across multiple bacteria. In a first comparison, detection efficiency is compared for real-time PCR amplification of 100 pg of *Staphylococcus aureus*, 100 pg of *E. coli*, or a no template control (NTC). The results for amplification and detection of 100 pg of *Staphylococcus aureus* are illustrated graphically in FIG. 4A, with results for Set 3 on the top and the Liu Set on the bottom. The results for amplification and detection of 100 pg of *E. coli* are illustrated graphically in FIG. 4B, with results for Set 3 on the top and the Liu Set on the bottom. The figures illustrate that detection using Set 3 is consistent and robust. Detection of even 100 pg with the Liu Set is weaker, occurs at a later $C_T$.

A second comparison repeated the above conditions for comparison of Set 3 to the Liu Set using a lower amount of target DNA. In this second comparison, only 10 pg of *E. coli* DNA were included in the reactions, which were run alongside no-template control reactions. Each reaction condition was run in duplicate. Real-time amplification results are shown in Table 7.

TABLE 7

| Primer/Probe | Sample | $C_T$ | End Point (at 40 cycles) |
|---|---|---|---|
| Set 3 | 10 pg *E coli* | 28.6 | 93763 |
| Set 3 | 10 pg *E coli* | 28.6 | 94028 |
| Set 3 | NTC | 35.9 | 55749 |
| Set 3 | NTC | 35.3 | 57366 |
| Liu Set | 10 pg *E coli* | 35.9 | 57975 |
| Liu Set | 10 pg *E coli* | 34.9 | 60091 |
| Liu Set | NTC | 40.0 | 51938 |
| Liu Set | NTC | 40.0 | 52522 |

The results in Table 7 second comparison illustrate that the Liu Set is not sufficiently sensitive to distinguish 10 pg of bacterial DNA from a no-template control, and is therefore inadequate for detecting contamination at such a low level. In contrast, the $C_T$ for 10 pg of DNA using Set 3 is about seven cycles earlier than that of the no-template control, indicating a substantially increased sensitivity for bacterial DNA. Without wishing to be bound by theory, it is possible that the shorter amplicon (about 143 bp for Set 3, corresponding to SEQ ID NO: 3; compared to about 466 bp for the Liu Set) and/or lower variability within the amplicon for Set 3 improved sensitivity of the assay. Other potentially contributing factors to the lower sensitivity of the Liu Set include relatively stable homodimerization of SEQ ID NO: 17 primer (FIG. 6A), and hybridization between this primer and the SEQ ID NO: 19 probe (FIG. 6B). To evaluate primer-primer, and primer-probe hybridization, dimer formation was tested using OligoAnalyzer 3.1 (www.idtdna.com/analyzer/Applications/OligoAnalyzer/), using default settings (target type—DNA; oligo concentration—0.25 µM; Na$^+$ conc.—50 mM; Mg$^{++}$ conc.—0 mM; dNTPs conc.—0 mM). Given the results of Nadkarni, it was both surprising and unexpected that primers and probes to a 16S rRNA target sequence could provide such sensitivity and specificity across multiple bacterial species and genera.

Example 4: Effects of Different Quenchers

Because the reaction conditions used in Example 4 and those used in Liu were comparable, possible effects from the use of different quenchers was tested. The Set 3 probe in Example 3 used a Zen™ internal quencher (Integrated DNA Technologies, Inc.; Coralville, Iowa), while the Liu Set probe used a 3'-terminal Iowa Black® quencher (Integrated DNA Technologies, Inc.; Coralville, Iowa), the original position used by Liu et al. To test the effect of different quenchers, real-time PCR reactions were prepared as in Example 1 using Set 3 primers and the corresponding FAM-labeled probe with either the Zen quencher or the 3'-terminal Iowa Black quencher. These primer-probe combinations were tested for detection of a range of amounts of *E. coli* DNA, as indicated below. A reaction for each template was prepared in duplicate. Real-time amplification results are shown in Table 8. As shown by the comparable results across quenchers, the difference in quencher used does not account for the difference in sensitivity.

TABLE 8

| | IowaBlack quencher | | Zen quencher | |
|---|---|---|---|---|
| Sample | $C_T$ | End Point (at c40) | $C_T$ | End Point (at c40) |
| NTC | 34.2 | 98878 | 35.6 | 60455 |
| | 37.8 | 104367 | 35.7 | 56212 |
| Human 10 ng | 33.6 | 145891 | 35.9 | 42360 |
| | 36.9 | 118112 | 35.0 | 41708 |
| *E. coli* 0.1 pg | 31.7 | 127209 | 30.7 | 92871 |
| | 31.6 | 149883 | 40.0 | −1234 |
| *E. coli* 1 pg | 27.5 | 91051 | 27.3 | 102092 |
| | 28.8 | 115428 | 27.1 | 105463 |
| *E. coli* 10 pg | 24.8 | 199150 | 24.0 | 128770 |
| | 24.7 | 206550 | 23.9 | 130361 |
| *E. coli* 100 pg | 21.0 | 206526 | 20.3 | 134254 |
| | 21.1 | 204175 | 20.3 | 136525 |
| *E. coli* 1 ng | 17.5 | 194156 | 17.0 | 149226 |
| | 17.4 | 211131 | 16.9 | 147917 |
| *E. coli* 10 ng | 13.8 | 204532 | 13.3 | 133282 |
| | 13.9 | 193499 | 13.8 | 88670 |

Example 5: Detecting *S. simulans* in Platelet Samples

Figure 7A:
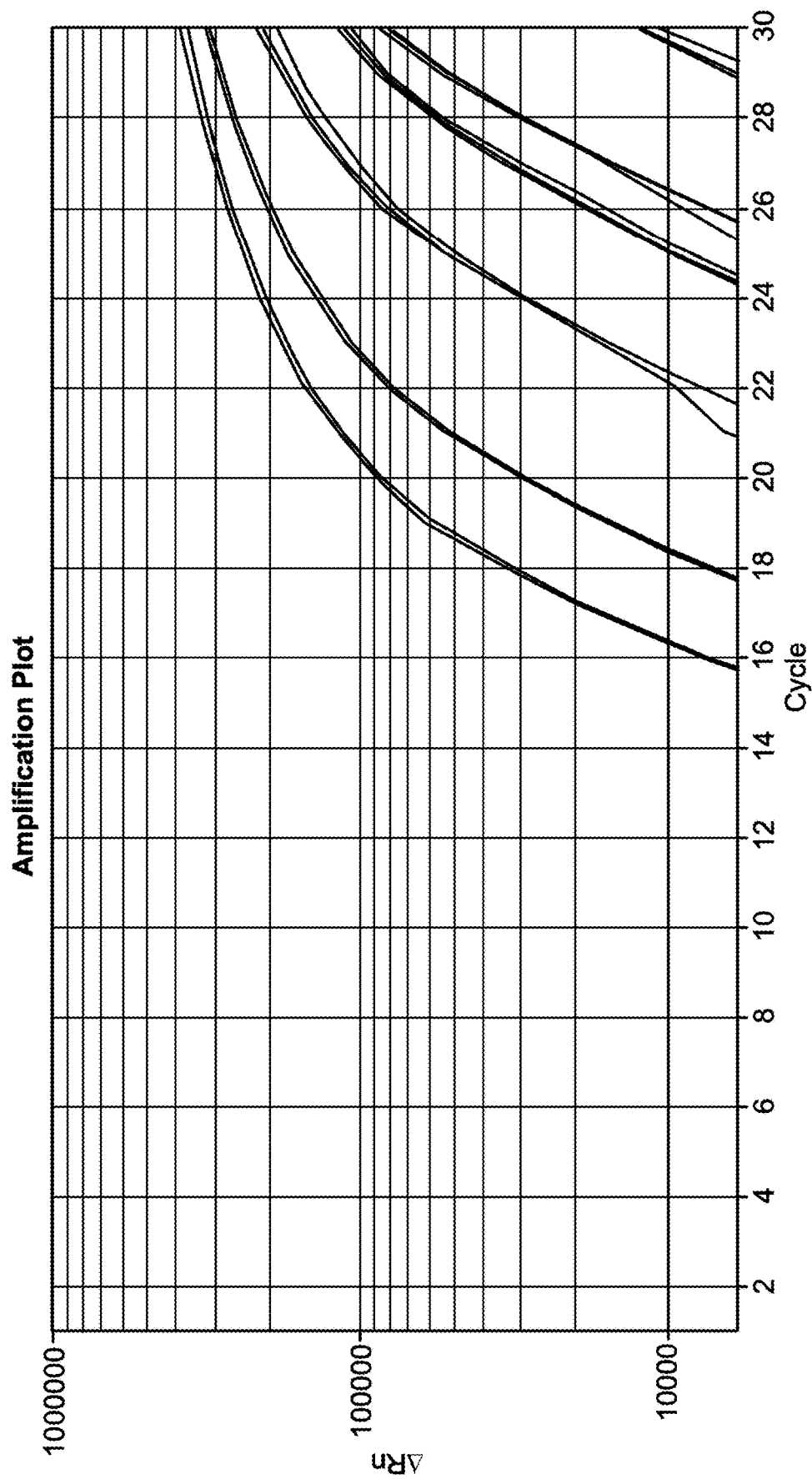
FIG. 7A is a graph illustrating results of nucleic acid amplification reactions.
Figure 7B:
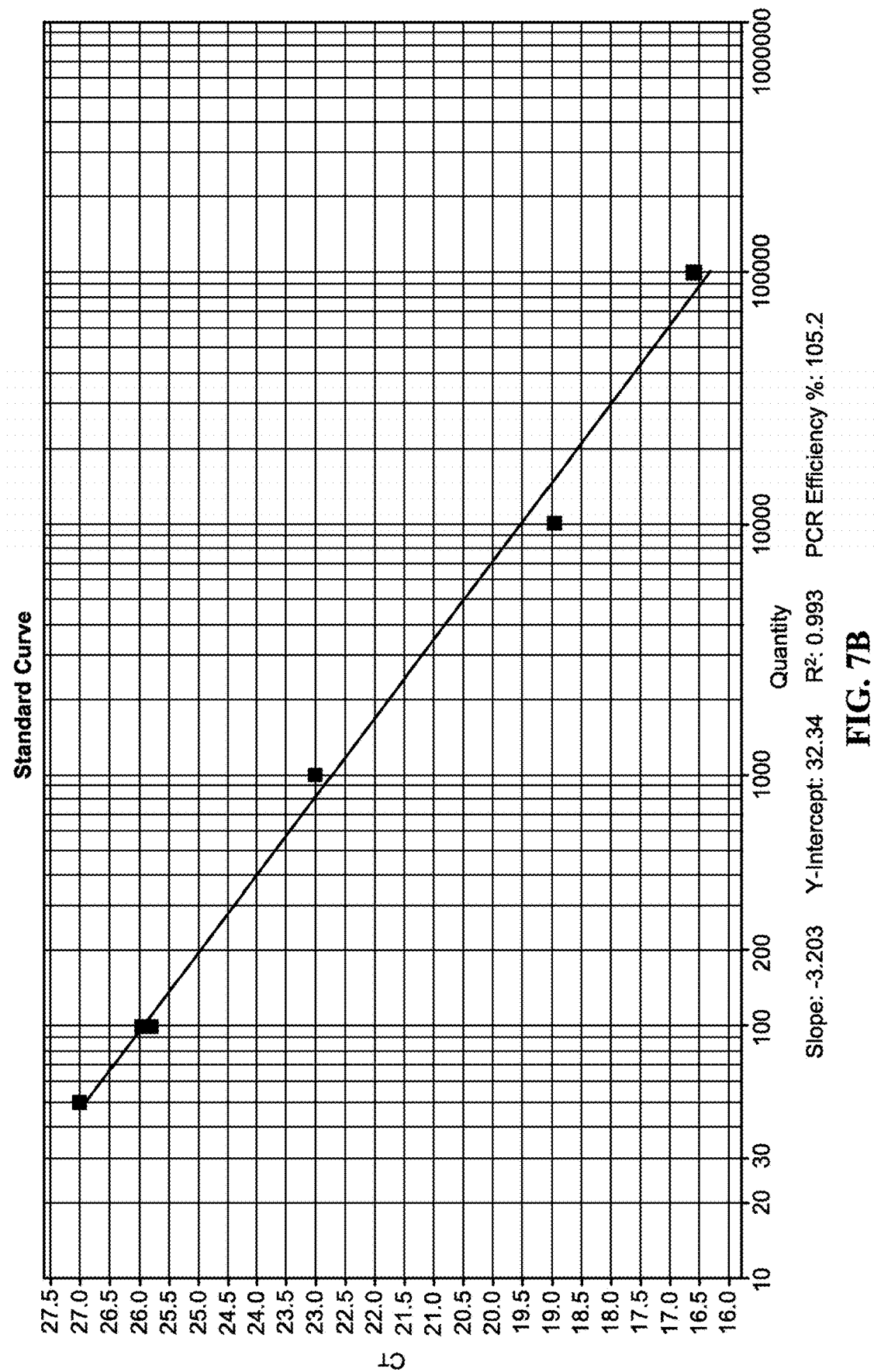
FIG. 7B is graph illustrating the detection range of a nucleic acid amplification assay.
Figure 8A:
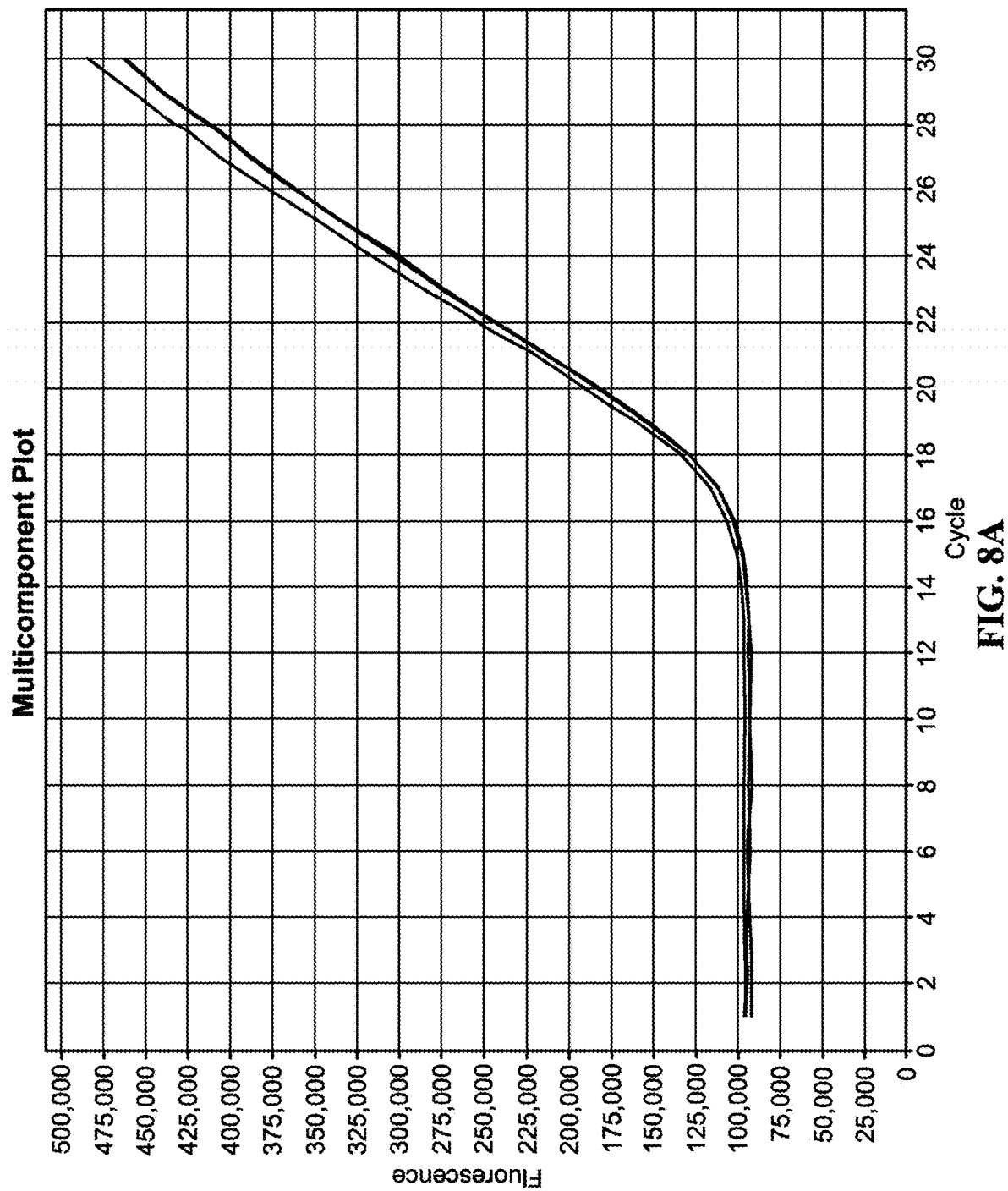
FIGS. 8A-G are graphs illustrating results of nucleic acid amplification reactions.
Figure 8B:
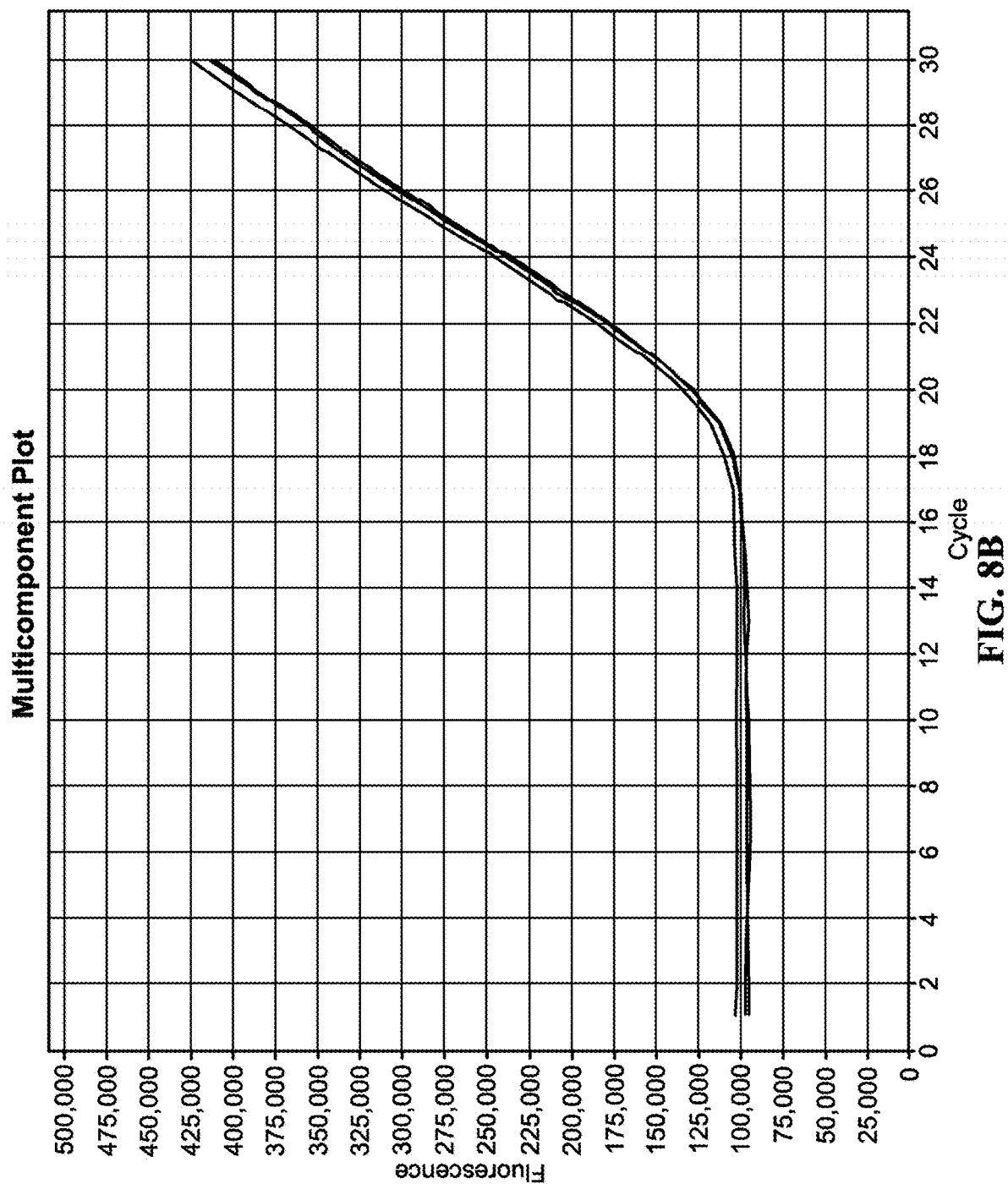
Figure 8C:
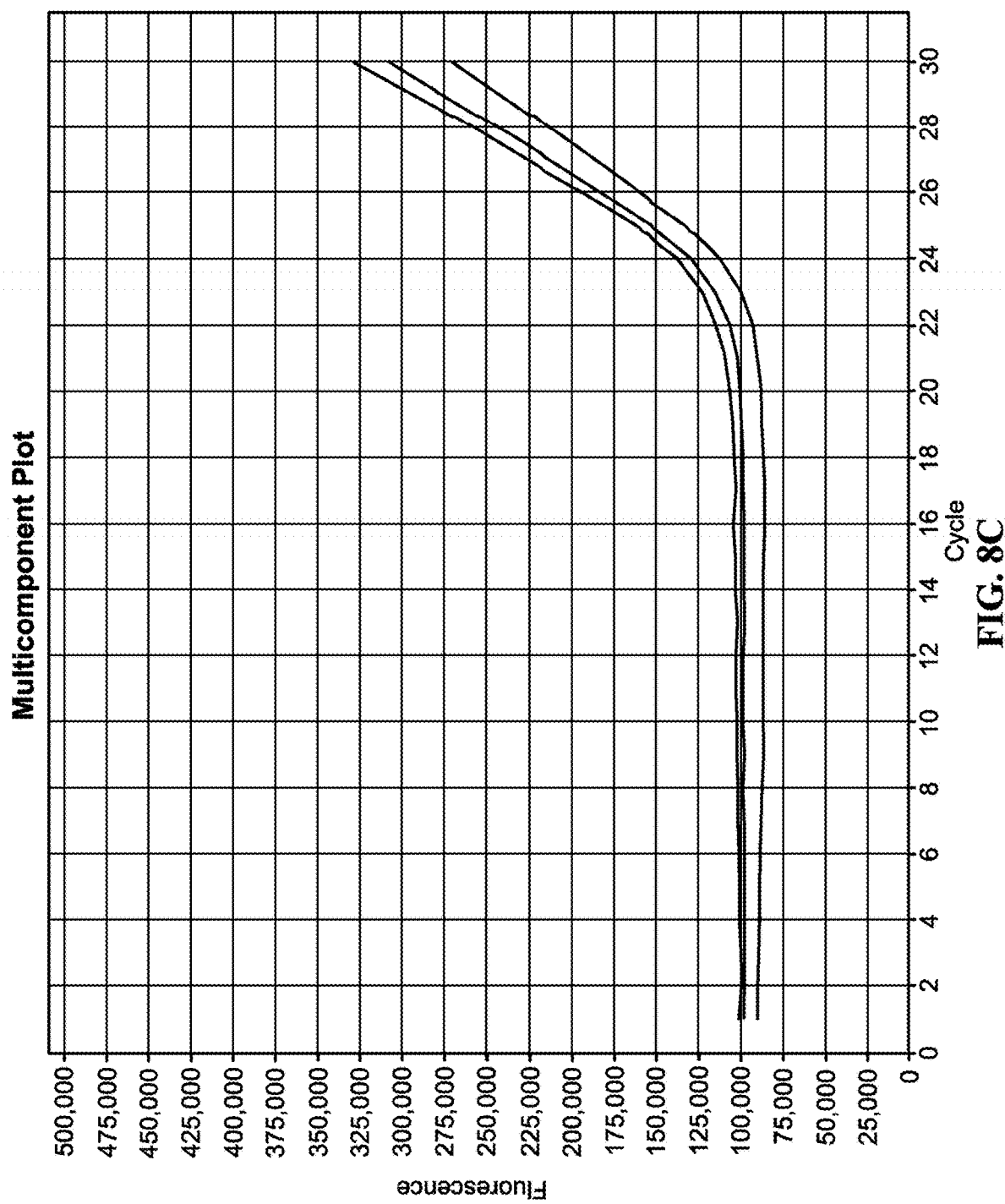
Figure 8D:
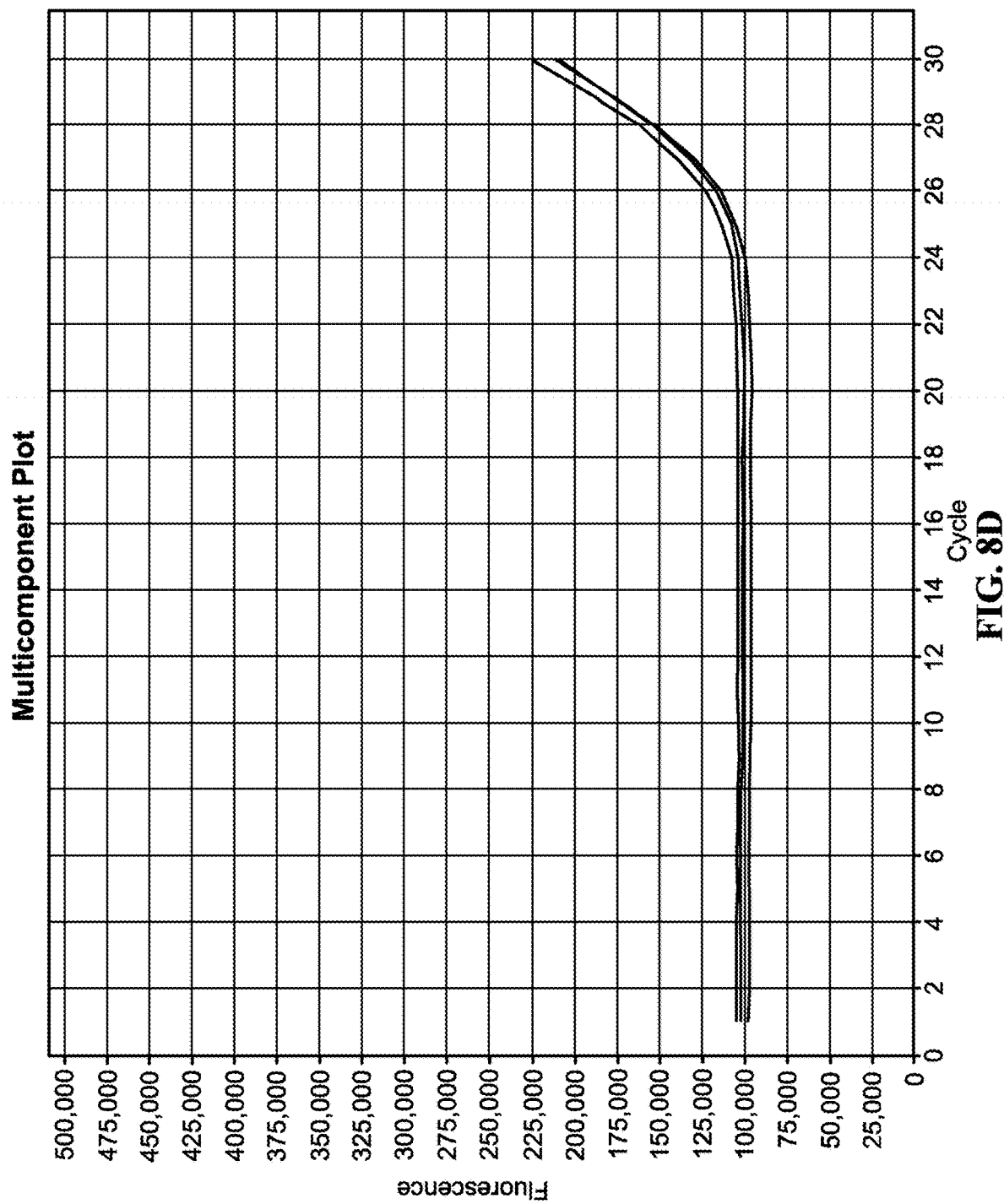
Figure 8E:
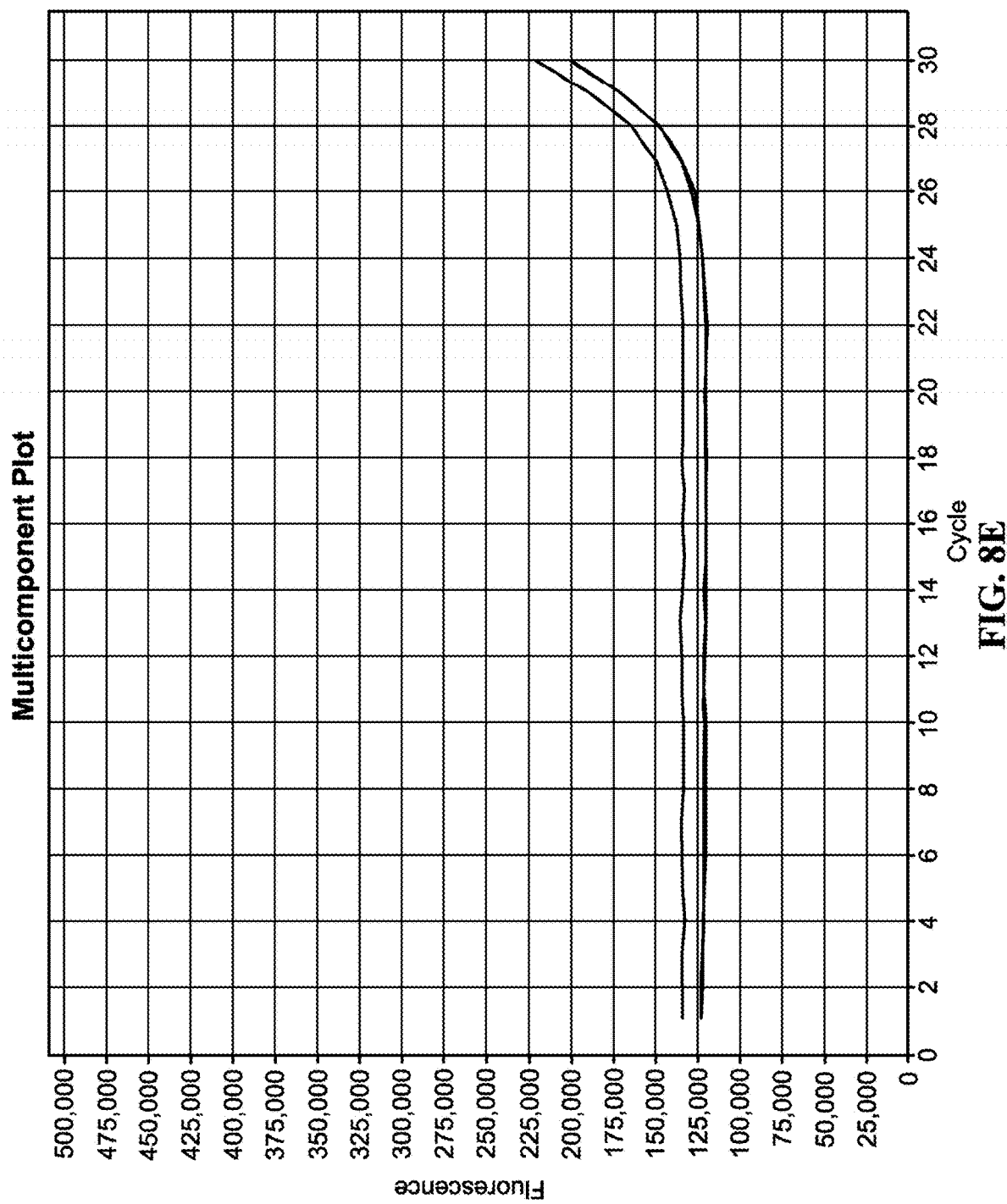
Figure 8F:
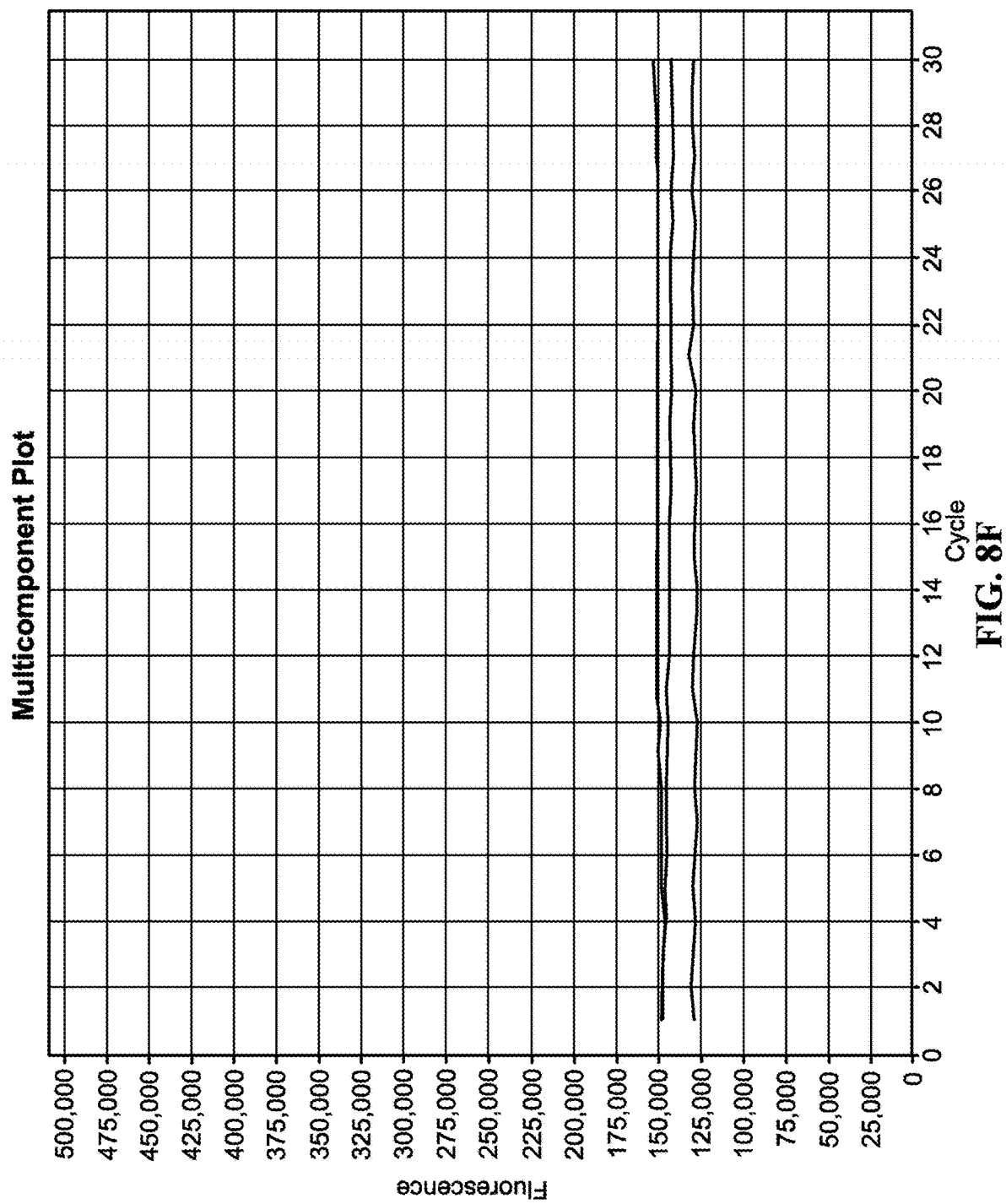
Figure 8G:
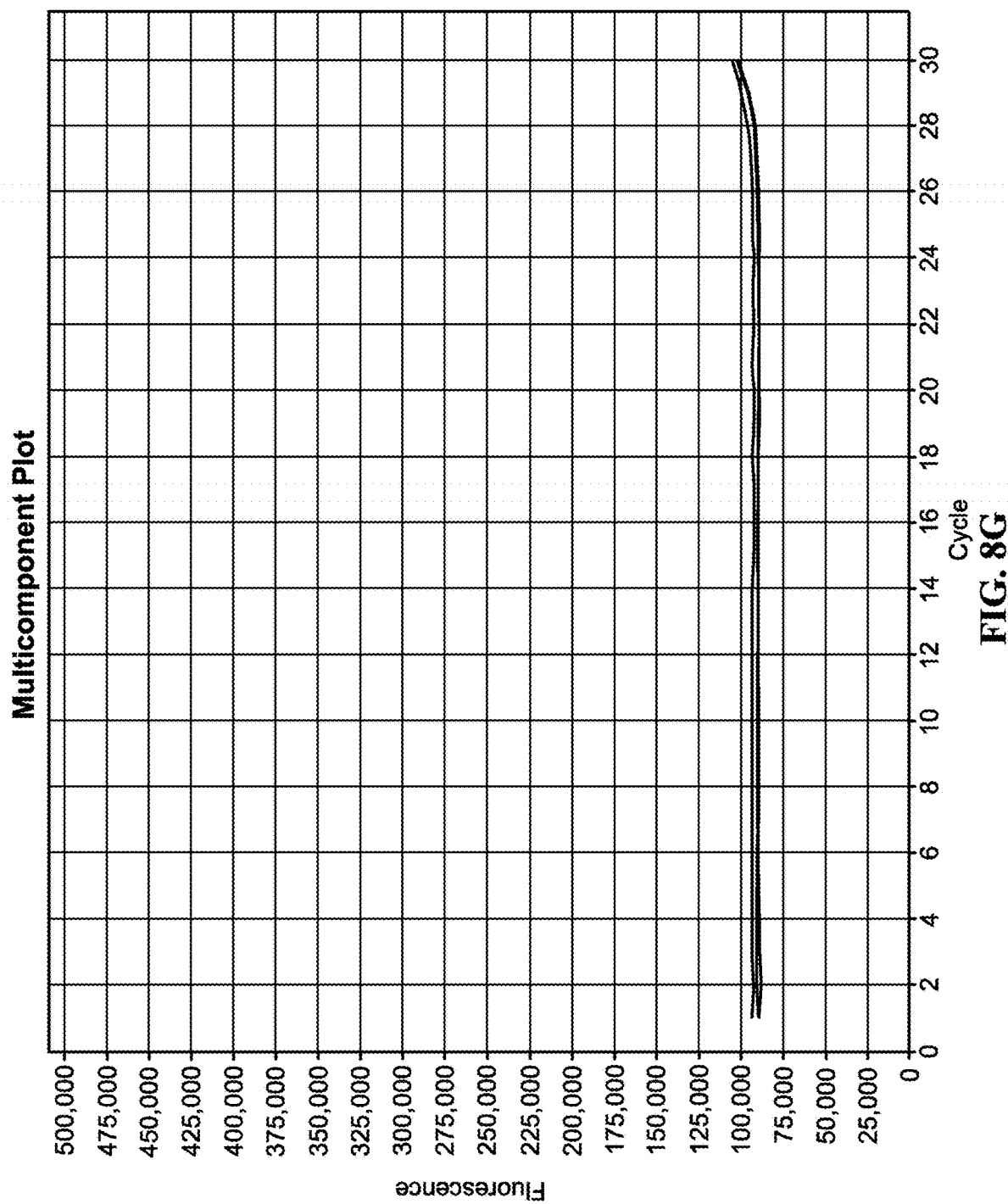

*Staphylococcus simulans* were cultured in ATCC Nutrient Broth at 37° C. overnight. Cultures were diluted with pure water and plated on nutrient agar plates, and live colonies were counted after 37° C. incubation overnight in order to determine the concentration of colony forming units (cfu). An *S. simulans* culture was titrated and normalized into 54 of pure water to produce 54 samples having 100000, 10000, 1000, 100, 50, 25, or 0 cfu. The 0 cfu sample was water only, and used as a negative control. Each of these 5 µL bacterial samples was then added to 1954 of salvaged human platelets, collected by apheresis six days earlier. The effective cfu/mL for these was 500000, 50000, 5000, 500, 250, 125, and 0, respectively. DNA was extracted from the 2004 samples using GeneJET Genomic DNA Purification Kit (Thermo Scientific), with DNA eluted into 454 elution buffer. 30-cycle, real-time PCR reactions were prepared and run in triplicate using the probes and primers as in Example 1, and approximately 14 uL of each elution, such that the number of cfu per reaction was about 31250, 3125, 312.5, 31.3, 15.6, 7.6, and 0, respectively. Reactions also contained GoTaq MDx Hot Start Polymerase (Promega), and performed using a Step One Plus real time PCR machine (Life Technologies). A graph of resulting amplification curves is provided in FIG. 7A, with each square along the x-axis representing two cycles. The groups of curves from left to right correspond to 31250, 31250, 3125, 312.5, 31.3, and 15.6, with 7.6 and 0 at the far right. The limit of detection for this experiment was thus at least down to 15.6 cfu, with an average $C_T$ of about 26.9. FIG. 7A graphically illustrates the quantitative linearity under these conditions. Separate amplification curves for 31250, 31250, 3125, 312.5, 31.3, 15.6, 7.6, and 0 cfu per reaction are illustrated in FIGS. 8A-G, respectively. Real-time amplification results are also summarized in Table 9. The results for *S. simulans* titrations were similar to those obtained in the above examples using DNA spike-in procedures. PCR amplification efficiency was high, and no non-specific amplification results were observed.

TABLE 9

| CFU/PCR rxn | Ct | Endpoint (at c30) |
|---|---|---|
| 31250.0 | 16.66 | 484371 |
| 31250.0 | 16.54 | 461482 |
| 31250.0 | 16.66 | 462721 |
| Average | 16.62 | |
| SD | 0.07 | |
| 3125.0 | 18.97 | 413503 |
| 3125.0 | 18.95 | 410119 |
| 3125.0 | 18.95 | 424044 |
| Average | 18.96 | |
| SD | 0.01 | |
| 312.5 | 23.05 | 270307 |
| 312.5 | 22.97 | 308094 |
| 312.5 | 22.97 | 329002 |
| Average | 23.00 | |
| SD | 0.05 | |
| 31.3 | 25.80 | 209835 |
| 31.3 | 25.75 | 223255 |
| 31.3 | 25.97 | 207997 |
| Average | 25.84 | |
| SD | 0.12 | |
| 15.6 | 27.04 | 200854 |
| 15.6 | 26.97 | 222568 |
| 15.6 | 26.96 | 200467 |
| Average | 26.99 | |
| SD | 0.04 | |
| 7.6 | 30.00 | 131392 |
| 7.6 | 30.00 | 144039 |
| 7.6 | 30.00 | 154508 |
| Average | 30.00 | |
| SD | 0.00 | |
| Platelet only Control | | |
| 0.0 | 30.00 | 102501 |
| 0.0 | 30.00 | 102101 |
| 0.0 | 30.00 | 105075 |
| Average | 30.00 | |
| SD | 0.00 | |

Example 6: Detecting Multiple Different Live Bacteria in Platelet Samples

Bacterial samples were prepared for the 18 bacterial species listed in Table 10, and combined with salvaged platelets, as in Example 5. For samples containing bacteria 1-12 in Table 10, and for 12 platelet-only samples, DNA was extracted using a Maxwell 16 MDx Instrument (Promega) and Maxwell 16 LEV Blood DNA kit (Promega). For samples containing bacteria 13-18 in Table 10, and for 6 platelet-only samples, DNA was manually extracted using GeneJET Genomic DNA Purification Kit (Thermo Scientific). 30-cycle, real-time PCR reactions were prepared in triplicate, and run as in Example 5 (using probes and primers as in Example 1). Results, including the number of cfu per reaction, are provided in Table 11. 72 platelet samples in all were tested. For all samples containing bacteria, a positive signal was detected, while no positive signal was detected for the platelet-only controls. Thus, the assay was 100% sensitive and 100% specific under these complex-mixture conditions.

TABLE 10

| | Bacteria | Vendor | Item Number |
|---|---|---|---|
| 1 | *Listeria monocytogenes* | ATCC | ATCC 19115 |
| 2 | *Enterococcus faecalis* | ATCC | ATCC 19433 |
| 3 | *Staphylococcus aureus* Mu50 | ATCC | ATCC 700699 |
| 4 | *Citrobacter koseri* | ATCC | ATCC BAA-895 |
| 5 | *Klebsiella pneumoniae* | ATCC | ATCC 700603 |
| 6 | *Pseudomonas aeruginosa* | ATCC | ATCC 10145 |
| 7 | *Escherichia coli* | ATCC | ATCC 700928 |
| 8 | *Streptococcus pyogenes* | ATCC | ATCC 49399 |
| 9 | *Streptococcus pneumoniae* | ATCC | ATCC 6301 |
| 10 | *Streptococcus agalactiae* | ATCC | ATCC BAA-611 |
| 11 | *Yersinia enterocolitica* | ATCC | ATCC 23715 |
| 12 | *Staphylococcus epidermidis* | ATCC | ATCC 12228 |
| 13 | *Staphylococcus simulans* | ATCC | ATCC 11631 |
| 14 | *Micrococcus luteus* | ATCC | ATCC 4698 |
| 15 | *Enterobacter aerogenes* | ATCC | ATCC 13048 |
| 16 | *Bacillus cereus* | ATCC | ATCC 14893 |
| 17 | *Serratia marcescens* | ATCC | ATCC 8100 |
| 18 | *Lactobacillus acidophilus* | ATCC | ATCC 4356 |

TABLE 11

| Sample | cfu/PCR rxn | $C_T$ | Endpoint cycle 30 |
|---|---|---|---|
| Platelets only | 0.0 | 30.0 | 162459 |
| Platelets only | 0.0 | 30.0 | 156179 |
| Platelets only | 0.0 | 30.0 | 158632 |
| Platelets only | 0.0 | 30.0 | 169799 |
| Platelets only | 0.0 | 30.0 | 164256 |
| Platelets only | 0.0 | 30.0 | 176073 |
| Average | | 30.0 | |
| SD | | 0.0 | |
| *Listeria monocytogenes* | 40,000 | 26.1 | 299936 |
| *Listeria monocytogenes* | 40,000 | 26.0 | 326216 |
| *Listeria monocytogenes* | 40,000 | 26.2 | 288790 |
| Average | | 26.1 | |
| SD | | 0.1 | |
| *Enterococcus faecalis* | 40,000 | 21.4 | 489164 |
| *Enterococcus faecalis* | 40,000 | 21.4 | 583293 |
| *Enterococcus faecalis* | 40,000 | 21.3 | 556506 |
| Average | | 21.3 | |
| SD | | 0.1 | |
| *Staphylococcus aureus* | 40,000 | 23.7 | 394106 |
| *Staphylococcus aureus* | 40,000 | 23.1 | 412728 |
| *Staphylococcus aureus* | 40,000 | 23.1 | 428943 |
| Average | | 23.3 | |
| SD | | 0.4 | |
| *Citrobacter koseri* | 40,000 | 22.0 | 504943 |
| *Citrobacter koseri* | 40,000 | 22.2 | 475522 |
| *Citrobacter koseri* | 40,000 | 22.0 | 503508 |
| Average | | 22.0 | |
| SD | | 0.1 | |
| *Klebsiella pneumoniae* | 40,000 | 22.4 | 494191 |
| *Klebsiella pneumoniae* | 40,000 | 22.3 | 494349 |
| *Klebsiella pneumoniae* | 40,000 | 22.3 | 486965 |
| Average | | 22.3 | |
| SD | | 0.1 | |
| *Pseudomonas aeruginosa* | 40,000 | 24.8 | 352654 |
| *Pseudomonas aeruginosa* | 40,000 | 24.3 | 396813 |
| *Pseudomonas aeruginosa* | 40,000 | 24.2 | 383947 |
| Average | | 24.5 | |
| SD | | 0.3 | |
| *Escherichia coli* | 40,000 | 21.6 | 498716 |
| *Escherichia coli* | 40,000 | 21.4 | 589153 |
| *Escherichia coli* | 40,000 | 21.5 | 554276 |
| Average | | 21.5 | |
| SD | | 0.1 | |
| Platelets only | 0.0 | 30.0 | 167773 |
| Platelets only | 0.0 | 30.0 | 155873 |
| Platelets only | 0.0 | 30.0 | 157417 |
| Platelets only | 0.0 | 30.0 | 165834 |

TABLE 11-continued

| Sample | cfu/PCR rxn | $C_T$ | Endpoint cycle 30 |
|---|---|---|---|
| Platelets only | 0.0 | 30.0 | 168972 |
| Platelets only | 0.0 | 30.0 | 173085 |
| Average | | 30.0 | |
| SD | | 0.0 | |
| Streptococcus pyogenes | 40,000 | 14.4 | 762017 |
| Streptococcus pyogenes | 40,000 | 14.3 | 739994 |
| Streptococcus pyogenes | 40,000 | 14.4 | 671678 |
| Average | | 14.4 | |
| SD | | 0.0 | |
| Streptococcus pneumoniae | 40,000 | 14.6 | 711581 |
| Streptococcus pneumoniae | 40,000 | 14.6 | 785952 |
| Streptococcus pneumoniae | 40,000 | 14.5 | 740601 |
| Average | | 14.6 | |
| SD | | 0.0 | |
| Streptococcus agalactiae | 40,000 | 17.2 | 554329 |
| Streptococcus agalactiae | 40,000 | 17.0 | 606164 |
| Streptococcus agalactiae | 40,000 | 16.8 | 629203 |
| Average | | 17.0 | |
| SD | | 0.2 | |
| Yersinia enterocolitica | 40,000 | 20.3 | 445063 |
| Yersinia enterocolitica | 40,000 | 19.7 | 502767 |
| Yersinia enterocolitica | 40,000 | 20.3 | 480745 |
| Average | | 20.1 | |
| SD | | 0.4 | |
| Staphylococcus epidermidis | 40,000 | 20.0 | 533739 |
| Staphylococcus epidermidis | 40,000 | 20.0 | 473550 |
| Staphylococcus epidermidis | 40,000 | 19.6 | 454904 |
| Average | | 19.9 | |
| SD | | 0.2 | |
| Platelets only | 0 | 30.0 | 126143 |
| Platelets only | 0 | 30.0 | 94014 |
| Platelets only | 0 | 30.0 | 73297 |
| Platelets only | 0 | 30.0 | 141745 |
| Platelets only | 0 | 30.0 | 118017 |
| Platelets only | 0 | 30.0 | 77828 |
| Average | | 30.0 | |
| SD | | 0.0 | |
| Staphylococcus simulans | 3125 | 18.97 | 413503 |
| Staphylococcus simulans | 3125 | 18.95 | 410119 |
| Staphylococcus simulans | 3125 | 18.95 | 424044 |
| Average | | 19.0 | |
| SD | | 0.0 | |
| Micrococcus luteus | 25000 | 26.1 | 190927 |
| Micrococcus luteus | 25000 | 25.5 | 205158 |
| Micrococcus luteus | 25000 | 25.4 | 211896 |
| Average | | 25.7 | |
| SD | | 0.4 | |
| Enterobacter aerogenes | 2500 | 21.7 | 264655 |
| Enterobacter aerogenes | 2500 | 21.7 | 270156 |
| Enterobacter aerogenes | 2500 | 21.5 | 299383 |
| Average | | 21.6 | |
| SD | | 0.1 | |
| Bacillus cereus | 2500 | 12.9 | 464940 |
| Bacillus cereus | 2500 | 13.1 | 500024 |
| Bacillus cereus | 2500 | 12.8 | 493522 |
| Average | | 12.9 | |
| SD | | 0.1 | |
| Serratia marcescens | 2500 | 21.1 | 280877 |
| Serratia marcescens | 2500 | 21.1 | 275083 |
| Serratia marcescens | 2500 | 21.2 | 276654 |
| Average | | 21.1 | |
| SD | | 0.1 | |
| Lactobacillus acidophilus | 2500 | 23.1 | 254082 |
| Lactobacillus acidophilus | 2500 | 22.9 | 290639 |
| Lactobacillus acidophilus | 2500 | 23.1 | 289580 |
| Average | | 23.1 | |
| SD | | 0.1 | |

Example 7: Detecting Contamination by Live Bacteria in Whole Blood and Buffy Coats Salvaged whole blood and buffy coat samples were obtained from the Stanford Blood Center. Samples were spiked with either *E. coli* bacteria (as in Example 5) or with *E. coli* DNA. DNA was extracted from the spiked samples using the DNeasy Blood & Tissue Kit (Qiagen). 40-cycle, real-time PCR reactions were prepared and run in triplicate using the probes and primers as in Example 1, with either $10^4$ cfu per reaction, or 10 pg bacterial DNA per reaction. Real-time PCR was performed using a Step One Plus real time PCR machine (Life Technologies), as in Example 5 (using probes and primers as in Example 1). Results for spiked whole blood samples and spiked buffy coat samples are provided in Tables 12 and 13, respectively. The contamination was detected even at these low levels, indicating this method can be used for early detection of sepsis.

TABLE 12

| Sample Name | cfu/PCR rxn | $C_T$ | Endpoint cycle 30 |
|---|---|---|---|
| Whole blood with live *E. coli* | $10^4$ | 22.1 | 386844 |
| Whole blood with live *E. coli* | $10^4$ | 22.3 | 430218 |
| Whole blood with live *E. coli* | $10^4$ | 21.6 | 451450 |
| Average | | 22.0 | |
| SD | | 0.3 | |

| Sample Name | pg/PCR rxn | $C_T$ | Endpoint cycle 30 |
|---|---|---|---|
| Whole blood with *E. coli* DNA | 10 pg | 17.4 | 592123 |
| Whole blood with *E. coli* DNA | 10 pg | 17.5 | 577167 |
| Whole blood with *E. coli* DNA | 10 pg | 17.8 | 582917 |
| Average | | 17.5 | |
| SD | | 0.2 | |

TABLE 13

| Sample Name | cfu/PCR rxn | $C_T$ | Endpoint cycle 30 |
|---|---|---|---|
| Buffy coat with live *E. coli* | $10^4$ | 24.1 | 320830 |
| Buffy coat with live *E. coli* | $10^4$ | 23.0 | 362016 |
| Buffy coat with live *E. coli* | $10^4$ | 22.8 | 380865 |
| Average | | 23.3 | |
| SD | | 0.7 | |

| Sample Name | pg/PCR rxn | $C_T$ | Endpoint cycle 30 |
|---|---|---|---|
| Buffy coat with *E. coli* DNA | 10 pg | 17.9 | 537282 |
| Buffy coat with *E. coli* DNA | 10 pg | 18.0 | 586124 |
| Buffy coat with *E. coli* DNA | 10 pg | 17.6 | 599668 |
| Average | | 17.8 | |
| SD | | 0.2 | |

Example 8: DNA Titration and Detection of *S. aureus* DNA in Platelet Samples

Figure 9:
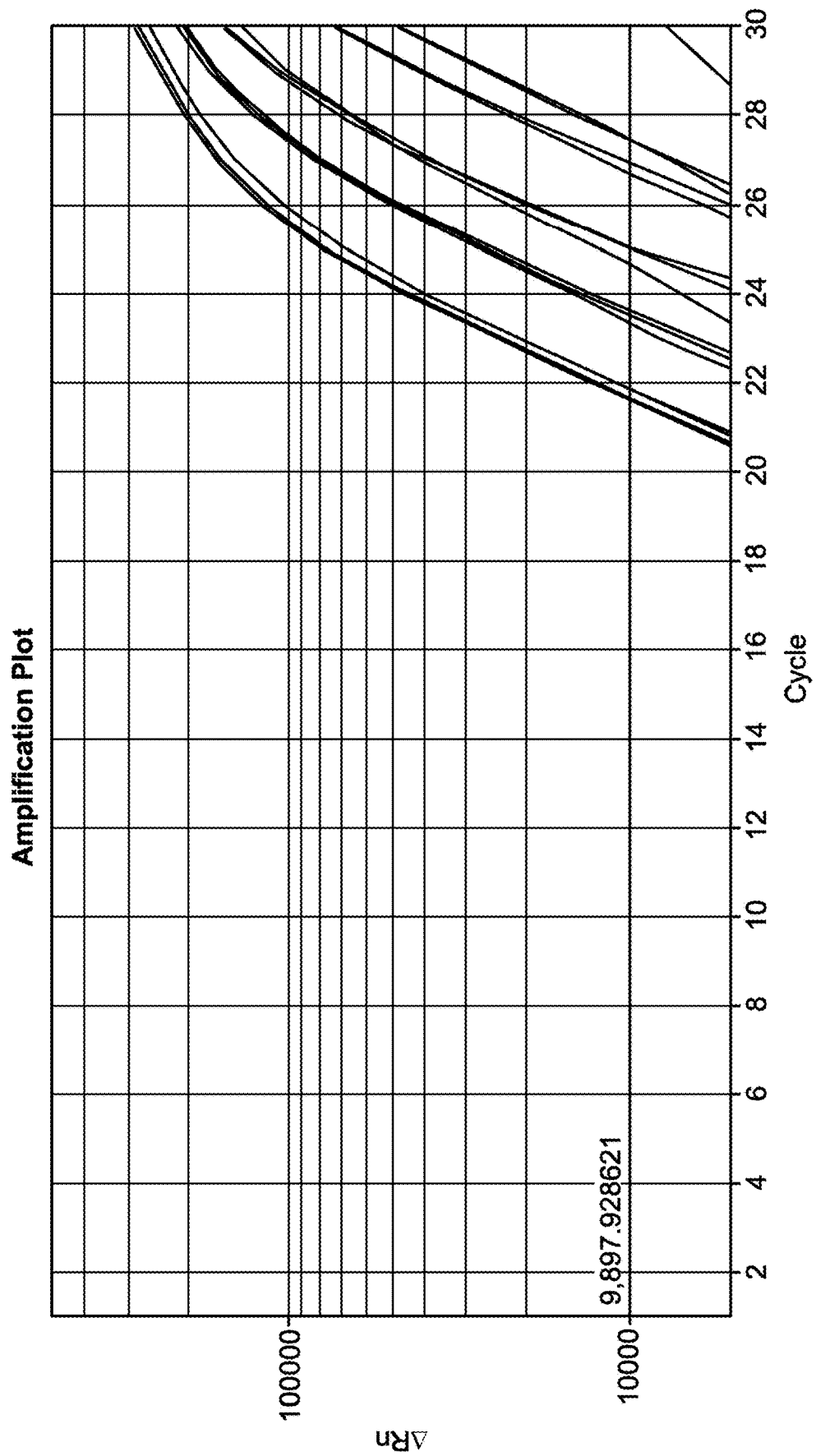
FIG. 9 is a graph illustrating results of nucleic acid amplification reactions.

*Staphylococcus aureus* Mu3 genomic DNA was obtained from ATCC (item number 700698D-5). DNA was titrated and normalized into 54 pure water to produce 54 samples having 10000.0 pg, 3333.3 pg, 1111.1 pg, 370.4 pg, 123.5 pg, or 0 pg bacterial DNA. The 0 pg sample was water only, and used as a negative control. Each of these 54 bacterial DNA samples was then added to 200ℓ of salvaged human platelets, collected by apheresis 10 days earlier. The effective pg/mL for these samples was 48780.5, 16260.2, 5420.1, 1806.7, 602.2, and 0, respectively. DNA was extracted from these 2054 samples by an automated procedure using a Maxwell 16 MDx Instrument (Promega) and Maxwell 16 LEV Blood DNA kit (Promega). 30-cycle, real-time PCR reactions were prepared in triplicate (with 6 replicas for the negative control), and run as in Example 5 (using proves and primers as in Example 1). Each reaction contained 24 of DNA extraction eluate (from 50 μL total), representing approximately 400 pg, 133.3 pg, 44.4 pg, 14.8 pg, 4.9 pg, and 0 pg of starting DNA per reaction, respectively (assuming 100% efficient recovery). A graph of resulting amplification curves is provided in FIG. 9, with each square along the x-axis representing two cycles. The groups of curves from left to right correspond to reactions containing 400 pg, 133.3 pg, 44.4 pg, 14.8 pg, 4.9 pg, and 0 pg. Quantitative results are summarized in Table 14. Results obtained for bacterial DNA titration in platelet samples were similar to those obtained for dilution in buffer (such as in Example 1). Sensitivity of detection was high, with positive detection signal at a $C_T$ of about 27.5 for a sample representing about 4.9 pg of starting material or less. Specificity was also high, as no positive signal was detected for any of the 6 negative control samples. It is expected that automated extraction will minimize false positives arising from procedural contamination.

TABLE 14

| Platelet Sample | DNA/PCRrxn (pg) | $C_T$ | Endpoint cycle 30 |
|---|---|---|---|
| S. aureus DNA | 400.0 | 21.9 | 342807 |
| S. aureus DNA | 400.0 | 21.7 | 387481 |
| S. aureus DNA | 400.0 | 21.7 | 371539 |
| Average | | 21.7 | |
| SD | | 0.1 | |
| S. aureus DNA | 133.3 | 23.7 | 303528 |
| S. aureus DNA | 133.3 | 23.4 | 300532 |
| S. aureus DNA | 133.3 | 23.5 | 308639 |
| Average | | 23.5 | |
| SD | | 0.1 | |
| S. aureus DNA | 44.4 | 25.0 | 252438 |
| S. aureus DNA | 44.4 | 24.7 | 248917 |
| S. aureus DNA | 44.4 | 25.0 | 233241 |
| Average | | 24.9 | |
| SD | | 0.2 | |
| S. aureus DNA | 14.8 | 26.8 | 159733 |
| S. aureus DNA | 14.8 | 26.9 | 175803 |
| S. aureus DNA | 14.8 | 26.8 | 176431 |
| Average | | 26.8 | |
| SD | | 0.1 | |
| S. aureus DNA | 4.9 | 27.5 | 138280 |
| S. aureus DNA | 4.9 | 27.6 | 139288 |
| S. aureus DNA | 4.9 | 27.5 | 139297 |
| Average | | 27.5 | |
| SD | | 0.0 | |
| Platelets Only | 0.0 | 30.0 | 82160 |
| Platelets only | 0.0 | 30.0 | 101844 |
| Platelets only | 0.0 | 30.0 | 94452 |
| Platelets only | 0.0 | 30.0 | 84096 |
| Platelets only | 0.0 | 30.0 | 86270 |
| Platelets only | 0.0 | 30.0 | 101131 |
| Average | | 30.0 | |
| SD | | 0.0 | |

Figure 10A:
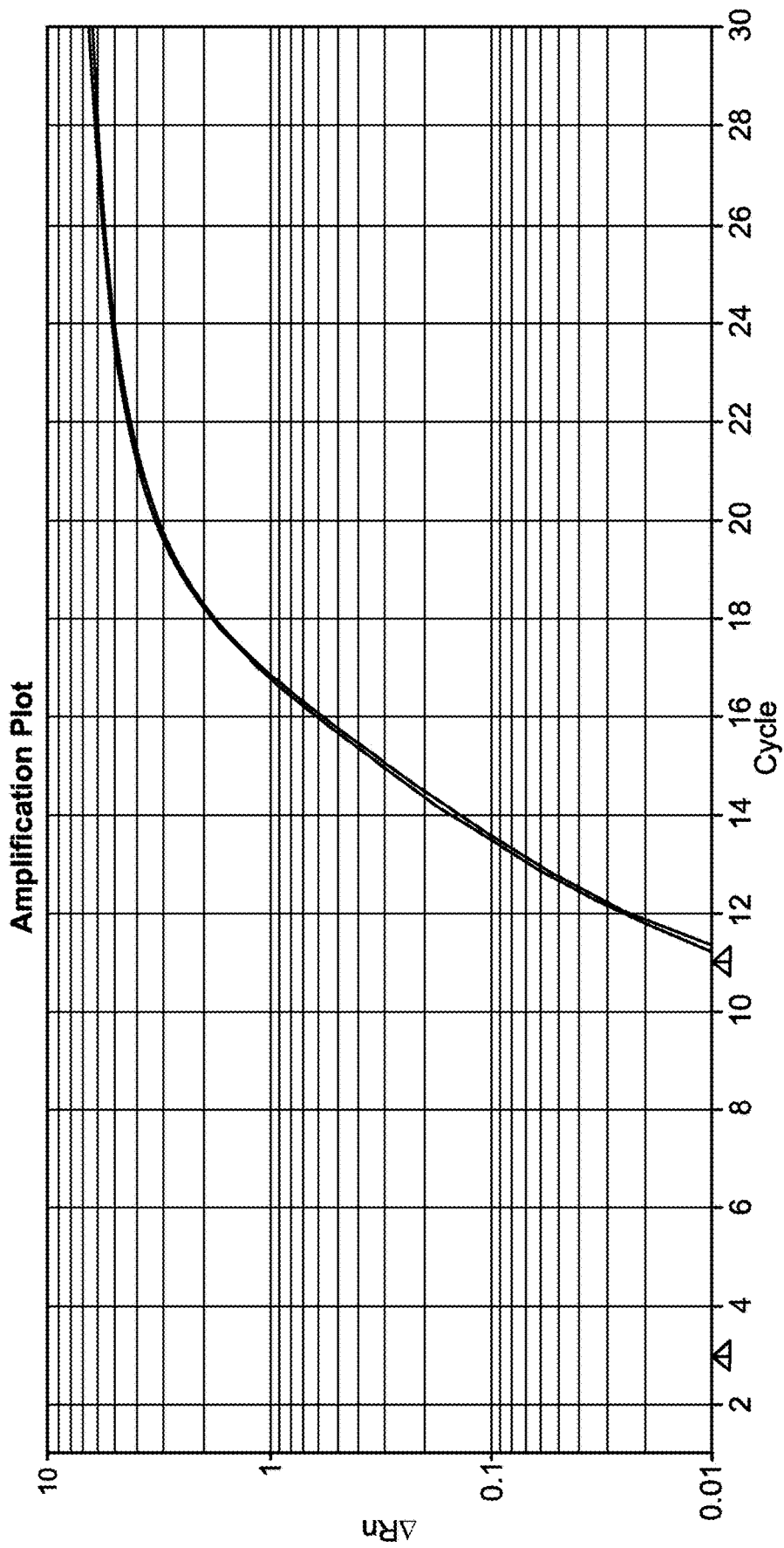
FIG. 10A is a graph illustrating results of nucleic acid amplification reactions performed in triplets.
Figure 10B:
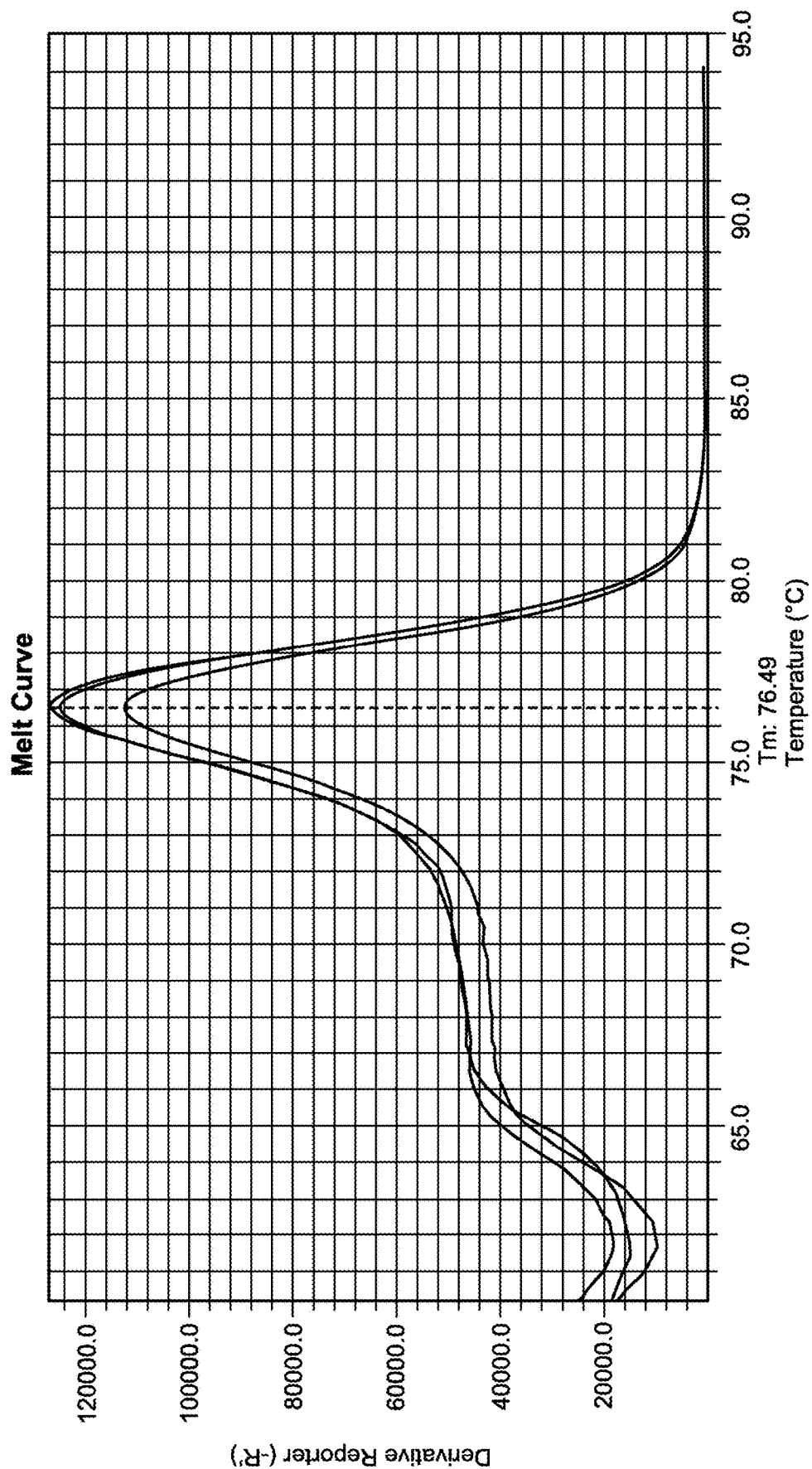
FIG. 10B is a graph illustrating results of melting curve analysis of the resulting amplified nucleic acid.

Example 9: Detection of Bacterial Contamination Using Subject Primers and DNA-Binding Agent Real-time PCR was conducted using a reaction mixture containing 250 pg of S. aureus Mu3 DNA (ATCC700698D-5), primer pairs of SEQ ID NOs. 51 and 52, and a DNA binding dye (e.g., SYBR® Green) along with other reagents provided in Fast SYBR® Green Master Mix (AB Applied Biosystems). FIG. 10A depicts the real-time amplification plot showing exponential amplification of S. aureus DNA. The results represent triplet experiments. The resulting PRC reaction was then subject to melting curve analysis. FIG. 10B depicts a single peak at the temperature expected to be indicative of specific amplification of S. aureus DNA. This experiment demonstrates that the subject primer pairs are amenable for a dye-based detection of amplified bacterial nucleic acid.

Example 10: Detection of Many Different Types of Bacterial Strains Using Subject Primers Disclosed herein are a host of primer pairs capable of detecting any types of bacteria from 20 some bacterial strains that are commonly found as source of contamination in biological samples. In particular, all of the primers and probes described in Table 2 and Table 3 have been tested and shown to be able to specifically amplify one or more target bacterial sequences in Table 1 utilizing the methods disclosed herein or known in the art. In addition, Table 15 lists exemplary pairing of the sequences that have been tested and/or shown by sequence homology to be effective primers capable of specifically amplifying the listed bacterial strains using the methods disclosed in the above examples. In particular, primer set 3 containing two primers (SEQ ID NOs 9 and 10) has been tested and demonstrated to specifically amplify and hence detect in a single amplification reaction 20 some bacterial strains covering Staphylococcus aureus, Staphylococcus aureus Mu3; Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Propionibacterium granulosum, Pseudomonas aeruginosa, Serratia marcescens, Bacillus cereus, Staphylococcus aureus Mu50, Yersinia enterocolitica, Staphylococcus simulans, Micrococcus luteus, and Enterobacter aerogenes.

The other SEQ ID NOs in this primer set (namely SEQ ID NOs. 47 and 48) are optional in that they are not required for amplifying the aforementioned bacterial strains in a single reaction. SEQ ID NO. 47 and/or SEQ ID No. 48 when used in the same reaction mixture with SEQ ID NOs. 9 and 10, is able to increase amplification sensitivity and enhance detection of Propionibacterium sp.

Similarly, primer sets 1-2 and 4-25 each have been tested and/or shown by sequence homology to be able to amplify the listed bacterial strains. Primers noted "included" exhibit at least 85%, 90% or 95% sequence homology to a conserved region of the listed bacterial strains listed under the column "Bacterial Target Coverage." Primers designated "optional" have been tested and/or predicted by sequence homology to provide more specific amplification of listed bacterial genome when used together with one or more of the "included" primers. "Optional" sequences typically exhibit at least 99% or 100% sequence homology with a target bacterial genome when optimally aligned. This series of findings demonstrates the technical advantages of these primer sets as they are both specific and able to cover a wide range of bacterial strains commonly occurred in biological samples.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition for detecting bacterial contamination of a platelet sample, comprising:

a single primer pair that, in an amplification reaction with a 16S ribosomal ribonucleic acid (16S rRNA) polynucleotide, amplifies an amplicon of at least 50 nucleotides in length; and a single detectable probe that hybridizes to either strand of the amplicon; wherein the single primer pair having a first primer and a second primer flanks the amplicon that comprises a conserved sequence to which the single detectable probe hybridizes; wherein the first primer and the second primer each hybridizes to a separate conserved region of the 16S rRNA polynucleotide; wherein the separate conserved region is identical among at least five bacterial genera; and wherein the separate conserved region is (i) selected from the group consisting of from 9 to 28, from 32 to 48, from 888 to 903, from 908 to 937, from 975 to 994, from 957 to 981, from 1093 to 1125, from 1184 to 1206, from 1231 to 1252, from 1378 to 1396, from 1398 to 1422, and from 1496 to 1516, of 16S rRNA of *Staphylococcus aureus* (GenBank accession Number NC_007622) or (ii) a corresponding region in a genome of any of the at least five bacterial genera, wherein hybridization of the single detectable probe to the either strand of the amplicon yields a detectable signal indicative of bacterial contamination of the platelet sample by the any of the at least five bacterial genera.

2. The composition of claim 1, wherein the first primer comprises a sequence as set forth in SEQ ID NO: 4, or a complement thereof, and the second primer comprises a sequence as set forth in SEQ ID NO: 5 or 6, or a complement thereof, or the first primer comprises a sequence as set forth in SEQ ID NO: 7, or a complement thereof, and the second primer comprises a sequence as set forth in SEQ ID NO: 8, or a complement thereof, or the first primer comprises a sequence as set forth in SEQ ID NO: 9, or a complement thereof, and the second primer comprises a sequence as set forth in SEQ ID NO: 10, or a complement thereof.

3. The composition of claim 2, wherein the first primer comprises the sequence as set forth in SEQ ID NO: 4, or the complement thereof, and the second primer comprises the sequence as set forth in SEQ ID NO: 5 or 6, or the complement thereof.

4. The composition of claim 2, wherein the first primer comprises the sequence as set forth in SEQ ID NO: 7, or the complement thereof, and the second primer comprises the sequence as set forth in SEQ ID NO: 8, or the complement thereof.

5. The composition of claim 2, wherein the first primer comprises the sequence as set forth in SEQ ID NO: 9, or the complement thereof, and the second primer comprises the sequence as set forth in SEQ ID NO: 10, or the complement thereof.

6. The composition of claim 1, wherein the composition is packaged as a kit.

7. The composition of claim 1, wherein, in the amplification reaction with the 16S rRNA polynucleotide, amplification of about 1 pg-5 pg of deoxyribonucleic acid (DNA) from any of a plurality of target genera by the single primer pair and the single detectable probe has a cycle threshold value ($C_T$) of less than 30.

8. The composition of claim 1, wherein the amplicon has at least 90% sequence identity with any of SEQ ID NO: 1-3, or a complement thereof when optimally aligned.

9. The composition of claim 1, wherein the single detectable probe comprises at least 10 contiguous nucleotides of a sequence selected from the group consisting of SEQ ID: 11, SEQ ID: 12, SEQ ID: 13, SEQ ID: 14, SEQ ID: 15, SEQ ID: 16, SEQ ID: 127, SEQ ID: 128, SEQ ID: 129, SEQ ID: 130, SEQ ID: 131, SEQ ID: 132, SEQ ID: 133, SEQ ID: 134, SEQ ID: 135, SEQ ID: 136, SEQ ID: 137, SEQ ID: 138, SEQ ID: 139, SEQ ID: 140, SEQ ID: 141, SEQ ID: 142, SEQ ID: 143, SEQ ID: 144, SEQ ID: 145, SEQ ID: 146, SEQ ID: 147, SEQ ID: 148, SEQ ID: 149, SEQ ID: 150, SEQ ID: 151, SEQ ID: 152, SEQ ID: 153, SEQ ID: 154, SEQ ID: 155, and a complement thereof.

10. The composition of claim 1, wherein the any of the at least five bacterial genera is selected from the group consisting of: *Staphylococcus, Streptococcus, Escherichia, Citrobacter, Clostridium, Enterococcus, Klebsiella, Lactobacillus, Listeria, Propionibacterium, Pseudomonas, Serratia, Bacillus, Yersinia, Micrococcus*, and *Enterobacter*.

11. The composition of claim 1, wherein the amplification reaction yields a detectable amount of the amplicon of no more than 150 bases.

12. A composition for detecting bacterial contamination of a platelet sample, comprising:
   a single primer pair that, in an amplification reaction with a 16S ribosomal ribonucleic acid (16S rRNA) polynucleotide, amplifies an amplicon of at least 50 nucleotides in length; and
   a single detectable probe that hybridizes to either strand of the amplicon; wherein the single primer pair flanks the amplicon that comprises a conserved sequence to which the single detectable probe hybridizes; and the conserved sequence is identical among at least five bacterial genera, wherein the single detectable probe comprises at least 10 contiguous nucleotides of a sequence selected from the group consisting of SEQ ID: 11, SEQ ID: 12, SEQ ID: 13, SEQ ID: 14, SEQ ID: 15, SEQ ID: 16, SEQ ID: 127, SEQ ID: 128, SEQ ID: 129, SEQ ID: 130, SEQ ID: 131, SEQ ID: 132, SEQ ID: 133, SEQ ID: 134, SEQ ID: 135, SEQ ID: 136, SEQ ID: 137, SEQ ID: 138, SEQ ID: 139, SEQ ID: 140, SEQ ID: 141, SEQ ID: 142, SEQ ID: 143, SEQ ID: 144, SEQ ID: 145, SEQ ID: 146, SEQ ID: 147, SEQ ID: 148, SEQ ID: 149, SEQ ID: 150, SEQ ID: 151, SEQ ID: 152, SEQ ID: 153, SEQ ID: 154, SEQ ID: 155, and a complement thereof,
   wherein hybridization of the single detectable probe to the either strand of the amplicon yields a detectable signal indicative of bacterial contamination of the platelet sample by any of the at least five bacterial genera.

13. The composition of claim 12, wherein the single primer pair comprises a first primer and a second primer, wherein the first primer and the second primer each hybridizes to a separate conserved region of the 16S rRNA polynucleotide; wherein the separate conserved region is identical among the at least five bacterial genera; and wherein the separate conserved region is (i) selected from the group consisting of from 9 to 28, from 32 to 48, from 888 to 903, from 908 to 937, from 975 to 994, from 957 to 981, from 1093 to 1125, from 1184 to 1206, from 1231 to 1252, from 1378 to 1396, from 1398 to 1422, and from 1496 to 1516, of 16S rRNA of *Staphylococcus aureus* (GenBank accession Number NC_007622) or (ii) a corresponding region in a genome of the any of the at least five bacterial genera.

14. The composition of claim 12, wherein the composition is packaged as a kit.

15. The composition of claim 12, wherein the amplicon has at least 90% sequence identity with any of SEQ ID NO: 1-3, or a complement thereof when optimally aligned.

16. The composition of claim 12, wherein the any of the at least five bacterial genera is selected from the group consisting of: *Staphylococcus, Streptococcus, Escherichia, Citrobacter, Clostridium, Enterococcus, Klebsiella, Lactobacillus, Listeria, Propionibacterium, Pseudomonas, Serratia, Bacillus, Yersinia, Micrococcus*, and *Enterobacter*.

17. The composition of claim 12, wherein the single primer pair comprises a first primer and a second primer, wherein the first primer comprises a sequence as set forth in SEQ ID NO: 4, or a complement thereof, and the second primer comprises a sequence as set forth in SEQ ID NO: 5 or 6, or a complement thereof, or the first primer comprises a sequence as set forth in SEQ ID NO: 7, or a complement thereof, and the second primer comprises a sequence as set forth in SEQ ID NO: 8, or a complement thereof, or the first primer comprises a sequence as set forth in SEQ ID NO: 9, or a complement thereof, and the second primer comprises a sequence as set forth in SEQ ID NO: 10, or a complement thereof.

18. The composition of claim 12, wherein the single detectable probe comprises at least 10 contiguous nucleotides of the sequence as set forth in SEQ ID NO: 11, 12, 13, 14, 15, 16, or the complement thereof.

19. The composition of claim 12, wherein the amplification reaction yields a detectable amount of the amplicon of no more than 150 bases.

* * * * *

SEQUENCE LISTING

<160> NUMBER OF SEQ ID NOS: 155

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caaggttgaa actcaaagga attgacgggg acccgcacaa gcggtggagc atgtggttta      60
attcgaagca acgcgaagaa ccttacc                                          87

<210> SEQ ID NO 2
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gcaacgcgaa gaaccttacc aaatcttgac atcctttgac aactctagag atagagcctt      60
ccccttcggg ggacaaagtg acaggtggtg catggttgtc gtcagctcgt gtcgtgagat     120
gttgggttaa gtcccgca                                                   138

<210> SEQ ID NO 3
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcaacgagcg caacccttaa gcttagttgc catcattaag ttgggcactc taagttgact      60
gccggtgaca aaccggagga aggtggggat gacgtcaaat catcatgccc cttatgattt     120
gggctacaca cgtgctacaa tgg                                             143

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtaaggttc ttcgcgttgc                                                  20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caaggttgaa actcaaagga attga                                            25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaggttaaa actcaaatga attga                                           25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcgggactt aacccaacat                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcaacgcgaa gaaccttacc                                                 20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccattgtagc acgtgtgtag cc                                              22

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaacgagcg caaccc                                                     16

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcgaattaaa ccacatgctc caccgct                                         27

```
<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tcgaattaat ccgcatgctc cgccgct                                         27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tcgaattaaa ccacatgctc cgctact                                         27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
agctgacgac agccatgcag cacct                                           25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
agctgacgac aaccatgcac cacct                                           25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tgacgtcatc cccaccttcc tcc                                             23

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcctacggga ggcagcagt                                                  19
```

```
<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggactaccag ggtatctaat cctgtt                                        26

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cgtattaccg cggctgctgg cac                                           23

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttgcatgta ttaggcacgc cgccagcgtt catcctgagc caggatcaaa ctct         54

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agagtttgat cctggctcag gatgaacgct ggcggcgtgc ctaatacatg caagt        55

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcgtgccta atacatgcaa gtcgagcgaa cggacgagaa gcttgcttct ctgatgttag   60
cggcggacgg gtgagtaa                                                 78

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 23
cgtgcctaat acatgcaagt cgagcgaacg gacgagaagc ttgcttctct gatgttagcg    60
gcggacgggt gagtaa                                                    76

<210> SEQ ID NO 24
<211> LENGTH: 542
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ggcgtgccta atacatgcaa gtcgagcgaa cggacgagaa gcttgcttct ctgatgttag    60
cggcggacgg gtgagtaaca cgtggataac ctacctataa gactgggata acttcgggaa   120
accggagcta ataccggata atattttgaa ccgcatggtt caaaagtgaa agacggtctt   180
gctgtcactt atagatggat ccgcgctgca ttagctagtt ggtaaggtaa cggcttacca   240
aggcaacgat gcatagccga cctgagaggg tgatcggcca cactggaact gagacacggt   300
ccagactcct acgggaggca gcagtaggga atcttccgca atgggcgaaa gcctgacgga   360
gcaacgccgc gtgagtgatg aaggtcttcg gatcgtaaaa ctctgttatt agggaagaac   420
atatgtgtaa gtaactgtgc acatcttgac ggtacctaat cagaaagcca cggctaacta   480
cgtgccagca gccgcggtaa tacgtaggtg gcaagcgtta tccggaatta ttgggcgtaa   540
ag                                                                 542

<210> SEQ ID NO 25
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cgtgcctaat acatgcaagt cgagcgaacg gacgagaagc ttgcttctct gatgttagcg    60
gcggacgggt gagtaacacg tggataacct acctataaga ctgggataac ttcgggaaac   120
cggagctaat accggataat attttgaacc gcatggttca aaagtgaaag acggtcttgc   180
tgtcacttat agatggatcc gcgctgcatt agctagttgg taaggtaacg gcttaccaag   240
gcaacgatgc atagccgacc tgagagggtg atcggccaca ctggaactga gacacggtcc   300
agactcctac gggaggcagc agtagggaat cttccgcaat gggcgaaagc ctgacggagc   360
aacgccgcgt gagtgatgaa ggtcttcgga tcgtaaaact ctgttattag gaagaacat   420 atgtgtaagt aactgtgcac atcttgacgg tacctaatca gaaagccacg gctaactacg   480
tgccagcagc cgcggtaata cgtaggtggc aagcgttatc cggaattatt gggcgtaaag   540

<210> SEQ ID NO 26
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ttactcaccc gtccgccgct aacatcagag aagcaagctt ctcgtccgtt cgctcgactt    60
gcatgtatta ggcacgccgc cagcgttcat cctgagccag gatcaaactc t            111

<210> SEQ ID NO 27
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
agtctggacc gtgtctcagt tccagtgtgg ccgatcaccc tctcaggtcg gctatgcatc    60
gttgccttgg taagccgtta ccttaccaac tagctaatgc agcgcggatc catctataag   120
tgacagcaag accgtctttc acttttgaac catgcggttc aaaatattat ccggtattag   180
ctccggtttc ccgaagttat cccagtctta taggtaggtt atccacgtgt tactcacccg   240
tccgccgcta acatcagaga agcaagcttc tcgtccgttc gctcgacttg catgtattag   300
gcacgccgcc agcgttcatc ctgagccagg atcaaactct                        340

<210> SEQ ID NO 28
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
cgcgctttac gcccaataat tccggataac gcttgccacc tacgtattac cgcggctgct    60
ggcacgtagt tagccgtggc tttctgatta ggtaccgtca agatgtgcac agttacttac   120
acatatgttc ttccctaata acagagtttt acgatccgaa gaccttcatc actcacgcgg   180
cgttgctccg tcaggctttc gcccattgcg gaagattccc tactgctgcc tcccgtagga   240
gtctggaccg tgtctcagtt ccagtgtggc cgatcaccct ctcaggtcgg ctatgcatcg   300
ttgccttggt aagccgttac cttaccaact agctaatgca gcgcggatcc atctataagt   360
gacagcaaga ccgtctttca cttttgaacc atgcggttca aaatattatc cggtattagc   420
tccggtttcc cgaagttatc ccagtcttat aggtaggtta tccacgtgtt actcacccgt   480
ccgccgctaa catcagagaa gcaagcttct cgtccgttcg ctcgacttgc atgtattagg   540
cacgccgcca gcgttcatcc tgagccagga tcaaactct                         579

<210> SEQ ID NO 29
<211> LENGTH: 782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tttgatcccc acgctttcgc acatcagcgt cagttacaga ccagaaagtc gccttcgcca    60
ctggtgttcc tccatatctc tgcgcatttc accgctacac atggaattcc actttcctct   120
tctgcactca gtttccagtt tccaatgac cctccacgg ttgagccgtg gctttcaca    180 tcagacttaa aaaccgcct acgcgcgctt tacgcccaat aattccggat aacgcttgcc   240

```
acctacgtat taccgcggct gctggcacgt agttagccgt ggctttctga ttaggtaccg    300
tcaagatgtg cacagttact tacacatatg ttcttcccta ataacagagt tttacgatcc    360
gaagaccttc atcactcacg cggcgttgct ccgtcaggct ttcgcccatt gcggaagatt    420
ccctactgct gcctcccgta ggagtctgga ccgtgtctca gttccagtgt ggccgatcac    480
cctctcaggt cggctatgca tcgttgcctt ggtaagccgt taccttacca actagctaat    540
gcagcgcgga tccatctata agtgacagca agaccgtctt tcactttga accatgcggt    600 tcaaaatatt atccggtatt agctccggtt tcccgaagtt atcccagtct tataggtagg    660
ttatccacgt gttactcacc cgtccgccgc taacatcaga gaagcaagct tctcgtccgt    720
tcgctcgact tgcatgtatt aggcacgccg ccagcgttca tcctgagcca ggatcaaact    780
ct                                                                  782
```

```
<210> SEQ ID NO 30
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cggctaacta cgtgccagca gccgcggtaa tacgtaggtg gcaagcgtta tccggaatta    60
ttgggcgtaa agcgcg                                                   76

<210> SEQ ID NO 31
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccagcagccg cggtaatacg taggtggcaa gcgttatccg gaattattgg gcgtaaagcg    60
cg                                                                  62

<210> SEQ ID NO 32
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccagcagccg cggtaatacg taggtggcaa gcgttatccg gaattattgg gcgtaaag     58

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
tgtgtagcgg tgaaatgcgc agagatatgg aggaacacca gtggcgaagg cgactttctg    60
gtctgtaact gacgctgatg tgcgaaagcg tggggatcaa                         100
```

<210> SEQ ID NO 34
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
tgtgtagcgg tgaaatgcgc agagatatgg aggaacacca gtggcgaagg cgactttctg      60
gtctgtaact gacgctgatg tgcgaaagcg tggggatcaa acaggattag ataccctggt     120
agtccacgcc gtaaacgatg                                                 140

<210> SEQ ID NO 35
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ccgcctgggg agtacgaccg caaggttgaa actcaaagga attgacgggg acccgcacaa      60
gcggtggagc atgtggttta attcgaagca acgcgaagaa ccttacc                  107

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gggagtacga ccgcaaggtt gaaactcaaa ggaattgacg ggacccgca caagcggtgg       60 agcatgtggt ttaattcgaa gcaacgcgaa gaaccttacc                          100

<210> SEQ ID NO 37
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgcaaggttg aaactcaaag gaattgacgg ggacccgcac aagcggtgga gcatgtggtt      60
taattcgaag caacgcgaag aaccttacc                                       89

<210> SEQ ID NO 38
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcaaggttga aactcaaagg aattgacggg gacccgcaca agcggtggag catgtggttt      60
aattcgaagc aacgcgaaga accttacc                                        88

```
<210> SEQ ID NO 39
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cggtgaatac gttcccgggt cttgtacaca ccgcccgtca caccacgaga gtttgtaaca      60
cccgaagccg gtggagtaac cttttaggag ctagccgtcg aaggtgggac aaatgattgg     120
ggtgaagtcg taacaagg                                                   138

<210> SEQ ID NO 40
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cggtgaatac gttcccgggt cttgtacaca ccgcccgtca caccacgaga gtttgtaaca      60
cccgaagccg gtggagtaac cttttaggag ctagccgtcg aaggtgggac aaatgattgg     120
ggtgaagtcg taacaaggta gc                                              142

<210> SEQ ID NO 41
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tgtacacacc gcccgtcaca ccacgagagt ttgtaacacc cgaagccggt ggagtaacct      60
tttaggagct agccgtcgaa ggtgggacaa atgattgggg tgaagtcgta acaaggtagc     120
cgtatcggaa ggtgcggctg atcacctcc tt                                    152

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtaaggttc tacgcgttgc                                                  20

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caaggctgaa actcaaagga attga                                            25
```

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
caaggctaaa actcaaagga attga                                           25

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tacgggactt aacccaacat                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gcaacgcgta gaaccttacc                                                 20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ccattgtagc atgcgtgaag cc                                              22

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gtaacgagcg caaccc                                                     16

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ccattgtagc acgtgtgtag ccc                                             23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccattgtagc atgcgtgaag ccc                                           23

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agagtttgat cctggctcag                                               20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgcatgtatt aggcacgcc                                                19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgcatgtgtt aggcctgcc                                                19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgcatgtgtt aagcacgcc                                                19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acttgcatgt attaggcacg                                               20

```
<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acttgcatgt gttaggcctg                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acttgcatgt gttaagcacg                                                   20

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttactcaccc gtccgcc                                                      17

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttactcaccc gttcgca                                                      17

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttactcaccc atccgcc                                                      17

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttactcaccc gttcgcc                                                      17
```

```
<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
agtctggacc gtgtctcagt tc                                             22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agtctgggcc gtgtctcagt cc                                             22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agtttgggcc gtgtctcagt cc                                             22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agtctgggcc gtatctcagt cc                                             22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctttacgccc aataattccg                                                20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctttacgccc agtaattccg                                                20
```

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ctttacgccc aataaatccg                    20

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
tttgatcccc acgcttt                       17

<210> SEQ ID NO 70
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
tttgctcccc acgcttt                       17

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ttcgctaccc atgcttt                       17

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ttcgctcccc acgcttt                       17

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
cggctaacta cgtgccagc                     19

```
<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cggctaactc cgtgccagc                                                19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cggctaactt cgtgccagc                                                19

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccagcagccg cggtaat                                                  17

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccagcagccg cggtgat                                                  17

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgcgctttac gcccaata                                                 18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tgcgctttac gcccagta                                                 18
```

```
<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctcgctttac gcccaata                                              18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81 agcccttta c gcccaata                                             18

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgtgtagcgg tgaaatgcg                                             19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggtgtagcgg tgaaatgcg                                             19

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtgtagcggt ggaatgcg                                              18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtggagcggt ggaatgcg                                              18
```

```
<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttgatcccca cgctttcg                                                    18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttgctcccca cgctttcg                                                    18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tcgctaccca tgctttcg                                                    18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tcgctcccca cgctttcg                                                    18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
catcgtttac ggcgtgga                                                    18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
catcgtttac agcgtgga                                                    18
```

```
<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
catcgtttac ggcatgga                                                 18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caccgtttac agcgtgga                                                 18

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gggagtacga ccgcaaggt                                                19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ggggagtacg gccgcaagg                                                19

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccgcctgggg agtacg                                                   16

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cgcaaggttg aaactcaaag g                                             21
```

```
<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cgcaaggtta aaactcaaat g                                          21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgcaaggctg aaactcaaag g                                          21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgcaaggcta aaactcaaag g                                          21

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcaaggttga aactcaaagg aatt                                       24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaaggttaa aactcaaatg aatt                                       24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcaaggctga aactcaaagg aatt                                       24
```

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcaaggctaa aactcaaagg aatt                                           24

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cggtgaatac gttcccgg                                                  18

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ccttgttacg acttcacccc a                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ccttgttacg acttagtcct a                                              21

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cggtgaatac gttcccgg                                                  18

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gctaccttgt tacgacttca ccc                                            23

-continued

```
<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gttaccttgt tacgacttca ccc                                            23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gctaccttgt tacgacttag tcc                                            23

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tgtacacacc gcccgtcaca                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tgtacacacc gcccgtcaag                                                20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
aaggaggtga tccagccgc                                                 19

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaggaggtga tccaaccgc                                                 19
```

```
<210> SEQ ID NO 116
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tttgatcctg gctcag                                                    16

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tttgatcatg gctcag                                                    16

<210> SEQ ID NO 118
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gaacgctggc ggc                                                       13

<210> SEQ ID NO 119
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gcctaataca tgcaagt                                                   17

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gcctaacaca tgcaagt                                                   17

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggcgtgccta atacatgca                                                 19
```

```
<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggcaggccta acacatgca                                                  19

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ggcgtgctta acacatgca                                                  19

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cgtgcctaat acatgcaagt                                                 20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
caggcctaac acatgcaagt                                                 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cgtgcttaac acatgcaagt                                                 20

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
agctgacgac agccatgcac cacct                                           25
```

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 128
acacgagctg acgacaacca tgcaccacct gt                           32

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 129
acaggtgctg catggctgtc gtcagctcgt gt                           32

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 130
acaggtggtg catggctgtc gtcagctcgt gt                           32

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic probe

<400> SEQUENCE: 131
aacgctggcg gcgtgc                                             16

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic probe

<400> SEQUENCE: 132
aacgctggcg gcaggc                                             16

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 133
cggcgtgcct aatacatgca ag                                     22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 134
cggcaggcct aacacatgca ag                                              22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 135
cggcaggctt aacacatgca ag                                              22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 136
cggcgtgctt aacacatgca ag                                              22

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 137
cgtaggtggc aagcgttatc cggaa                                           25

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 138
cggagggtgc aagcgttaat cggaa                                           25

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 139
cgtaggtccc gagcgttgtc cggat                                           25

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 140
cagtggcgaa ggcgactttc tg                                          22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 141 caggggccg ccttcgccac cg                                           22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 142
cagagagccg ctttcgccac cg                                          22

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 143
gggatcaaac aggattagat accctggt                                    28

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 144
gggagcaaac aggattagat accctggt                                    28

<210> SEQ ID NO 145
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 145
gggagcgaac aggcttagat accctggt                                    28

```
<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
acaagcggtg gagcatgtgg tttaattc                                          28

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
acaagcggcg gagcatgcgg attaattc                                          28

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
acaagtagcg gagcatgtgg tttaattc                                          28

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
agcggtggag catgtggttt aattcg                                            26

<210> SEQ ID NO 150
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
agcggcggag catgcggatt aattcg                                            26

<210> SEQ ID NO 151
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
agtagcggag catgtggttt aattcg                                            26
```

```
<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
aagcggtgga gcatgtggtt taattcg                                           27

<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
agcggcggag catgcggatt aattcg                                            26

<210> SEQ ID NO 154
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
agtagcggag catgtggttt aattcg                                            26

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
tgtacacacc gcccgtca                                                     18
```